(12) United States Patent
Yaghi et al.

(10) Patent No.: US 8,480,792 B2
(45) Date of Patent: *Jul. 9, 2013

(54) PREPARATION OF FUNCTIONALIZED ZEOLITIC FRAMEWORKS

(75) Inventors: Omar M. Yaghi, Los Angeles, CA (US); Hiroyasu Furukawa, Los Angeles, CA (US); Bo Wang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 514 days.

This patent is subject to a terminal disclaimer.

(21) Appl. No.: 12/669,616

(22) PCT Filed: Jul. 16, 2008

(86) PCT No.: PCT/US2008/070149
§ 371 (c)(1),
(2), (4) Date: Mar. 1, 2010

(87) PCT Pub. No.: WO2009/020745
PCT Pub. Date: Feb. 12, 2009

(65) Prior Publication Data
US 2010/0186588 A1    Jul. 29, 2010

Related U.S. Application Data

(63) Continuation-in-part of application No. PCT/US2008/006008, filed on May 9, 2008.

(60) Provisional application No. 60/950,295, filed on Jul. 17, 2007.

(51) Int. Cl.
*B01D 53/02* (2006.01)
*C01B 39/00* (2006.01)

(52) U.S. Cl.
USPC ............. 95/116; 95/141; 95/143; 548/101; 548/108

(58) Field of Classification Search
USPC ............ 96/108, 153, 154; 95/90, 116, 127, 95/128, 130, 131, 139–141, 143, 900, 902; 548/101, 108; 210/502.1, 660; 502/400
See application file for complete search history.

(56) References Cited

U.S. PATENT DOCUMENTS 4,532,225 A    7/1985    Tsao et al.
5,160,500 A    11/1992    Chu et al.
(Continued)

FOREIGN PATENT DOCUMENTS

DE    102005023856 A1    11/2006
DE    102005054523 A1    5/2007
(Continued)

OTHER PUBLICATIONS

Ashton, Peter R. et al., "Hydrogen-Bonded Complexes of Aromatic Crown Ethers with (9-Anthracenyl) methylammonium Derivatives" J. Am. Chem. Soc., 1997, 119 (44), pp. 10641-10651.
(Continued)

*Primary Examiner* — Frank Lawrence, Jr.
(74) *Attorney, Agent, or Firm* — Joseph R. Baker, Jr.; Gavrilovich, Dodd & Lindsey LLP

(57) ABSTRACT

The disclosure provides zeolitic frameworks for gas separation, gas storage, catalysis and sensors. More particularly the disclosure provides zeolitic frameworks (ZIFs). The ZIF of the disclosure comprises any number of transition metals or a homogenous transition metal composition.

39 Claims, 43 Drawing Sheets

U.S. PATENT DOCUMENTS

| | | | |
|---|---|---|---|
| 5,208,335 | A | 5/1993 | Ramprasad et al. |
| 5,648,508 | A | 7/1997 | Yaghi |
| 6,479,447 | B2 | 11/2002 | Bijl et al. |
| 6,501,000 | B1 | 12/2002 | Stilbrany et al. |
| 6,617,467 | B1 | 9/2003 | Muller et al. |
| 6,624,318 | B1 | 9/2003 | Mueller et al. |
| 6,893,564 | B2 | 5/2005 | Mueller et al. |
| 6,929,679 | B2 | 8/2005 | Mueller et al. |
| 6,930,193 | B2 | 8/2005 | Yaghi et al. |
| 7,196,210 | B2 | 3/2007 | Yaghi et al. |
| 7,202,385 | B2 | 4/2007 | Mueller et al. |
| 7,279,517 | B2 | 10/2007 | Mueller et al. |
| 7,309,380 | B2 | 12/2007 | Mueller et al. |
| 7,343,747 | B2 | 3/2008 | Mueller et al. |
| 7,411,081 | B2 | 8/2008 | Mueller et al. |
| 7,524,444 | B2 | 4/2009 | Hesse et al. |
| 7,582,798 | B2 | 9/2009 | Yaghi et al. |
| 7,652,132 | B2 | 1/2010 | Yaghi et al. |
| 7,662,746 | B2 | 2/2010 | Yaghi et al. |
| 7,799,120 | B2 | 9/2010 | Yaghi et al. |
| 7,815,716 | B2 | 10/2010 | Mueller et al. |
| 2003/0004364 | A1 | 1/2003 | Yaghi et al. |
| 2003/0078311 | A1 | 4/2003 | Muller et al. |
| 2003/0148165 | A1 | 8/2003 | Muller et al. |
| 2003/0222023 | A1 | 12/2003 | Mueller et al. |
| 2004/0081611 | A1 | 4/2004 | Muller et al. |
| 2004/0225134 | A1 | 11/2004 | Yaghi et al. |
| 2004/0249189 | A1 | 12/2004 | Mueller et al. |
| 2004/0265670 | A1 | 12/2004 | Muller et al. |
| 2005/0004404 | A1 | 1/2005 | Muller et al. |
| 2005/0014371 | A1 | 1/2005 | Tsapatsis |
| 2005/0124819 | A1 | 6/2005 | Yaghi et al. |
| 2005/0154222 | A1 | 7/2005 | Muller et al. |
| 2005/0192175 | A1 | 9/2005 | Yaghi et al. |
| 2006/0057057 | A1 | 3/2006 | Muller et al. |
| 2006/0135824 | A1 | 6/2006 | Mueller et al. |
| 2006/0154807 | A1 | 7/2006 | Yaghi et al. |
| 2006/0185388 | A1 | 8/2006 | Muller et al. |
| 2006/0252641 | A1 | 11/2006 | Yaghi et al. |
| 2006/0252972 | A1 | 11/2006 | Pilliod et al. |
| 2006/0287190 | A1 | 12/2006 | Eddaoudi et al. |
| 2007/0068389 | A1 | 3/2007 | Yaghi et al. |
| 2007/0202038 | A1* | 8/2007 | Yaghi et al. ............ 423/702 |
| 2008/0184883 | A1 | 8/2008 | Zhou et al. |
| 2009/0155588 | A1 | 6/2009 | Hesse et al. |
| 2009/0216059 | A1* | 8/2009 | Reyes et al. ............ 585/823 |
| 2010/0132549 | A1* | 6/2010 | Yaghi et al. ............ 95/128 |
| 2010/0143693 | A1 | 6/2010 | Yaghi et al. |
| 2010/0286022 | A1 | 11/2010 | Yaghi et al. |
| 2011/0137025 | A1 | 6/2011 | Yaghi et al. |
| 2011/0282067 | A1* | 11/2011 | Li et al. ............ 548/101 |
| 2012/0028846 | A1* | 2/2012 | Yaghi et al. ............ 506/39 |

FOREIGN PATENT DOCUMENTS

| | | | |
|---|---|---|---|
| EP | 1674555 | A1 | 6/2006 |
| WO | 2004101575 | A2 | 11/2004 |
| WO | 2006072573 | A2 | 7/2006 |
| WO | 2006116340 | A1 | 11/2006 |
| WO | 2007101241 | A2 | 9/2007 |
| WO | 2007111739 | A2 | 10/2007 |
| WO | 2008091976 | A1 | 7/2008 |
| WO | 2008138989 | A1 | 11/2008 |
| WO | 2008140788 | A1 | 11/2008 |
| WO | 2009042802 | A1 | 4/2009 |
| WO | 2009149381 | A2 | 12/2009 |
| WO | 2010078337 | A1 | 7/2010 |
| WO | 2010080618 | A1 | 7/2010 |
| WO | 2010083418 | A1 | 7/2010 |
| WO | 2010088629 | A1 | 8/2010 |
| WO | 2010090683 | A1 | 8/2010 |
| WO | 2010148276 | A3 | 12/2010 |
| WO | 2010148296 | A3 | 12/2010 |
| WO | 2010148374 | A3 | 12/2010 |
| WO | 2011014503 | A1 | 2/2011 |
| WO | 2011038208 | A2 | 3/2011 |

OTHER PUBLICATIONS

Carlucci, Lucia et al., "Polycatenation, polythreading and polyknotting in coordination network chemistry" Coordination Chemistry Reviews 246, 2003, pp. 247-289, Elsevier.

Han, SS et al., "Improved designs of metal-organic frameworks for hydrogen storage" Angew. Chem. Int. Ed. 2007, 46, pp. 6289-6292.

Kim, Su Mi, International Search Report and Written Opinion, Date of Mailing: Feb. 24, 2010, International Application No. PCT/US09/46463.

Loeb, SJ, "Rotaxanes as ligands: from molecules to materials" Chemical Society reviews, 2007, 36, pp. 226-235.

Moyse, Ellen, International Preliminary Report on Patentability and Written Opinion, Date of Issuance of Report: Nov. 17, 2009, International Application No. PCT/US08/006008.

Nickitas-Etienne, Athina, International Preliminary Report on Patentability and Written Opinion, Date of Issuance of Report: Jan. 19, 2010, International Application No. PCT/US08/70149.

Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.

Wong-Foy, AG et al., "Exceptional H2 saturation uptake in microporous metal-organic frameworks" J. Am. Chem. Soc., 2006, 128, pp. 3494-3495.

Young, Lee W., International Search Report and Written Opinion, Date of Mailing of Report: May 7, 2008, International Application No. PCT/US08/51859.

Young, Lee W., "International search Report and Written Opinion," PCT/US08/06008, United States Patent & Trademark Office, Aug. 20, 2008.

Young, Lee W., International Search Report and Written Opinion, Date of Mailing: Dec. 2, 2008, International Application No. PCT/US08/77741.

Yang, Lee W., PCT/US08/70149, Written Opinion, Dec. 22, 2008, United States Patent & Trademark Office.

Nickitas-Etienne, Athina. International Preliminary Report on Patentability for PCT/US2009/068849. Date of Mailing: Jun. 30, 2011.

O'Keefe et al., "Germanate Zeolites: Contrasting the Behavior of Germanate and Silicate Structures Built from Cubic T8O20 units (T=Si or Ge)," Chem. Eur. J. 5:2796-2801 (1999).

O'Keefe et al., "Frameworks for Extended Solids: Geometrical Design Principles," J. Solid State Chem. 152:3-20 (2000).

Okeeffe et al., "Reticular Chemistry—Present and Future Prospects—Introduction," J. Solid State Chem.178:V-VI (2005).

O'Keeffe et al., "The Reticular Chemistry Structure Resource (RCSR) Database of, and Symbols for, Crystal Nets," Acc. Chem. Res. 41:1782-1789 (2008).

Park, Jae Woo. International Search Report for PCT/US2010/039123. Date of Mailing: Feb. 24, 2011.

Patteux, Claudine. International Search Report for PCT/US2010/043373. Date of Mailing: Oct. 10, 2010.

Phan et al., "Synthesis, Structure, and Carbon Dioxide Capture Properties of Zeolitic Imidazolate Frameworks," Acc. Chem. Res 43:58-67 (2009).

Plevert et al., "A Flexible Germanate Structure Containing 24-Ring Channels With Very Low Framework Density," J. Am. Chem. Soc. 123:12706-12707 (2001).

Plevert et al., "Synthesis and Characterization of Zirconogermanates," Inorg. Chem., 42:5954-5959 (2003).

Plevert et al., "Layered Structures Constructed from New Linkages of Ge7(O,OH,F)19 Clusters," Chem. Mater. 15:714-718 (2003).

Rosi et al., "Advances in the Chemistry of Metal-Organic Frameworks," CrystEngComm 4:401-404 (2002).

Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.

Rowsell et al., "Hydrogen Sorption in Functionalized Metal-Organic Frameworks," J. Am. Chem. Soc.126: 5666-5667 (2004).

Rowsell et al., "Strategies for Hydrogen Storage in Metal-Organic Frameworks," Angew. Chem. Int. Ed. 44: 4670-4679 (2005).

Rowsell et al., "Gas Adsorption Sites in a Large-Pore Metal-Organic Framework," Science 309:1350-1354 (2005).

Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).

Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.

Sudik et al., "Metal-Organic Frameworks Based on Trigonal Prismatic Building Blocks and the New "acs" Topology," Inorg. Chem. 44:2998-3000 (2005).

Sudik et al., "A Metal-Organic Framework with a Hierarchical System of Pores and Tetrahedral Bbuilding Blocks," Angew. Chem. Int. Ed. 45:2528-2533 (2006).

Vodak et al., "Computation of Aromatic C3N4 Networks and Synthesis of the Molecular Precursor N(C3N3)3C16," Chem. Eur. J. 9:4197-4201 (2003).

Wang et al., "Colossal Cages in Zeolitic Imidazolate Frameworks as Selective Carbon Dioxide Reservoirs," Nature 453:207-211 (2008).

Yaghi et al., "Selective binding and removal of guests in a microporous metal-organic framework," Nature, Dec. 1995, pp. 703-706, vol. 378.

Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.

Yaghi et al., "Construction of Microporous Materials from Molecular Building Blocks," Fundamental Materials Research, T. J. Pinnavaia and M. F. Thorpe, eds., vol. II, Plenum: New York, p. 111 (1995).

Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).

Yaghi et al., "Designing Microporosity in Coordination Solids," Modular Chemistry, J. Michl, Ed., Kluwer: Boston, p. 663 (1997).

Yaghi et al., "Synthetic Strategies, Structure Patterns, and Emerging Properties in the Chemistry of Modular Porous Solids," Acc. Chem. Res. 31:474-484 (1998).

Yaghi et al., "Transformation of Germanium Dioxide to 4-Connected Porous Germanate Net," J. Am. Chem. Soc., 20:10569-10570 (1998).

Yaghi et al., "Design of Solids from Molecular Building Blocks: Golden Opportunities for Solid State Chemistry," J. Solid State Chem. 152, 1-2 (2000).

Yaghi et al., "A Molecular World Full of Holes," Chem. Innov. p. 3 (2000).

Yaghi et al., "Reticular Synthesis and the Design of New Materials," Nature 423:705-714 (2003).

Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.

Yaghi et al., "Metal-Organic Frameworks: A Tale of Two Entanglements," Nature materials 6:92-93 (2007).

Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.

Yaghi et al., "Reticular Chemistry and Metal-Organic Frameworks for Clean Energy," MRS Bulletin 34:682-690 (2009).

Young, Lee W., International Search Report and Written Opinion, Date of Mailing: Jan. 12, 2009, International Application No. PCT/US08/70149.

Young, Jung Doo. International Search Report for PCT/US2010/050170. Date of Mailing: Jun. 8, 2011.

Zhang et al., "Docking in Metal-Organic Frameworks," Science 325:855-859 (2009).

Andrew et al., "Post-Synthetic Modification of Tagged MOFs," Angew. Chem. Int. Ed. 47:8482-8486 (2008).

Baharlou, Simin. International Preliminary Report on Patentability for PCT/US2009/046463. Date of Mailing: Dec. 16, 2010.

Banerjee et al., "High-Throughput Synthesis of Zeolitic Imidazolate Frameworks and Application to CO2 Capture," Science 319:939-943 (2008).

Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).

Barman et al., "Azulene Based Metal-Organic Frameworks for Strong Adsorption of H2," Chem. Commun. 46: 7981-7983 (2010).

Barton et al., "Tailored Porous Materials," Chem. Mater. 11:2633-2656 (1999).

Bloch et al., "Metal Insertion in a Microporous Metal-Organic Framework Lined with 2,2'-Bipyridine" J. Am. Chem. Soc. 132:14382-14384 (2010).

Chae et al., "A Route to High Surface Area, Porosity and Inclusion of Large Molecules in Crystals," Nature 427, 523-527 (2004); Featured in (1) Chemical & Engineering News magazine, Feb. 9, 2004, (2) BBC World Service, Feb. 04, (3) New Scientist, Feb. 04.

Czaja et al., "Industrial applications of metal-organic frameworks," Chemical Society Reviews 38(5):1284-1293 (2009).

Delgado-Friedrichs et al., "Three-Periodic Nets and Tilings: Regular and Quasiregular Nets," Acta Cryst. A59: 22-27 (2003).

Delgado-Friedrichs et al., "Three-Periodic Nets and Tilings: Semiregular Nets," Acta Cryst. A59:515-525 (2003).

Delgado-Friedrichs et al., "The CdSO4, Rutile, Cooperate and Quartz Dual Nets: Interpenetration and Catenation," Solid State Sciences 5:73-78 (2003).

Delgado-Friedrichs et al., "Reticular Chemistry: Occurrence and Taxonomy of Nets, and Grammar for the Design of Frameworks," Acc. Chem. Res. 38:176-182 (2005).

Delgado-Friedrichs et al. "What Do We Know About Three-Periodic Nets?," J. Solid State Chem. 178: 2533-2554 (2005).

Delgado-Friedrichs et al. "Three-Periodic Nets and Tilings: Edge-Transitive Binodal Structures," Acta Cryst. 62:350-355 (2006).

Delgado-Friedrichs et al., "Taxonomy of Periodic Nets and the Design of Materials," Phys. Chem. 9:1035-1043 (2007).

Deng et al., "Multiple Functional Groups of Varying Ratios in Metal-Organic Frameworks," Science 327:846-850 (2010).

Deng et al., "Robust dynamics" Nature Chem. 2:439-443 (2010).

Duren et al., "Design of New Materials for Methane Storage," Langmuir 20:2683-2689 (2004).

Eddaoudi et al., "Modular Chemistry: Secondary Building Units as a Basis for the Design of Highly Porous and Robust Metal-Organic Carboxylate Frameworks" Acc. Chem. Res. 34:319-330 (2001).

Eddaoudi et al., "Geometric Requirements and Examples of Important Structures in the Assembly of Square Building Blocks," Proc. Natl. Acad. Sci. 99:4900-4904 (2002).

Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.

Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).

Furukawa et al., "Ultra-High Porosity in Metal-Organic Frameworks," Science 239:424-428 (2010).

Goebel, Matthias, Supplemental European Search Report and Written Opinion for EP08826913. Date of Completion of Search and Written Opinion: Nov. 10, 2010.

Goebel, Matthias, Supplemental European Search Report and Written Opinion for EP08754337. Date of Completion of Search and Written Opinion: Dec. 3, 2010.

Grzesiak et al., "Polymer-Induced Heteronucleation for the Discovery of New Extended Solids," Angew. Chem. Int. Ed. 45:2553-2556 (2006).

Halper et al., "Topological Control in Heterometallic Metal-Organic Frameworks by Anion Templating and Metalloligand Design," J. Am. Chem. Soc. 128:15255-15268 (2006).

Hayashi et al., "Zeolite A Imidazolate Frameworks," Nature Materials 6:501-506 (2007).

Hexiang et al., "Multiple Functional Groups of Varying Rations in Metal-Organic Frameworks," Science 327 (5967):846-850 (2010).

Honda, Masashi, International Preliminary Report on Patentability for PCT/US2008/051859. Date of Issuance of the Report: Jul. 28, 2009.

Howe, Patrick. International Search Report and Written Opinion for PCT/US2009/068849. Date of Mailing of the Search Report: Jun. 4, 2011.

Howe, Patrick. International Search Report and Written Opinion for PCT/US2010/022777. Date of Mailing: Jun. 7, 2010.

Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).

Kim, Su Mi, International Search Report and Written Opinion for PCT/US2009/068731. Date of Mailing: Aug. 19, 2010.

Kim, Su Mi. International Search Report for PCT/US2010/039154. Date of Mailing: Feb. 23, 2011.

Klaes, Daphne. International Search Report and Written Opinion for PCT/US2010/021201. Date of Mailing: Apr. 27, 2010.

Lee, Ji Min. International Search Report for PCT/US2010/039284. Date of Mailing: Feb. 22, 2011.

Li et al., "Design and Synthesis of an Exceptionally Stable and Highly Porous Metal-Organic Framework," Science 402:276-279 (1999); Featured in (1) Chemical and Engineering News (Nov. 22, 19999) and (2) Science News (Nov. 20, 1999).

Linder, Nora. International Preliminary Report on Patentability for PCT/US2010/022777. Date of Mailing: Aug. 11, 2011.

Long et al., "The Pervasive Chemistry of Metal-Organic Frameworks," Chem. Soc. Rev. 38:1213-1214 (2009).

Lu et al., "Synthesis and Structure of Chemically Stable Metal-Organic Polyhedra," J. Am. Chem. Soc. 131:(35) 12532-12533 (2009).

Michalitsch, Richard. International Search Report and Written Opinion for PCT/US2009/069700. Date of Mailing: May 7, 2010.

Morris et al., "Crystals as Molecules: Postsynthesis Covalent Functionalization of Zeolitic Imidazolate Frameworks," J. Am. Chem. Soc. 130:12626-12627 (2008).

Morris et al., "A Combined Experimental-Computational Investigation of Carbon Dioxide Capture in a Series of Isoreticular Zeolitic Imidazolate Frameworks," J. Am. Chem. Soc. 132:11006-11008 (2010).

Mulhausen, Dorothee. International Preliminary Report on Patentability for PCT/US2009/069700. Date of Mailing: Jul. 7, 2011.

Mulhausen, Dorothee. International Preliminary Report on Patentability for PCT/US2010/021201. Date of Mailing Jul. 28, 2011.

Ni et al,. "Porous Metal-Organic Truncated Octahedron Constructed from Paddle-Wheel Squares and Terthiophene Links," J. Am. Chem. Soc. 127:12752-12753 (2005).

Nickitas-Etienne, Athina. International Preliminary Report on Patentability for PCT/US2008/07741. Date of issuance of this report: Mar. 30, 2010.

Nickitas-Etienne, Athina, International Preliminary Report on Patentability for PCT/US2009/068731. Date of Issuance of the Report: Jun. 21, 2011.

* cited by examiner cag

ZIF-61 znl frl

ZIF-23 dia

ZIF-77

ZIF-73

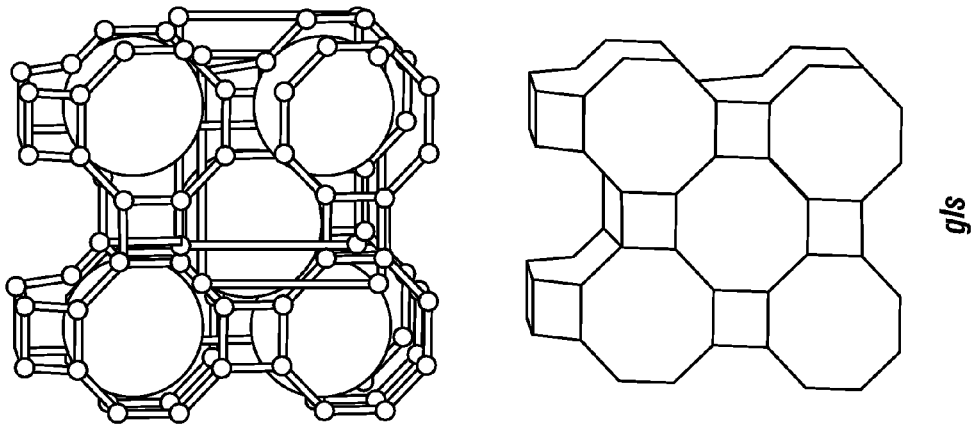
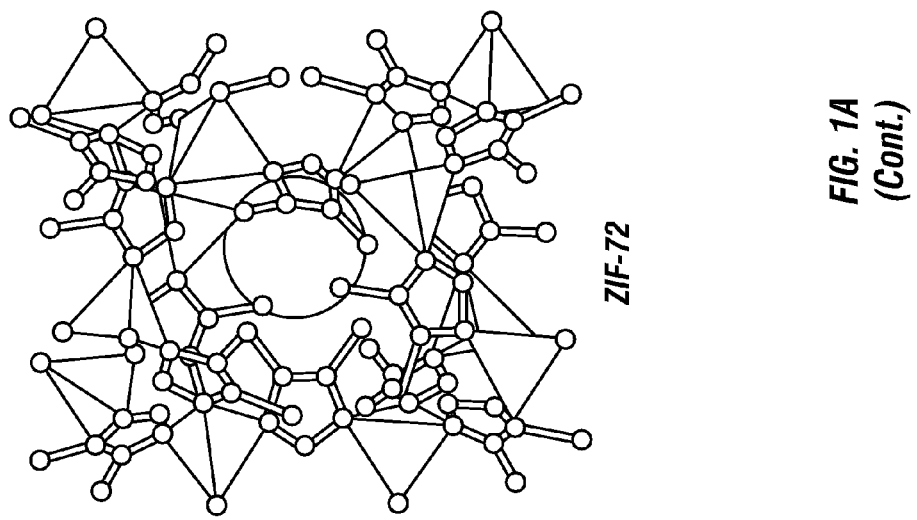
FIG. 1A (Cont.)
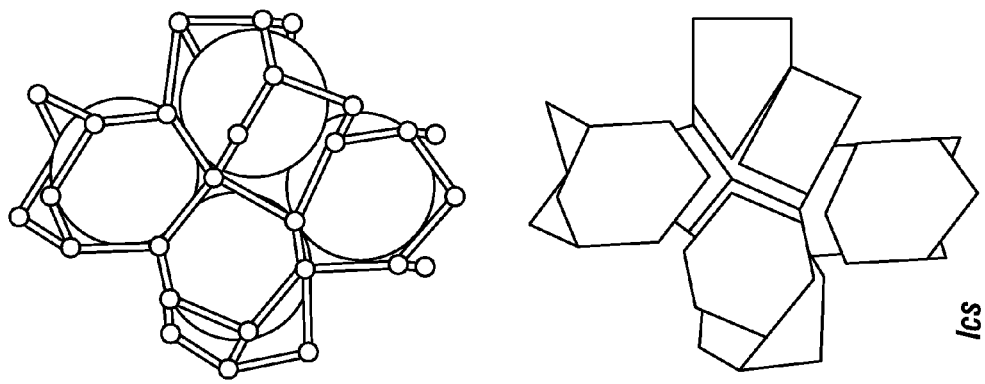

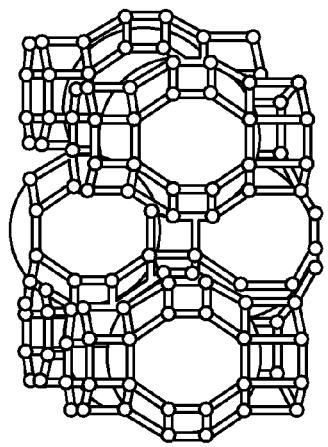
mer
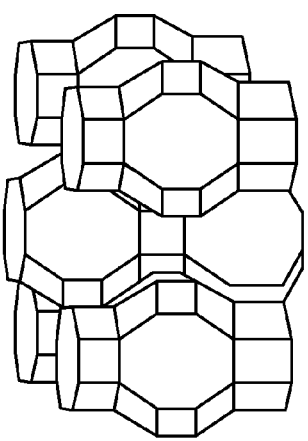
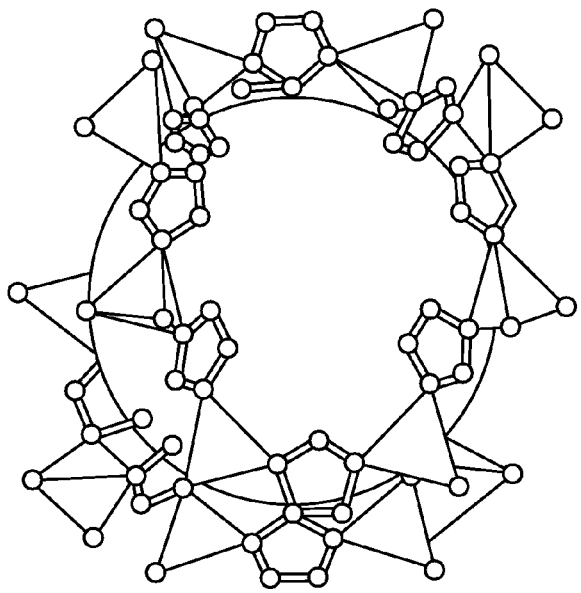
ZIF-3
FIG. 1A
(Cont.)
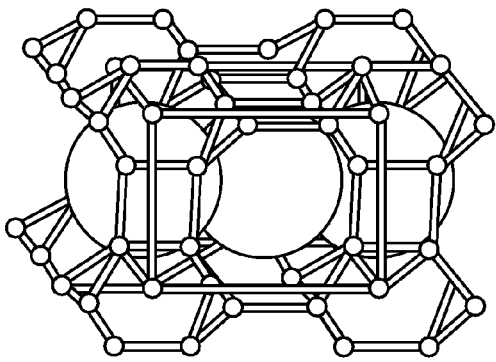
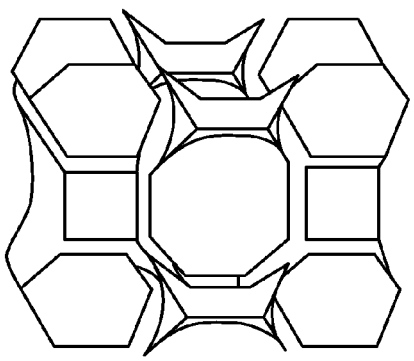
dft

ZIF-67

ZIF-65

ZIF-71

ZIF-12 poz A  poz B poz C  poz D moz

| Materials Codes | Surface area / m²g⁻¹ | Pore volume / cm³g⁻¹ |
|---|---|---|
| ZIF-20 | 790 | 0.27 |
| ZIF-25 | 1500 | 0.48 |
| ZIF-100 | 480 | 0.30 |
| ZIF-108 | 630 | 0.60 |

| Materials Codes | Low pressure (273 K) | | High pressure (298 K) | | High pressure (273 K) | |
|---|---|---|---|---|---|---|
| | Uptake / cm³ g⁻¹ | Pressure / Torr | Uptake / wt % | Pressure / bar | Uptake / wt % | Pressure / bar |
| ZIF-20 | 71 | 760 | - | - | - | - |
| ZIF-25 | 26 | 760 | - | - | - | - |
| ZIF-26 | 27 | 760 | - | - | - | - |
| ZIF-100 | 52 | 760 | - | - | - | - |
| ZIF-105 | 31 | 760 | - | - | - | - |
| ZIF-108 | 70 | 760 | - | - | - | - |

FIG. 12

| Materials Codes | Low pressure (77 K) | | High pressure (77 K) | | High pressure (298 K) | |
|---|---|---|---|---|---|---|
| | Uptake / cm³ g⁻¹ | Pressure / Torr | Uptake / wt % | Pressure / bar | Uptake / wt % | Pressure / bar |
| ZIF-20 | 117 | 803 | - | - | - | - |
| ZIF-25 | 119 | 799 | - | - | - | - |
| ZIF-26 | 126 | 804 | - | - | - | - |
| ZIF-100 | 89 | 802 | - | - | - | - |
| ZIF-105 | 90 | 802 | - | - | - | - |
| ZIF-108 | 148 | 805 | - | - | - | - |

FIG. 14

PREPARATION OF FUNCTIONALIZED ZEOLITIC FRAMEWORKS

CROSS REFERENCE TO RELATED APPLICATIONS

This application is a National Stage Application filed under 35 U.S.C. §371 from International Application No. PCT/US08/70149, filed 16 Jul. 2008, which application claims priority under 35 U.S.C. §119 to U.S. Provisional Application Ser. No. 60/950,295, filed Jul. 17, 2007, the disclosure of which are incorporated herein by reference in their entirety.

STATEMENT REGARDING FEDERALLY SPONSORED RESEARCH

This invention was made with government support under Grant No. DE-FG36-05GO15001:A005 awarded by the Department of Energy. The government has certain rights in the invention;

FIELD OF THE INVENTION

This invention relates to crystalline zeolites and to methods of use thereof.

BACKGROUND

A large segment of the global economy ($350 billion) is based on the use of crystalline microporous zeolites in petrochemical cracking, ion-exchange for water softening and purification, and in the separation of gases. Zeolite structures are composed of tetrahedral $Si(Al)O_4$ units covalently joined by bridging O atoms to produce ~150 different types of framework.

SUMMARY

The disclosure provides a zeolitic framework, comprising the general structure: a structure M-L-M, wherein M comprises a transition metal and L is a linking moiety, wherein the framework is selected from the group consisting of:

(a) M-L-M, wherein L comprises structure III; and
(b) M-L-M, wherein at least one L is structure III and at least one other L is a structure I, II or a combination thereof:

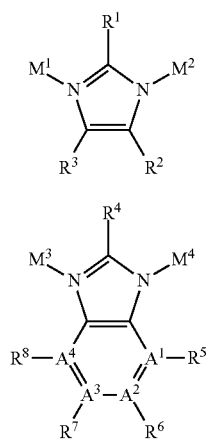

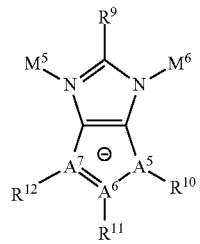

wherein A can be either C or N, wherein $R^5$-$R^8$ are present when $A^1$ and $A^4$ comprise C, wherein $R^1$, $R^4$ or $R^9$ comprise a non-sterically hindering group that does not interfere with M, wherein $R^2$, $R^3$, $R^5$, $R^8$, $R^{10}$, $R^{11}$, $R^{12}$ are each individually an alkyl, halo-, cyano-, or nitro-, wherein when the linking moiety comprises structure III, $R^{10}$, $R^{11}$ and $R^{12}$ are each individually electron withdrawing groups, and wherein one of $R^6$ and $R^7$ comprise an electron withdrawing group.

In one embodiment, $R^1$, $R^4$ or $R^9$ comprise a non-sterically hindering electron donating group that does not interfere with M. The $R^1$, $R^4$ or $R^9$ functionalized with a group selected to interact with a particular gas or substrate. In another embodiment, $R^2$, $R^3$, $R^6$, $R^7$, or $R^{11}$ are individually H or a small electron withdrawing group. In one aspect, the small electron withdrawing group is of sufficient size to increase a cage size for a ZIF of the disclosure. For example, $R^7$ can be a chloro-group.

In a further embodiment the imidazolate or imidazolate derivative is selected from the group consisting of IV, V, VI, VII, VIII, and IX:

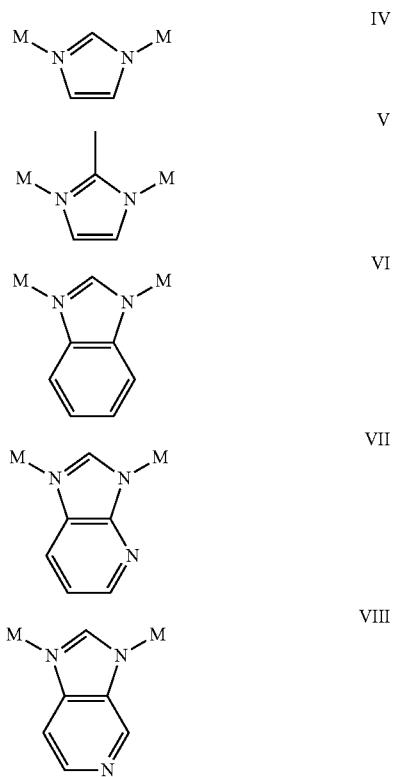

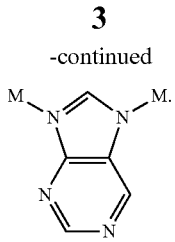

IX

In one embodiment, the imidazolate or imidazolate derivative is selected from the group consisting of a substituted imidazolate; a benzimidazolate comprising a methyl-, nitro-, cyano, or chloro-group; an azabenzimidazolate; and an azabenzimidazolate wherein one or two carbon atoms on the benzimidazolate are replaced by nitrogen. The transition metal is selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub. In one aspect, a zeolitic framework comprises a heterogeneous combination of transition metals. In yet another embodiment, the zeolitic framework comprises homogenous transition metal but a heterogeneous combination of linking moieties. In a further embodiment, a zeolitic framework comprises a heterogeneous mixture of transition metals and linking moieties.

In yet another embodiment, the linking moiety comprises a benzimidazolate (bIM) functionalized at the 5 or 4 and 5 positions to modify the pore character and/or cage structure of the framework. The functionalization moiety is used to increase the IM girth and comprises a small electron withdrawing group. The functionalization moiety can comprise, for example, a chloro-, bromo-, iodo-, or fluoro-containing group. For example, the disclosure provides a 5-chlorobenzimidazolate (cbIM) linked to a transition metal selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub. In one aspect, the cbIM linking moiety is linked to a Zn or Co transition metal.

The disclosure provides a functionalized ZIF comprising a tetragonal structure with Zn nodes tetrahedrally coordinated by cbIM having a net referred to as 'poz'. In one aspect, the functionalized ZIF comprises a $[3^{16}4^{28}8^{2}12^{4}]$ poz A cage with 8MR and 12MR faces. In another embodiment, the functionalized ZIF comprises a $[3^{32}4^{36}8^{2}10^{8}12^{4}]$ poz B cage, with 8MR, 10MR and 12MR faces (in the symbols [ ... m'' ... ] means that there are n faces that are m-rings). In further embodiments, the disclosure provides a smaller $[4^{6}10^{4}]$ poz C cages and $[4^{6}]$ poz D cages located at the interstices between A and B cages.

In yet another embodiment, the functionalized ZIF remains intact at temperatures of up to 500° C. A functionalized ZIF of the disclosure can comprise more than about 7500 atoms and diameters of up to about 7 nm.

The disclosure provides zeolitic framework wherein the zeolitic framework comprises a POZ framework structure.

A zeolitic framework on the disclosure can comprise one or more of the following characteristics: a surface area of a pore of the plurality of pores is greater than about 2000 m²/g; a surface area of a pore of the plurality of pores is about 3,000-18,000 m²/g; a surface area of a pore of the plurality of pores is about 3,000-6,000 m²/g; a pore of the plurality of pores comprises a pore volume 0.1 to 0.99 cm³/g; a pore of the plurality of pores comprises a pore volume of 0.4-0.5 cm³/g; a framework density of about 0.17 g/cm³; atomic coordinates as set forth in any one of the tables described herein.

A zeolitic framework on the invention may be interpenetrating. Furthermore, the zeolitic framework of the invention can be used to adsorbed chemical species (e.g., ammonia, carbon dioxide, carbon monoxide, hydrogen, amines, methane, oxygen, argon, nitrogen, argon, organic dyes, polycyclic organic molecules, and combinations thereof). The zeolitic framework on the invention can be used for gas storage, in sensors and as a catalyst.

Also provided are devices for the sorptive uptake of a chemical species. The device includes a sorbent comprising a zeolitic framework (ZIF) provided herein. The uptake can be reversible or non-reversible. In some aspects, the sorbent is included in discrete sorptive particles. The sorptive particles may be embedded into or fixed to a solid liquid- and/or gas-permeable three-dimensional support. In some aspects, the sorptive particles have pores for the reversible uptake or storage of liquids or gases and wherein the sorptive particles can reversibly adsorb or absorb the liquid or gas.

In some embodiments, a device provided herein comprises a storage unit for the storage of chemical species such as ammonia, carbon dioxide, carbon monoxide, hydrogen, amines, methane, oxygen, argon, nitrogen, argon, organic dyes, polycyclic organic molecules, and combinations thereof.

Also provided are methods for the sorptive uptake of a chemical species. The method includes contacting the chemical species with a sorbent that includes a zeolitic framework (ZIF) provided herein. The uptake of the chemical species may include storage of the chemical species. In some aspects, the chemical species is stored under conditions suitable for use as an energy source.

Also provided are methods for the sorptive uptake of a chemical species which includes contacting the chemical species with a device provided described herein.

DESCRIPTION OF DRAWINGS

FIG. 2A-C shows gas adsorption isotherms of ZIF-95 (left) and ZIF-100 (right). (A-B) $N_2$ at 77 K for ZIF-95 (a, left); Ar at 87 K for ZIF-100 (a, right); $CO_2$ (black, circles), $CH_4$ (triangles), CO (diamonds) and $N_2$ (rectangles) at 298K for ZIF-95 (b, left) and ZIF-100 (b, right); the filled and open shapes represent adsorption and desorption, respectively. $P/P_0$, relative pressure at the saturation vapour pressure of the adsorbate gas. (C) Breakthrough curves, $N_2$ (rectangles) and $CO_2$ (black, circles) for ZIF-95 using a $CO_2/N_2$ gas mixture (left); $CH_4$ (triangles) and $CO_2$ (black, circles) for ZIF-100 using a $CO_2/CH_4$ gas mixture (right). The relative intensities of each gas passing through the ZIF-95- and ZIF-100-packed column were obtained using a mass spectrometer to detect ion peaks at m/z 1544 ($CO_2$), 16($CH_4$), 28 ($N_2$) and 12 (CO). Mean value from multiple parallel experiments (n≧3, standard deviation σ≦5% for all isotherms and ≦6% for breakthrough curves) was adopted for each data point. Owing to the slow diffusion, ZIF-100 does not exhibit a stepped isotherm as expected for a mesoporous material.

FIG. 12 show $CO_2$ uptake data for all ZIFs.

FIG. 14 $H_2$ uptake data for all ZIFs.

DETAILED DESCRIPTION

Figure 1A:
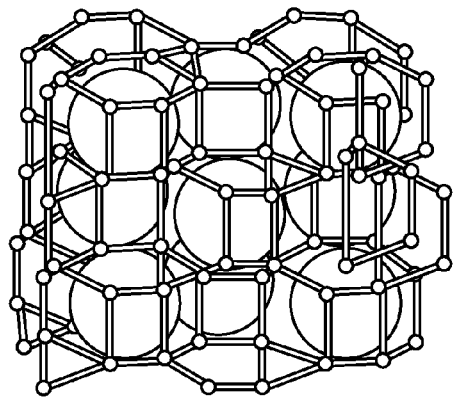
FIG. 1A-E shows the single crystal x-ray structures of ZIFs. (Left and Center) In each row, the net is shown as a stick diagram (Left) and as a tiling (Center). (Right). (B) shows ZIF-95 and -100. (C) The cages in ZIF-95 and ZIF-100. (a) Ball and stick diagrams of the cages in ZIF-95. (b) Structure of poz B cage in ZIF-95; $ZnN_4$ tetrahedra are shown. (c) Space filling diagram of poz B cage in ZIF-95. (d) Ball and stick diagram of moz cage in ZIF-100. (e) Structure of moz cage in ZIF-100. (f) Space filling diagram of moz cage in ZIF-100. All H atoms are omitted for clarity. Note that Cl atoms fill one half of the positions, however the disorder is illustrated here. (D) Bridging angles and girths in zeolites and IMs. (a) $Si_2O$ in zeolites. (b) $Zn_2$(2-methylimidazolate), mIM, in ZIF-8 (structure symbol sod). (c) $Zn_2$ (benzimidazolate), bIM, in ZIF-11 (rho). (d) $Zn_2$(5-chlorobenzimidazolate), cbIM, in ZIF-95 and ZIF-100 (previously unknown topologies). (E) The frameworks as shown as natural tilings of (a) ZIF-95 and (b) ZIF-100.
Figure 1A:
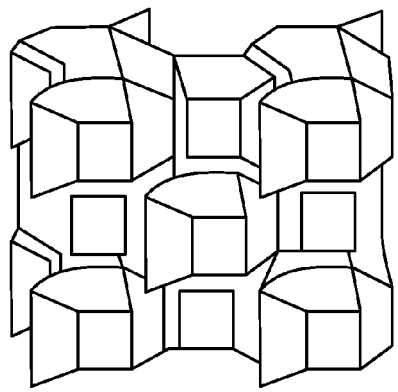
Figure 1A:
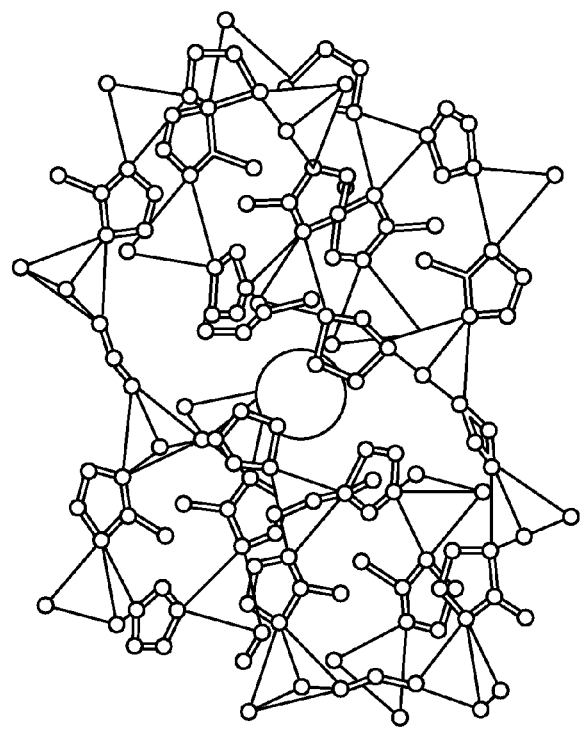
Figure 1A:
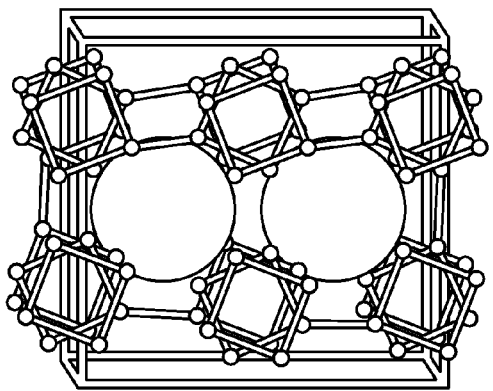
Figure 1A:
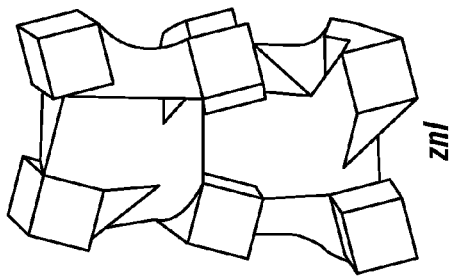
Figure 1A:
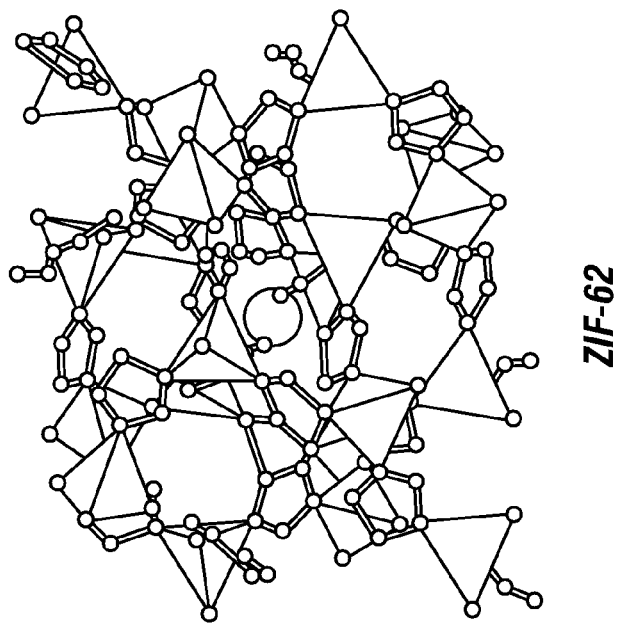
Figure 1A:
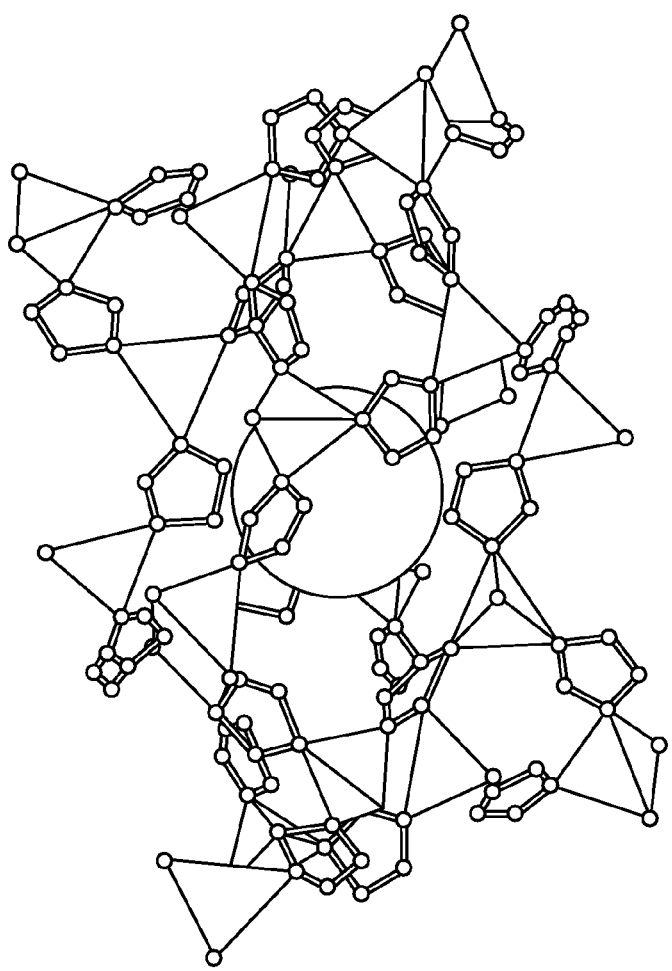
Figure 1A:
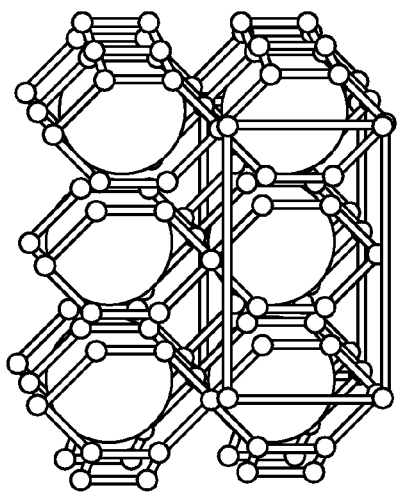
Figure 1A:
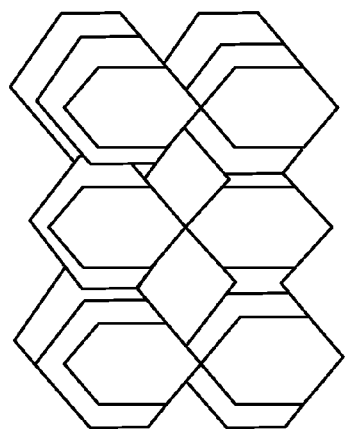
Figure 1A:
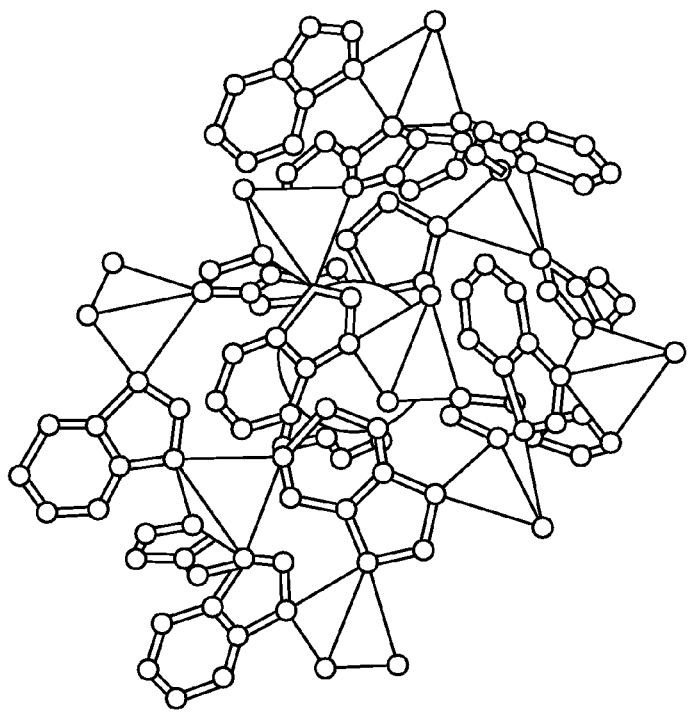
Figure 1A:
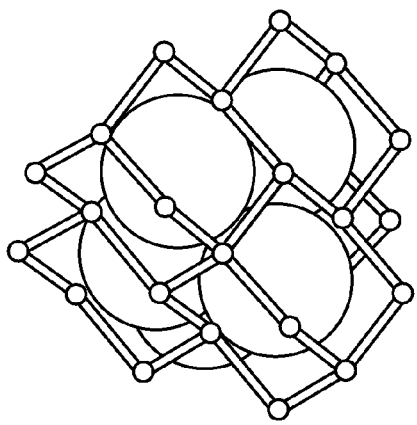
Figure 1A:
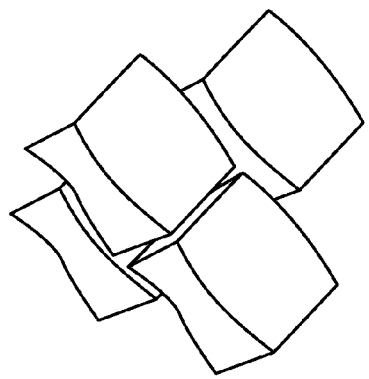
Figure 1A:
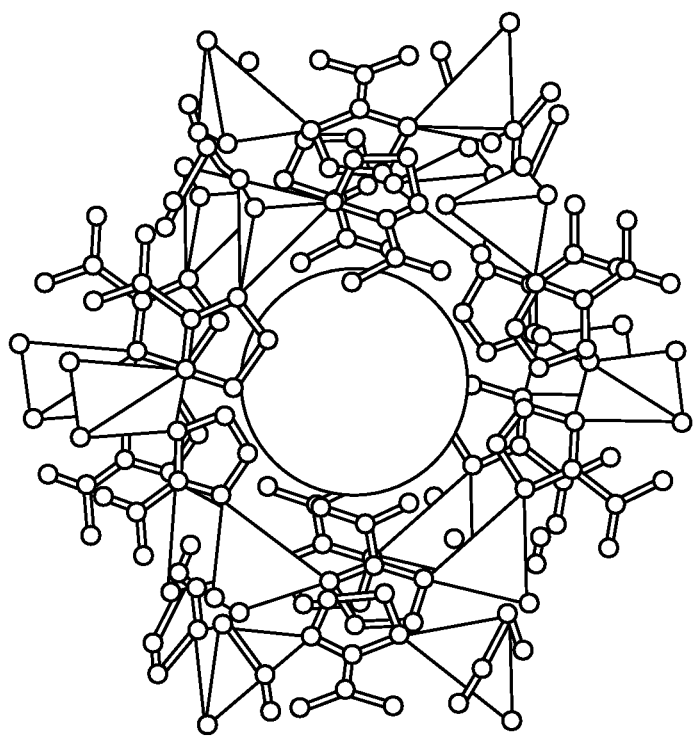
Figure 1A:
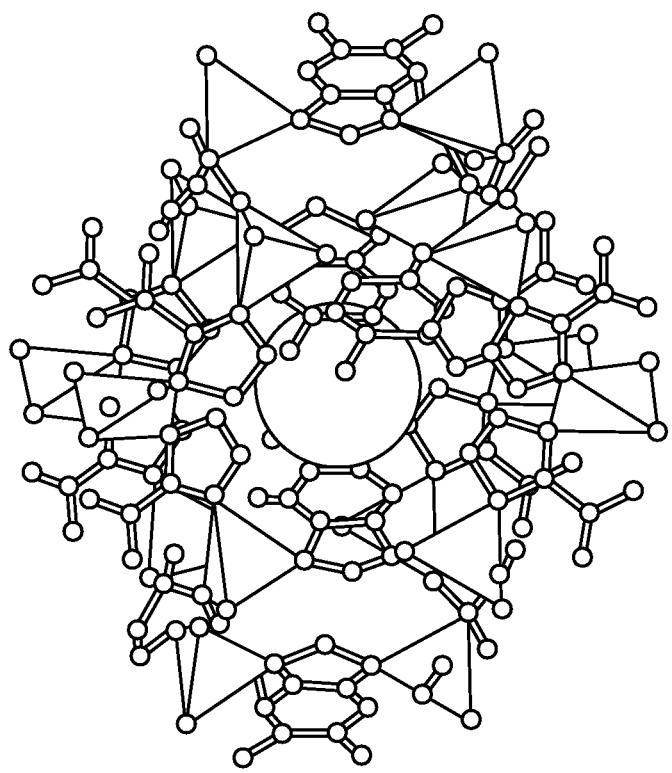
Figure 1A:
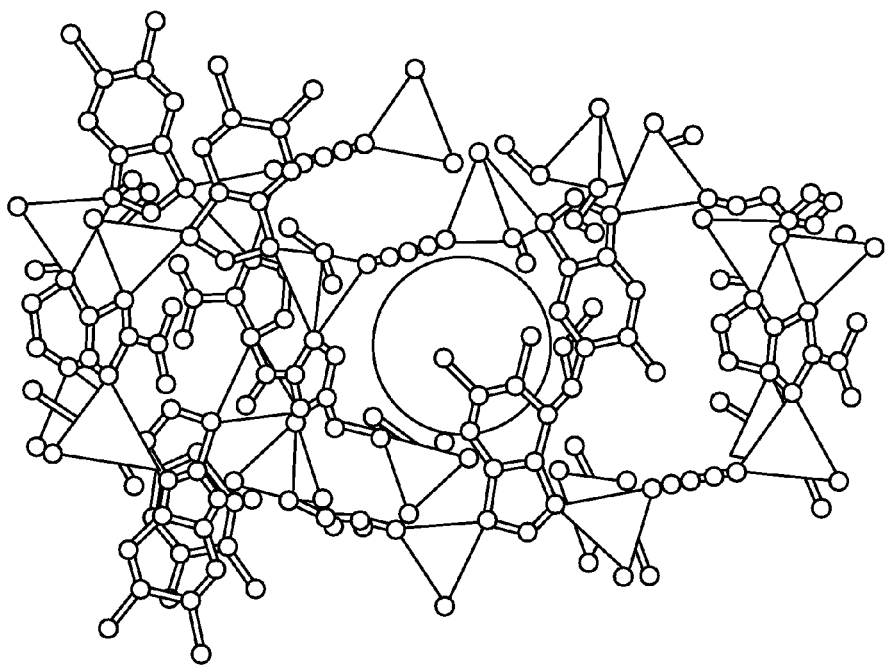
Figure 1A:
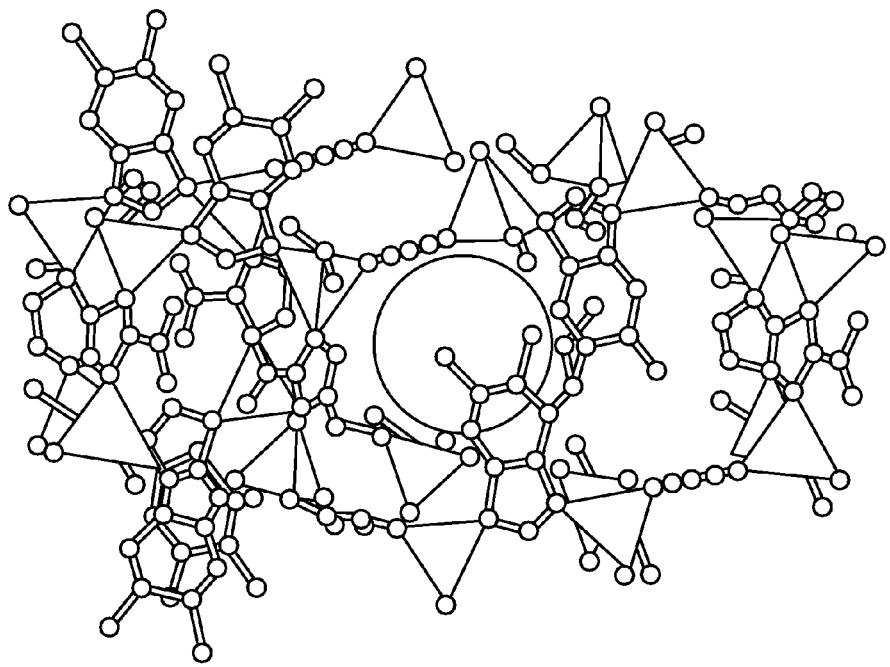
Figure 1A:
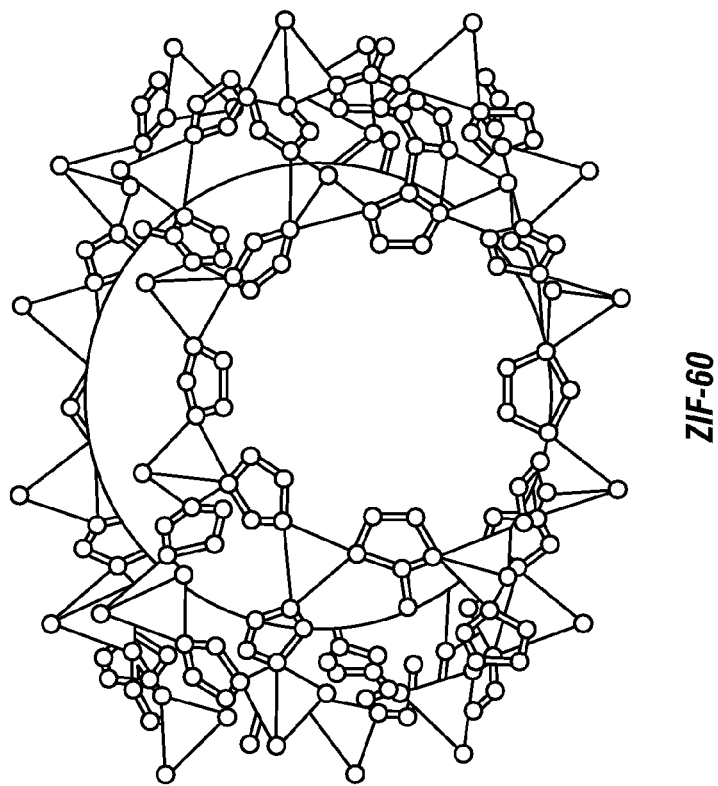
Figure 1A:
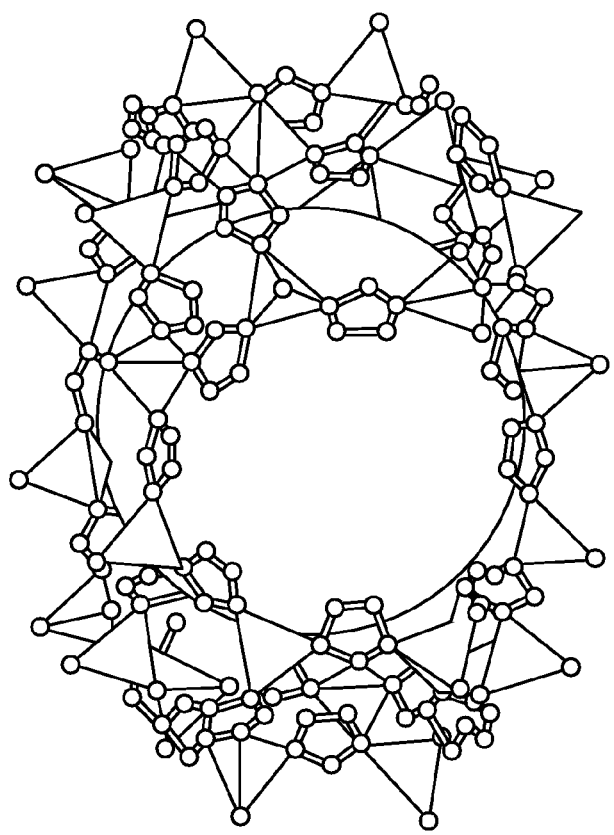
Figure 1A:
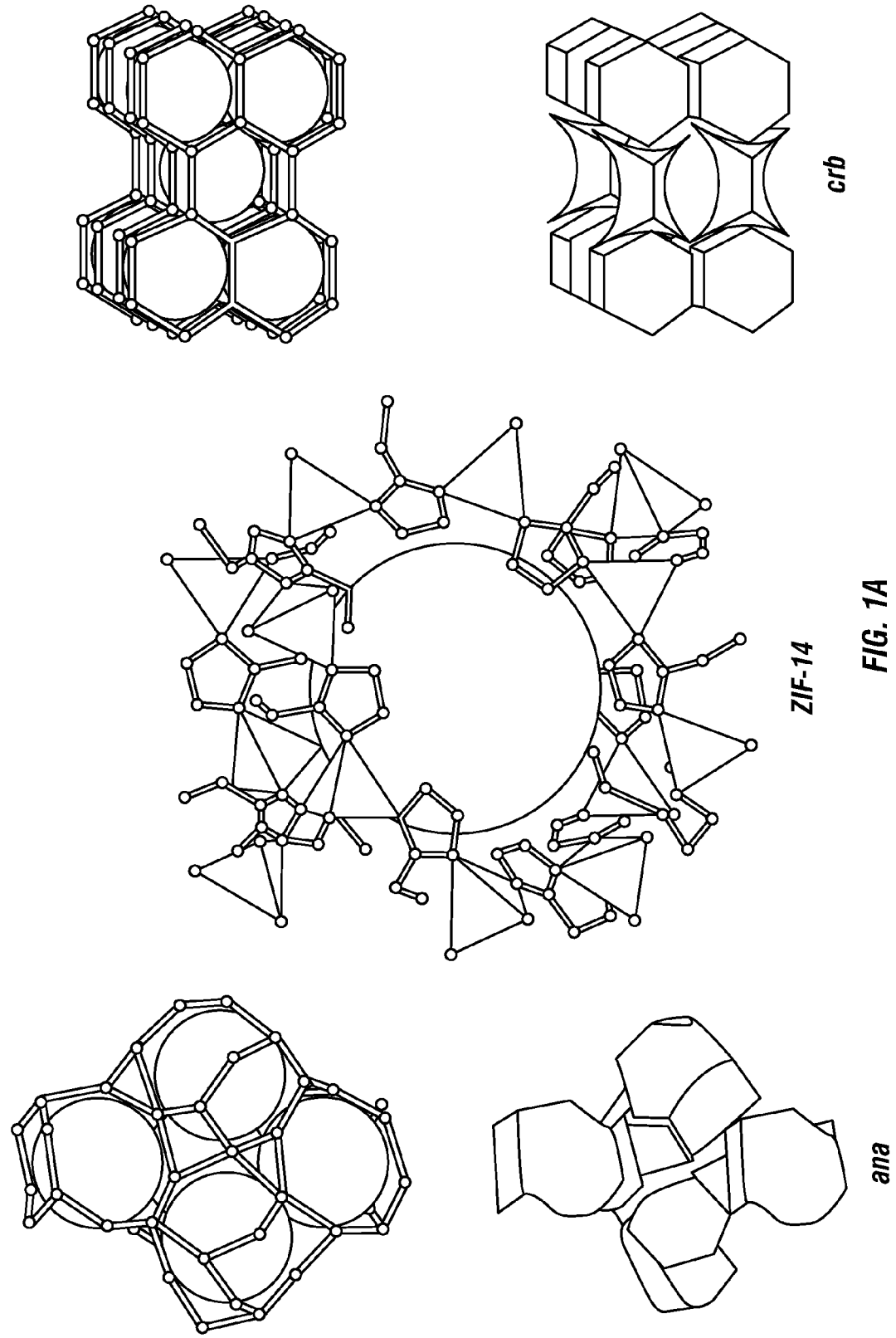
Figure 1A:
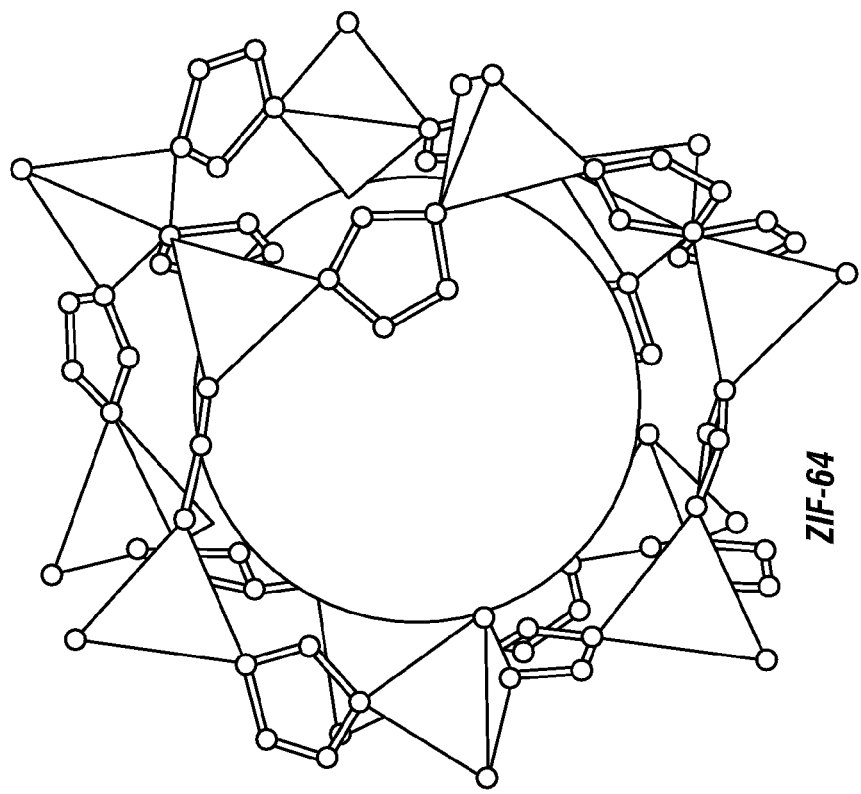
Figure 1A:
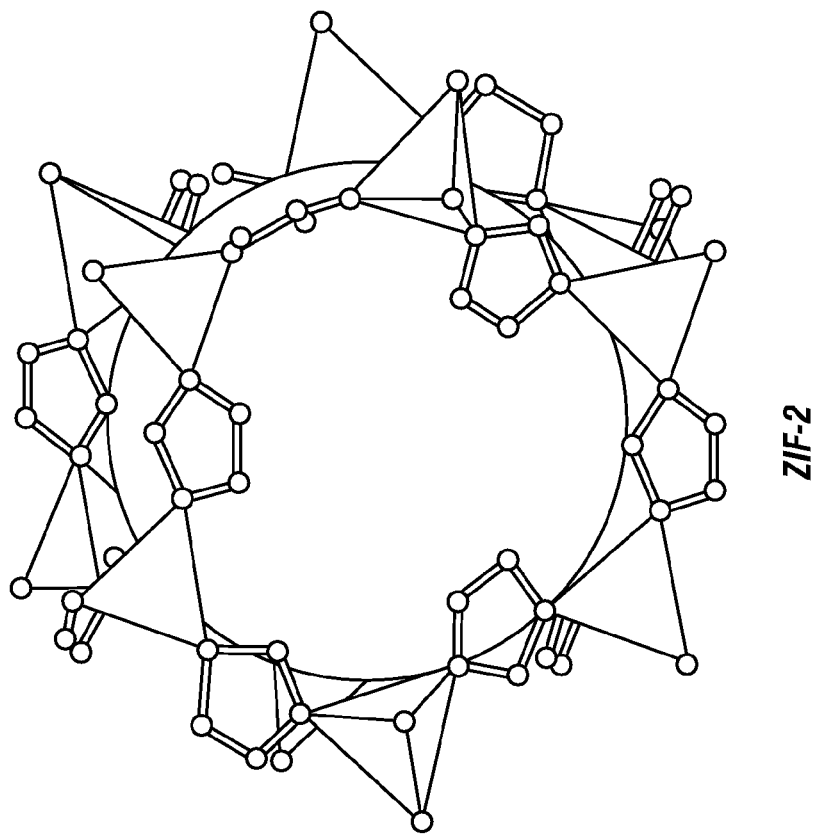

As used herein and in the appended claims, the singular forms "a," "and," and "the" include plural referents unless the context clearly dictates otherwise. Thus, for example, reference to "a pore" includes a plurality of such pore and reference to "the metal" includes reference to one or more metals known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Natural gas is an important fuel gas and it is used extensively as a basic raw material in the petrochemical and other chemical process industries. The composition of natural gas varies widely from field to field. Many natural gas reservoirs contain relatively low percentages of hydrocarbons (less than 40%, for example) and high percentages of acid gases, principally carbon dioxide, but also hydrogen sulfide, carbonyl sulfide, carbon disulfide and various mercaptans. Removal of acid gases from natural gas produced in remote locations is desirable to provide conditioned or sweet, dry natural gas either for delivery to a pipeline, natural gas liquids recovery, helium recovery, conversion to liquefied natural gas (LNG), or for subsequent nitrogen rejection. CO2 is corrosive in the presence of water, and it can form dry ice, hydrates and can cause freeze-up problems in pipelines and in cryogenic equipment often used in processing natural gas. Also, by not contributing to the heating value, CO2 merely adds to the cost of gas transmission.

An important aspect of any natural gas treating process is economics. Natural gas is typically treated in high volumes, making even slight differences in capital and operating costs of the treating unit significant factors in the selection of process technology. Some natural gas resources are now uneconomical to produce because of processing costs. There is a continuing need for improved natural gas treating processes that have high reliability and represent simplicity of operation.

In addition, removal of carbon dioxide from the flue exhaust of power plants, currently a major source of anthropogenic carbon dioxide, is commonly accomplished by chilling and pressurizing the exhaust or by passing the fumes through a fluidized bed of aqueous amine solution, both of which are costly and inefficient. Other methods based on chemisorption of carbon dioxide on oxide surfaces or adsorption within porous silicates, carbon, and membranes have been pursued as means for carbon dioxide uptake. However, in order for an effective adsorption medium to have long term viability in carbon dioxide removal it should combine two features: (i) a periodic structure for which carbon dioxide uptake and release is fully reversible, and (ii) a flexibility with which chemical functionalization and molecular level fine-tuning can be achieved for optimized uptake capacities.

A number of processes for the recovery or removal of carbon dioxide from gas steams have been proposed and practiced on a commercial scale. The processes vary widely, but generally involve some form of solvent absorption, adsorption on a porous adsorbent, distillation, or diffusion through a semipermeable membrane.

The disclosure provides functionalized ZIFs. A functionalized ZIF comprises the general structure M-L-M wherein the transition metals are linked by an imidazolate linker including, for example, an imidazolate linker functionalized by incorporating a group at the 2-position of imidazolate such that the group does not sterically hinder the interaction of a metal (M) with another linker (L). In some embodiments the group at position 2 is an electron donor group such as methyl, or ethyl. A functionalized ZIF further includes a benzimidazolate linker functionalized at the 5 or 4 and 5 positions by a group that does not sterically hinder the formation of a cage structure. In one aspect, the group at position 5 or 4 and 5 is a small electron withdrawing group such as a chloro group. In a further embodiment, the benzimidaolate can be further functionalized at position 2 of the imidazolate.

A long-standing challenge is to incorporate transition metal ions and organic units within their pores and, more desirably, to do so as an integral part of the zeolite framework. This ability would be useful in many catalytic applications because the pores would be lined with a high concentration of ordered transition metal sites whose electronic and steric properties can be tailored by functionalization of the organic links.

Zeolitic frameworks are a class of porous materials that potentially have the advantages both of inorganic zeolites (e.g., high stability) and of MOFs (e.g., high porosity and organic functionality), which could be applied to highly efficient catalysis and separations. From a synthetic perspective, zeolitic framework topologies can be directed by the molecular structure of the organic linker and rationalized by examining the resulting linker-linker interactions in the zeolitic frameworks. The potential difficulty in predicting zeolitic structures, such as is always encountered in zeolite chemistry, can be overcome by further detailing the linker requirements for forming the basic secondary building units (cube in the case LTA) in the structure.

Existing zeolites are crystalline aluminosilicates having ordered channel and cage structures and containing micropores which are typically smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 5th edition, Amsterdam 2001. Specific examples are zeolites having a pentasil structure, in particular the types assigned by X-ray analysis to the ABW, AGO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG and ZON structure and to mixed structures of two or more of the above mentioned structures.

The concept of a default structure (a naturally preferred high-symmetry topology most often adopted by a solid-state material) does not apply directly either to silicates or imidazolate. The 145° angle makes it impossible for the highest symmetry 4-coordinated structure of Fd3m diamond to form; therefore, lower symmetries are invariably found for silicas. Nature prefers $P3_121$ quartz over the $P4_12_12$ cristobalite polymorph, but by only 1 or 2 kJ/mol, and >10 forms of silica are known to be of essentially equal energy (on the scale of bond energies). To reproducibly prepare these and related structures, one needs a structure-directing agent, and this agent is a key to zeolite synthesis. The disclosure shows that structure-directing agents (amide solvent media and linker functionalization) along with control of reaction conditions are effective in achieving a wide variety of zeolitic structures.

The disclosure identifies a strategy to produce imidazolate frameworks in which both the link geometry and link-link interactions play a decisive structure-directing role. The disclosure provides, for example, the synthesis and crystal structures of porous zeolitic structures that are expanded analogues of zeolite A, their cage walls are functionalized, and their metal ions can be changed without changing the underlying LTA topology; these are attributes highly sought after in zeolite chemistry but not before combined in one material.

As used herein, a "core" refers to a repeating unit or units found in a framework. Such a framework can comprise a homogenous repeating core or a heterogeneous repeating core structure. A core comprises a transition metal and a linking moiety. A plurality of cores linked together defines a framework.

A "linking moiety" refers to a mono-dentate or bidentate compound that bind a transition metal or a plurality of transition metals, respectively.

A "zeolitic framework," as used herein, refers to a framework of repeating cores having a zeolite-type structure.

A "zeolitic imidizolate framework" or "ZIF" refers to a zeolitic framework comprising a zeolitic structure having an imidizole, imidizolate-derivative, or imidazolate linking moiety.

The disclosure provides zeolitic frameworks comprising a network of homogenous transition metal or heterogeneous transition metals linked by a homogenous or heterogeneous linking moiety. The zeolitic frameworks of the disclosure can comprise any of the networks currently defined in the Atlas of Zeolite Structure Types known in the literature as well as POZ. The zeolitic frameworks of the disclosure provide nanoporous structure useful for filtration, gas storage and the like, as more fully described herein.

The disclosure also provide a general synthesis of structures having zeolite framework topologies in which all tetrahedral atoms are transition metals, and the linking moieties comprise organic linkers comprising nitrogen, sulfur or oxygen organic molecules (e.g., such as imidazolate (IM) units). The organic linkers may be further functionalized to modify the cage size and pore size or specificity to a guest species or gas molecule.

The compositions of the disclosure comprise a zeolite tetrahedral net comprising a transition metal core and a linking moiety. Useful transition metal comprise any one or more of the following: Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, and Uub. In a specific embodiment, the transition metal is Zn or Co. A linker useful in the zeolite compositions of the disclosure can be selected from the group consisting of structure I, II, III, and any combination thereof:

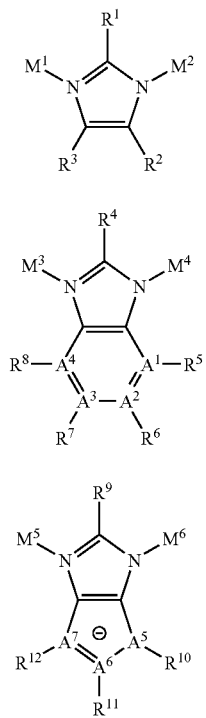

(I)
(II)
(III)

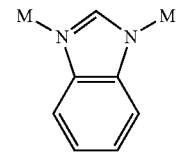
VI

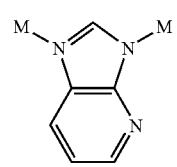
VII

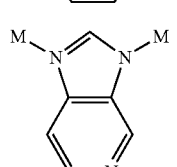
VIII

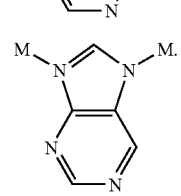
IX wherein A can be either C or N, wherein $R^5$-$R^8$ are present when A1 and A4 comprise C, wherein $R^1$, $R^4$ or $R^9$ comprise a non-sterically hindering group that does not interfere with M, wherein $R^2$, $R^3$, $R^5$, $R^6$, $R^7$, $R^8$, $R^{10}$, $R^{11}$, $R^{12}$ are each individually an alkyl, halo-, cyano-, or nitro-, wherein when the linking moiety, comprises structure III, $R^{10}$, $R^{11}$ and $R^{12}$ are each individually electron withdrawing groups. In one embodiment $R^1$, $R^4$ and $R^9$ are individually small groups selected from the group consisting of H, methyl-, halo-, cyano-, and ethyl-. In another embodiment, $R^{10}$, $R^{11}$ and $R^{12}$ are each individually selected from the group consisting of a nitro-, cyano-, fluoro- and chloro-group. In one embodiment, the linking moiety is an imidazolate or an imidazolate derivative.

In one embodiment, $R^1$, $R^4$ or $R^9$ comprise a non-sterically hindering electron donating group that does not interfere with M. The $R^1$, $R^4$ or $R^9$ functionalized with a group selected to interact with a particular gas or substrate. In another embodiment, $R^2$, $R^3$, $R^6$, $R^7$, or $R^{11}$ are individually H or a small electron withdrawing group. In one aspect, the small electron withdrawing group is of sufficient size to increase a cage size for a ZIF of the disclosure. For example, $R^7$ can be a chlorogroup.

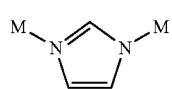
IV

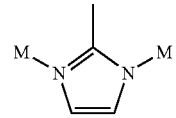
V

For example, heterocyclic rings including imidazolate compounds and derivative such as substituted imidazolate, benzimidazolate, methyl-, nitro-, cyano, or chloro-groups, azabenzimidazolate, azabenzimidazolte wherein one or two carbon atoms on the benzimidazolate are replaced by nitrogen and the like can be used.

The zeolitic framework (e.g., a ZIF) of the disclosure can take any framework/structure. For example, using the methods of the disclosure, ZIFs having any of the following framework codes can be obtained: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EON, EPI, ERI, ESV, ETR, EUO, EZT, FAR, FAU, FER, FRA, GIS, GIU, GME, GON, GOO, HEU, IFR, IHW, ISV, ITE, ITH, ITW, IWR, IWV, IWW, JBW, KFI, LAU, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, and ZON A transition metal and linking moiety core have been used to generate a plurality of zeolitic frameworks. For example, zeolitic imidazolate frameworks (ZIFs) have been synthesized as crystals by copolymerization of transition metals with imidazolate-type links. The ZIF crystal structures are based on the nets of a plurality of distinct aluminosilicate zeolites: tetrahedral Si(Al) and the bridging O are replaced with transition metal ion and an imidazolate link, respectively. Study of the gas adsorption and thermal and chemical stability of the ZIFs demonstrated their porosity (Langmuir surface area of about 1,810 m$^2$/g), high thermal stability (up to 550° C.), and remarkable chemical resistance to boiling alkaline water and organic solvents.

Imidazole, for example, can lose a proton to form IM. The core of such frameworks can be formulated T(Im)$_2$ (Im=imidazolate and its derivatives, T=tetrahedrally bonded metal ion) and are similar to the (Al)SiO$_2$ frameworks of (alumino)silicate zeolites; in particular the T-Im-T angle of about 145° is close to the Si—O—Si angle typically found in zeolites In examining the dense-phases Co(IM)2 and Zn(IM)2, whose structures are based on nets of linked CoN$_4$ or ZnN$_4$ tetrahedra, the angle is as depicted in Scheme 1 and FIG. 1D for various ZIFs of the disclosure.

Scheme I

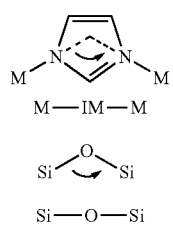

The disclosure provides a general strategy that has led to zeolitic structures based on other zeolite nets. The disclosure confirms the porosity of ZIFs of the disclosure and unlike other metal-organic compounds, the zeolitic frameworks (ZIFs) have exceptional chemical stability in refluxing organic solvents, water, and aqueous alkaline solution. These results point to the potential applications and rich structural diversity of this class of porous materials.

A zeolitic framework of the disclosure, such as a ZIF, can be synthesized by using solvothermal methods. Highly crystalline materials were obtained by combining the requisite hydrated metal salt (e.g., nitrate) and imidazole-type linker in an amide solvent such as N,N-diethylformamide (DEF). The resulting solutions were heated (85-150° C.) and zeolitic frameworks of the disclosure where precipitated after 48-96 h and were readily isolated. Single crystals suitable for x-ray structure analysis were selected from the precipitate. FIG. 1 illustrates examples of precipitated structures. In FIG. 1, the metal center of each structure is coordinated by the N atoms of IM to give overall neutral frameworks. The five-membered IM ring, as depicted in FIG. 1, serves as the bridging/linking unit between the transition metal centers and imparts angle 1 of ~145° throughout the frameworks via coordinating N atoms in the 1,3-positions of the ring. The organic components of the zeolitic framework provides organically lined cages and channels rather than a silicate oxide surface as in prior zeolites. It a further aspect, the imidazolate structures or derivatives can be further functionalized to impart function groups that line the cages and channel, and particularly the pores to obtain a desired structure or pore size.

For example, a general ZIF reaction comprises one or two of formula I-IX, above, IM-type links, which are reacted with a metal (e.g., either zinc(II) nitrate or cobalt(II) nitrate in N,N'-dimethylformamide or N,N'-diethylformamide. The metal-to-linker mole ratio can range from about 1:1 to 1:12. These amounts can be dispensed with an automated dispensing unit charged with a stock solution whose concentration can also be varied from 0.075 to 0.20 M for both reactants. After loading the mixture of reactants into a reaction vessel, the reaction vessels were covered with a polytetrafluoroethylene sheet, sealed, and then heated to a temperature range of 65° to 150° C. for 48 to 100 hours. Crystalline products of ZIFs were obtained in this temperature range. Using data, the concentration, temperature and reaction time can be adjusted. For example, a concentration level of 0.20 M, a reaction time of 72 hours, and an isothermal temperature of 85° or 100° C. are optimal for some ZIF syntheses and crystallization.

In addition to ZIF-95 and ZIF-100, twenty-five different crystals using this protocol for single-crystal structural characterization were obtained (see, e.g., Table A).

TABLE A

The ZIFs discovered by high-throughput synthesis.

| ZIF-n | Composition | Net (18) | Zeolite (15) | T/V (nm$^{-3}$) | $d_a$ (Å) | $d_p$ (Å) | N† | Transitivity | Cage |
|---|---|---|---|---|---|---|---|---|---|
| 2 | Zn(IM)$_2$ | crb | BCT | 2.80 | 6.4 | 6.9 | 12 | 1232 | [6$^2$ · 8$^2$] |
| 3* | Zn(IM)$_2$ | dft | DFT | 2.66 | 4.6 | 6.0 | 16 | 1353 | [6$^2$ · 8$^4$] |
| 4 | Zn(IM)$_2$ | cag | — | 2.04 | 2.0 | 2.1 | 20 | 1431 | [4$^2$ · 6$^8$] |
| 8 | Zn(mIM)$_2$ | sod | SOD | 2.47 | 3.4 | 11.6 | 24 | 1121 | [4$^6$ · 6$^8$] |
| 10 | Zn(IM)$_2$ | mer | MER | 2.25 | 8.2 | 12.1 | 24 | 1463 | [4$^{12}$ · 8$^6$] |
| 11 | Zn(bIM)$_2$ | rho | RHO | 2.01 | 3.0 | 14.6 | 48 | 1242 | [4$^{12}$ · 6$^8$ · 8$^6$] |
| 12 | Co(bIM)$_2$ | rho | RHO | 2.01 | 3.0 | 14.6 | 48 | 1242 | [4$^{12}$ · 6$^8$ · 8$^6$] |
| 14 | Zn(eIM)$_2$ | ana | ANA | 2.47 | 2.2 | 2.2 | 24 | 1132 | [6$^2$ · 8$^3$] |
| 20 | Zn(Pur)$_2$ | lta | LTA | 2.04 | 2.8 | 15.4 | 48 | 1343 | [4$^{12}$ · 6$^8$ · 8$^6$] |
| 21 | Co(Pur)$_2$ | lta | LTA | 2.03 | 2.8 | 15.4 | 48 | 1343 | [4$^{12}$ · 6$^8$ · 8$^6$] |
| 23* | Zn(abIM)$_2$ | dia | — | 3.31 | 1.1 | 4.2 | 10 | 1111 | [6$^4$] |
| 60 | Zn(IM)$_{1.5}$(mIM)$_{0.5}$ | mer | MER | 2.24 | 7.2 | 9.4 | 24 | 1463 | [4$^{12}$ · 8$^6$] |
| 61 | Zn(IM)(mIM) | zni | — | 4.62 | 0.7 | 0.7 | 20 | 1342 | [6$^3$ · 12$^2$] |
| 62 | Zn(IM)$_{1.75}$(bIM)$_{0.25}$ | cag | — | 3.52 | 1.4 | 1.3 | 20 | 1431 | [4$^2$ · 6$^8$] |
| 64 | Zn(IM)$_2$ | crb | BCT | 3.62 | 2.5 | 7.9 | 12 | 1232 | [6$^2$ · 8$^2$] |
| 65 | Co(nIM)$_2$ | sod | SOD | 2.32 | 3.4 | 10.4 | 24 | 1121 | [4$^6$ · 6$^8$] |
| 67 | Co(mIM)$_2$ | sod | SOD | 2.46 | 3.4 | 11.6 | 24 | 1121 | [4$^6$ · 6$^8$] |
| 68 | Zn(bIM)(nIM) | gme | GME | 2.12 | 7.5 | 10.3 | 24 | 1463 | [4$^6$ · 8$^3$ · 12$^2$] |
| 69 | Zn(cbIM)(nIM) | gme | GME | 2.09 | 4.4 | 7.8 | 24 | 1463 | [4$^6$ · 8$^3$ · 12$^2$] |
| 70 | Zn(Im)$_{1.13}$(nIM)$_{0.87}$ | gme | GME | 2.10 | 13.1 | 15.9 | 24 | 1463 | [4$^6$ · 8$^3$ · 12$^2$] |
| 71 | Zn(dcIM)$_2$ | rho | RHO | 2.06 | 4.2 | 16.5 | 48 | 1242 | [4$^{12}$ · 6$^8$ · 8$^6$] |
| 72 | Zn(dcIM)$_2$ | lcs | — | 3.16 | 1.9 | 1.9 | 12 | 1121 | [6$^5$] |
| 73 | Zn(nIM)$_{1.74}$(mbIM)$_{0.26}$ | frl | — | 3.20 | 1.0 | 1.0 | 16 | 2342 | [4$^4$ · 6$^2$ · 8$^2$] |
| 74 | Zn(nIM)(mbIM) | gis | GIS | 2.66 | 1.2 | 2.6 | 20 | 1231 | [4$^6$ · 8$^4$] |
| 75 | Co(nIM)(mbIM) | gis | GIS | 2.66 | 1.2 | 2.62 | 20 | 1231 | [4$^6$ · 8$^4$] |

TABLE A-continued

The ZIFs discovered by high-throughput synthesis.

| ZIF-n | Composition | Net (18) | Zeolite (15) | T/V (nm$^{-3}$) | $d_a$ (Å) | $d_p$ (Å) | N† | Transitivity | Cage |
|---|---|---|---|---|---|---|---|---|---|
| 76 | Zn(IM)(cbIM) | lta | LTA | 2.05 | 5.4 | 12.2 | 48 | 1343 | [$4^{12} \cdot 6^8 \cdot 8^6$] |
| 77 | Zn(nIM) | frl | — | 3.22 | 2.9 | 3.6 | 16 | 2342 | [$4^4 \cdot 6^2 \cdot 8^2$] |

Dashes indicate no zeolite symbol.

Three (ZIF-68 to 70) have structures based on a zeolite topology (gme) and five have tetrahedral topologies (dia, cag, frl, lcs, and zni). The nets of the structures are denoted by a bold lowercase three-letter symbol that is often the same as that of the corresponding zeolite net. Furthermore, 10 structures (ZIF-60 to 62, 68 to 70, and 73 to 76) contain two chemically different imidazolate links (i.e., heterolinks).

The existence of two different types of IMs with a side chain (e.g., an $NO_2$ or a $CH_3$ group) or an aromatic ring on the link makes the pore heterogeneously functionalized across the series (FIG. 1). Furthermore, the diameter of the sphere that will pass through that pore (da) ranges from as low as 0.7 Å to as high as 13.1 Å, whereas the diameter of the sphere that will fit into the cavities (dp) varies from 0.7 to 15.9 Å. With the exception of ZIF-69, 71, 72, and 77, H atoms are nearest to the center of the cavity, and a van der Waals radius of 1.2 Å for H was used in determining the appropriate sphere size.

For ZIF-69, 71, 72, and 77, where the atoms nearest to the center of the cages are either Cl (69, 71, and 72) or O (77), van der Waals radii of 1.8 Å (Cl) and 1.5 Å (O) were used. The values of da and dp provide a lower limit to the cage volume because, in some cases, the cages are ellipsoidal. The number of vertices of the largest cage in each structure ranges from 10 (dia) to 48 (lta). The cage face symbol (in which [ ... n$^m$ ... ] signifies that the cage has m faces that are n rings) and the transitivities of the nets are given in Table, above.

Figure 1B:
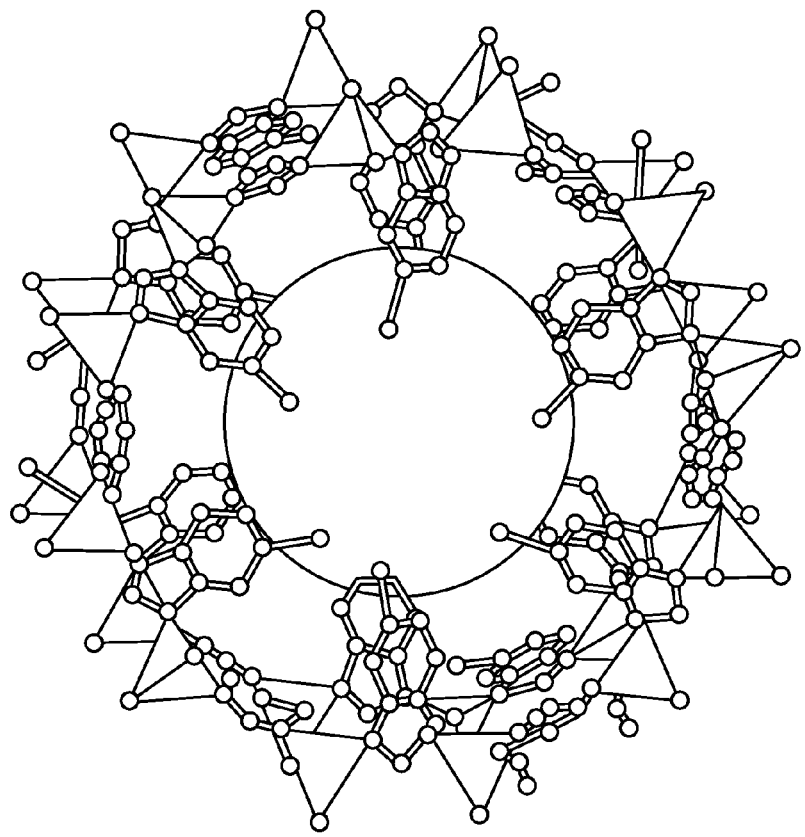
Figure 1B:
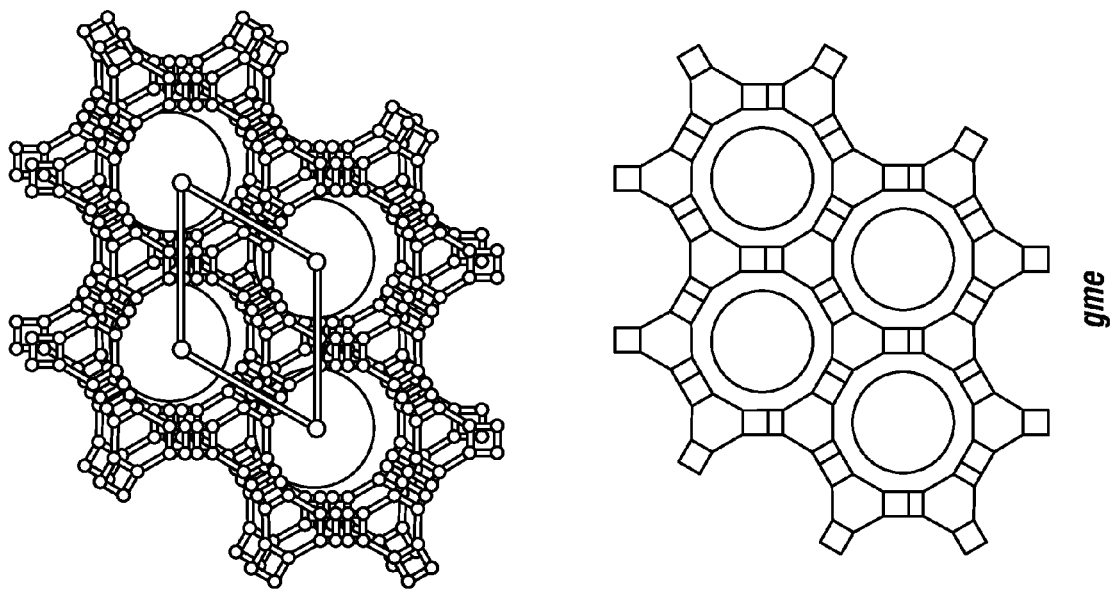
Figure 1B:
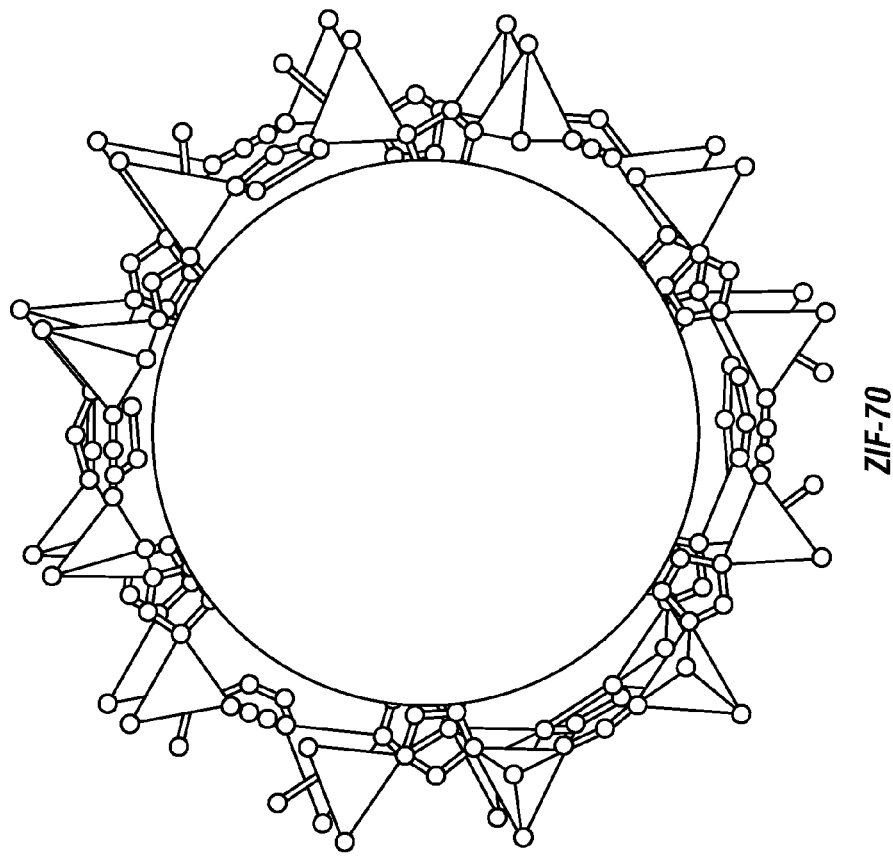
Figure 1B:
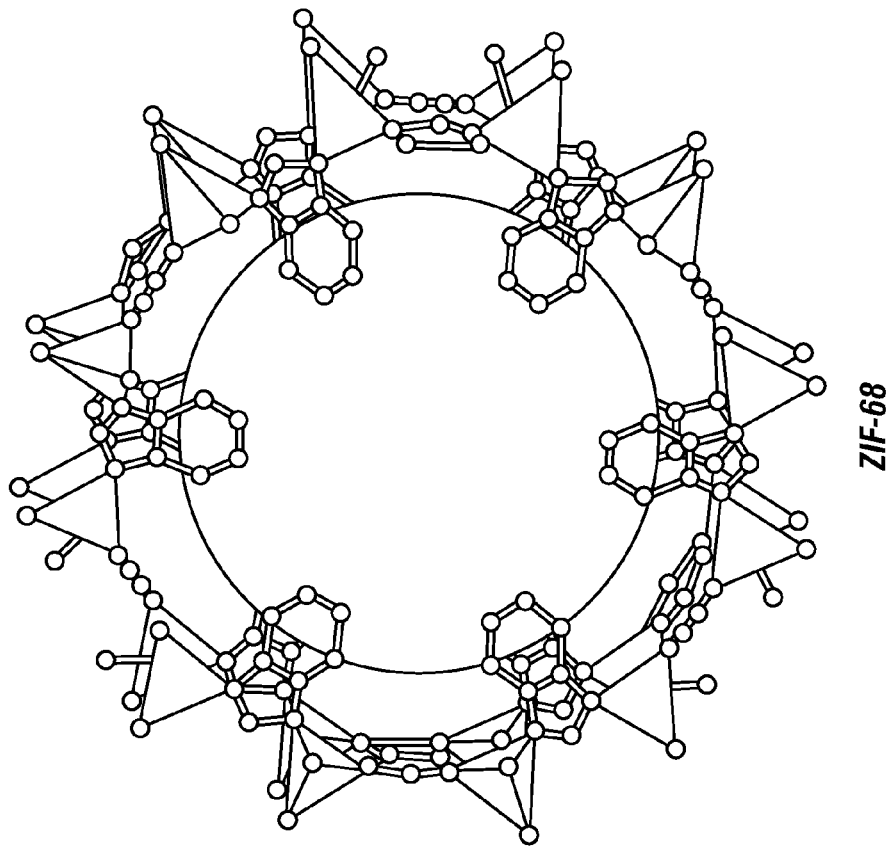
Figure 1B:
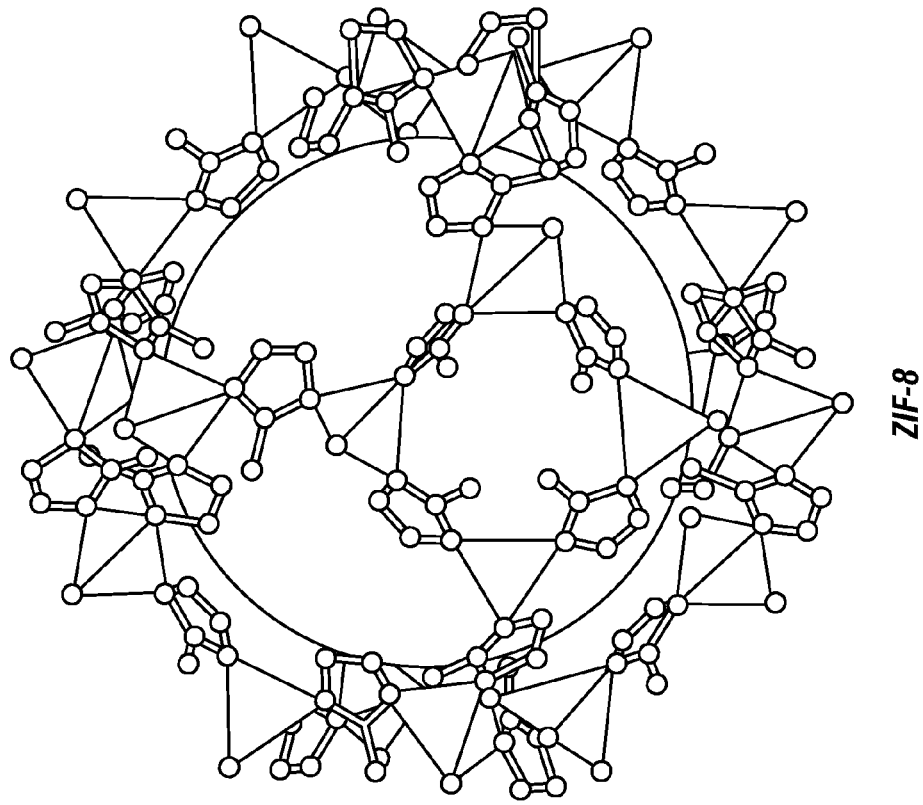
Figure 1B:
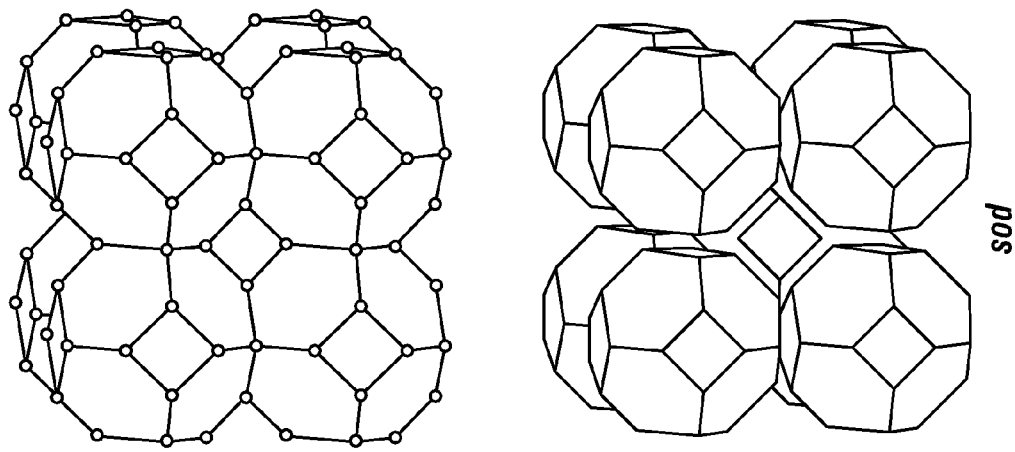
Figure 1B:
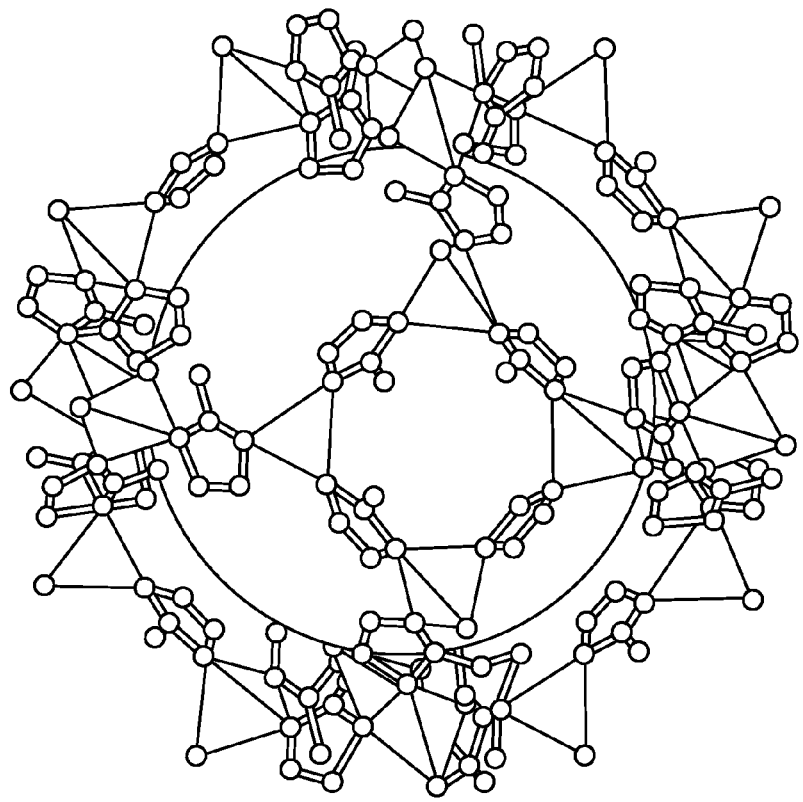
Figure 1B:
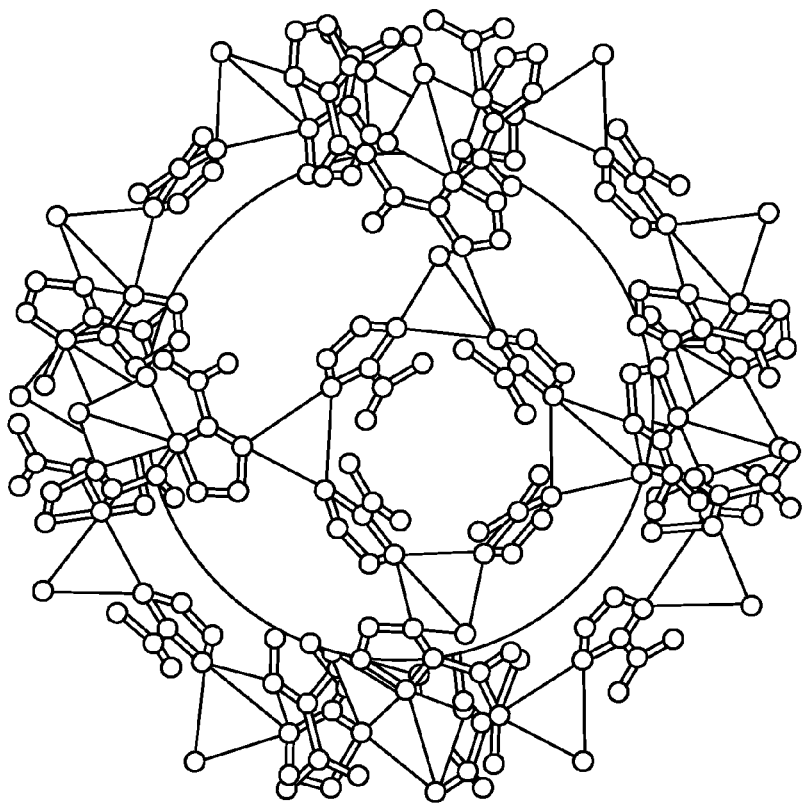
Figure 1B:
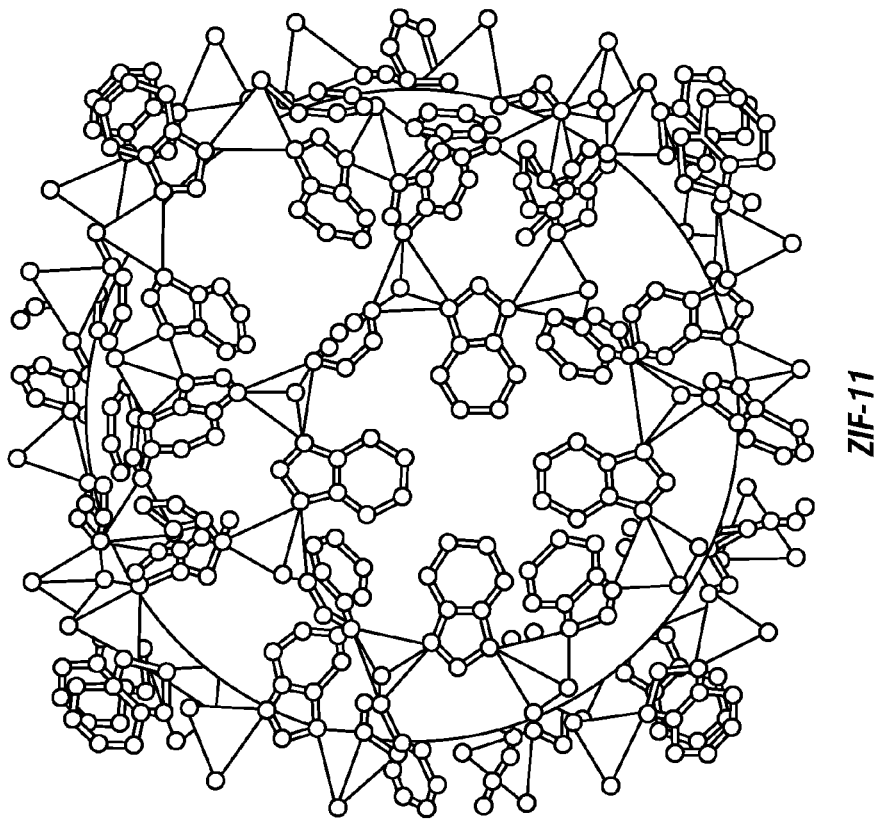
Figure 1B:
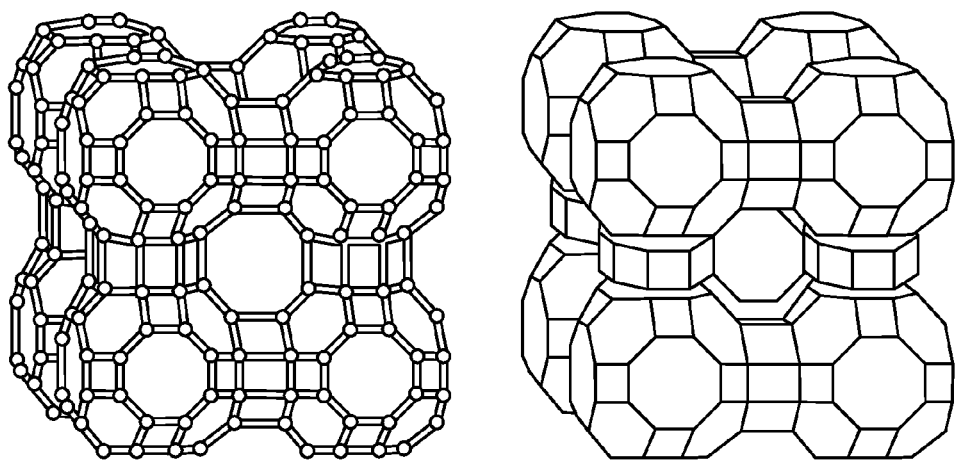
Figure 1B:
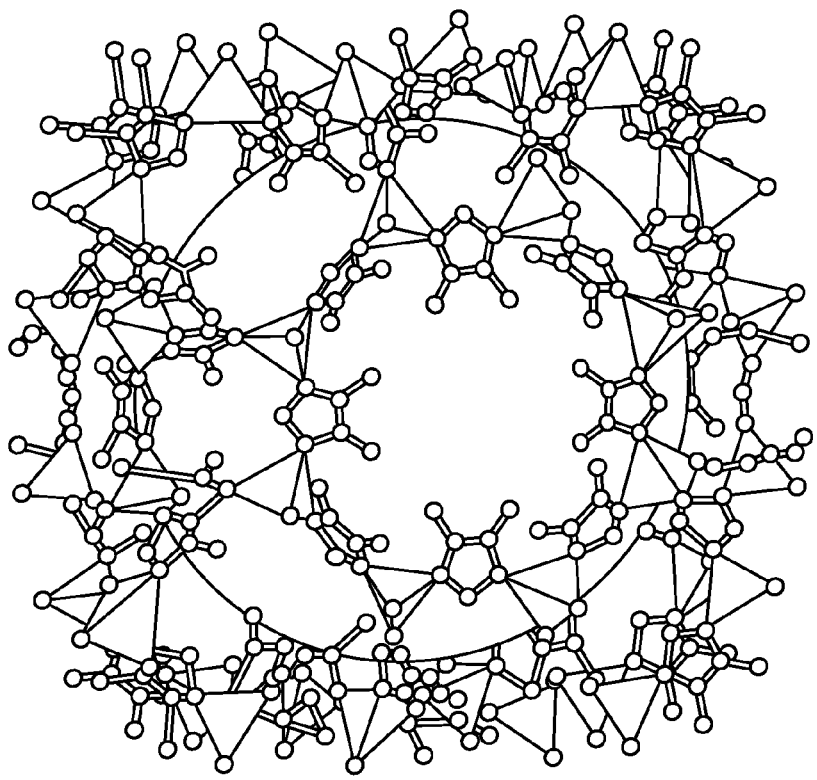
Figure 1B:
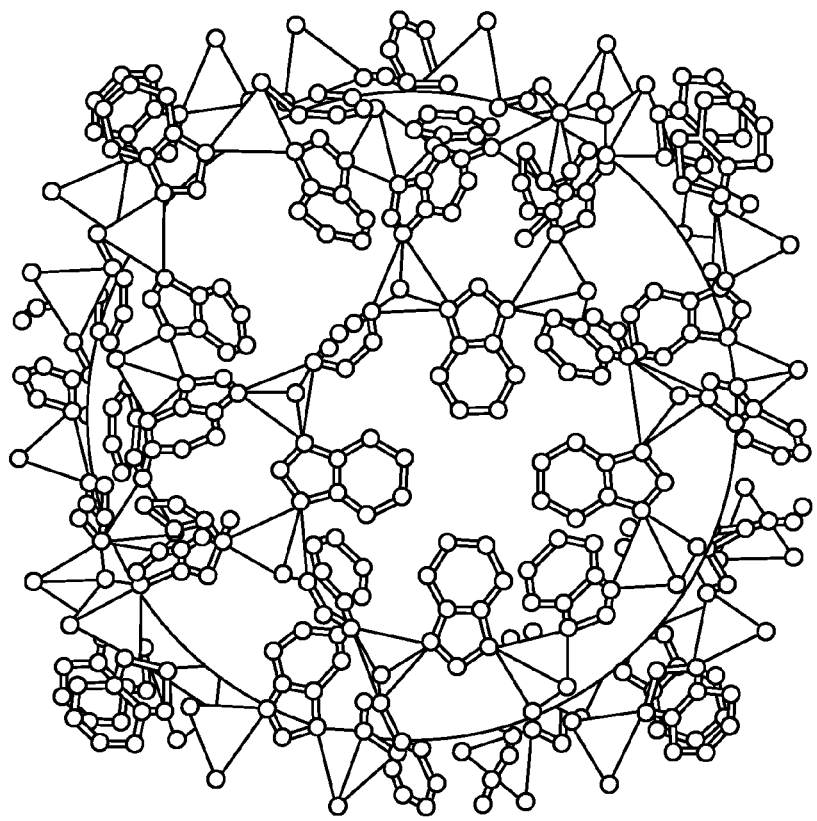
Figure 1B:
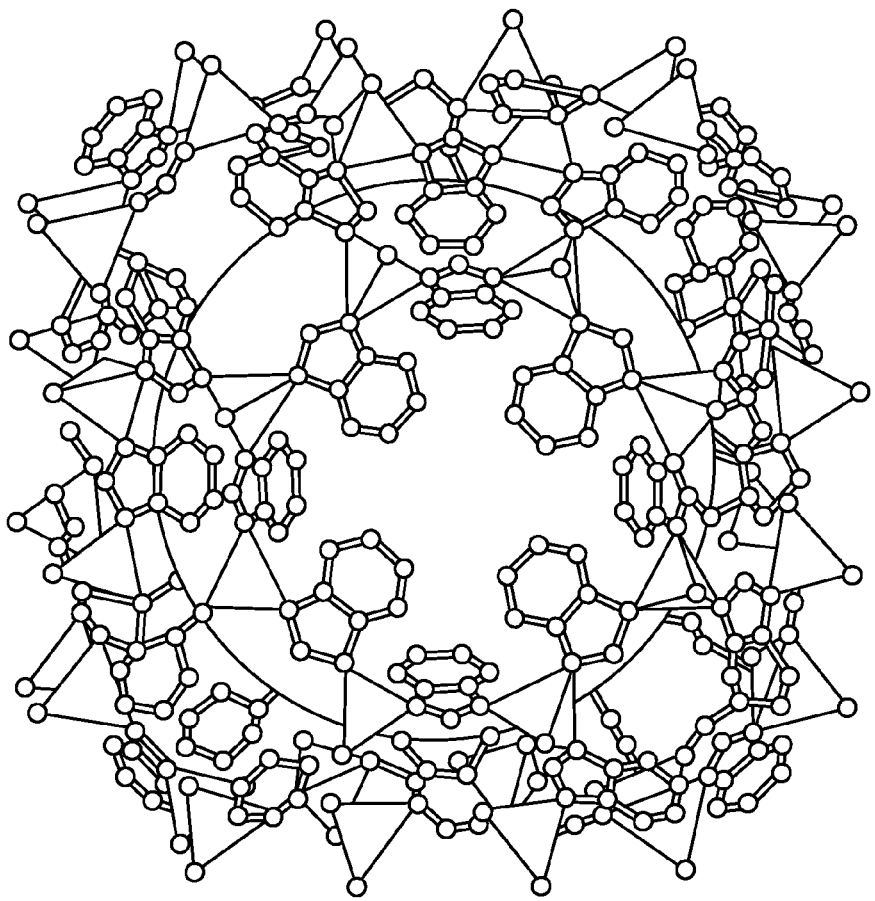
Figure 1B:
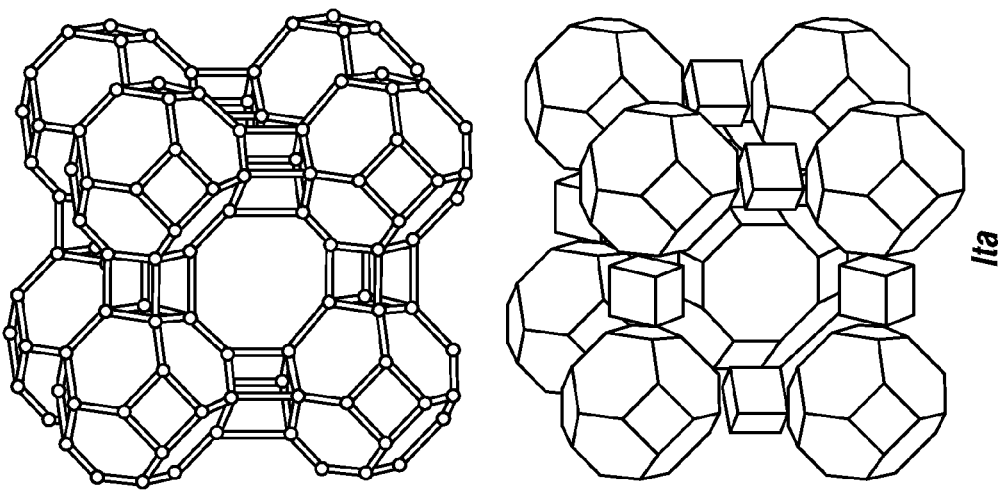
Figure 1B:
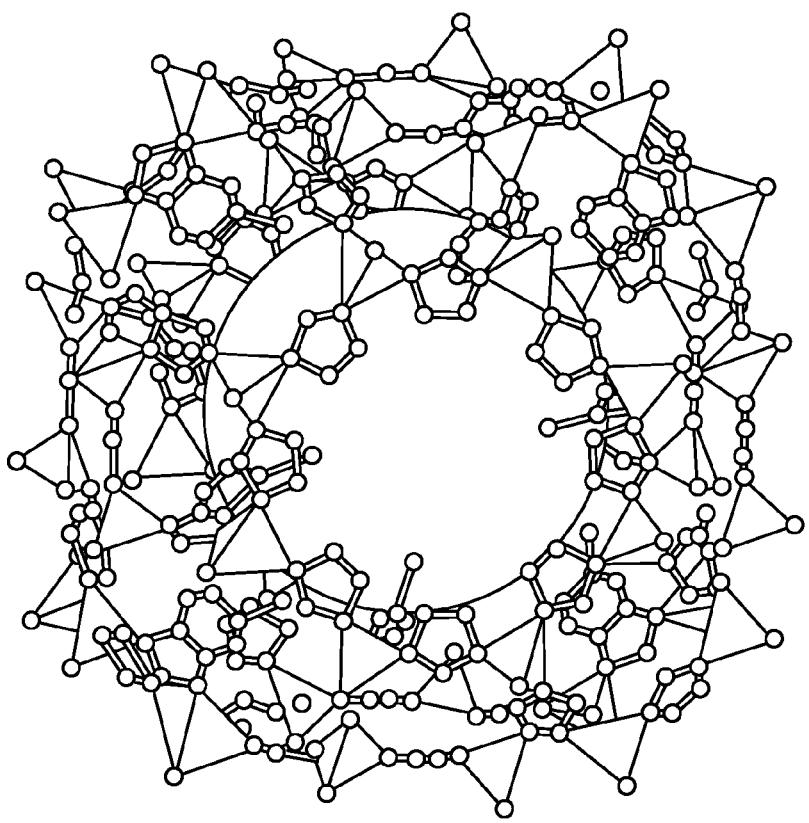
Figure 1B:
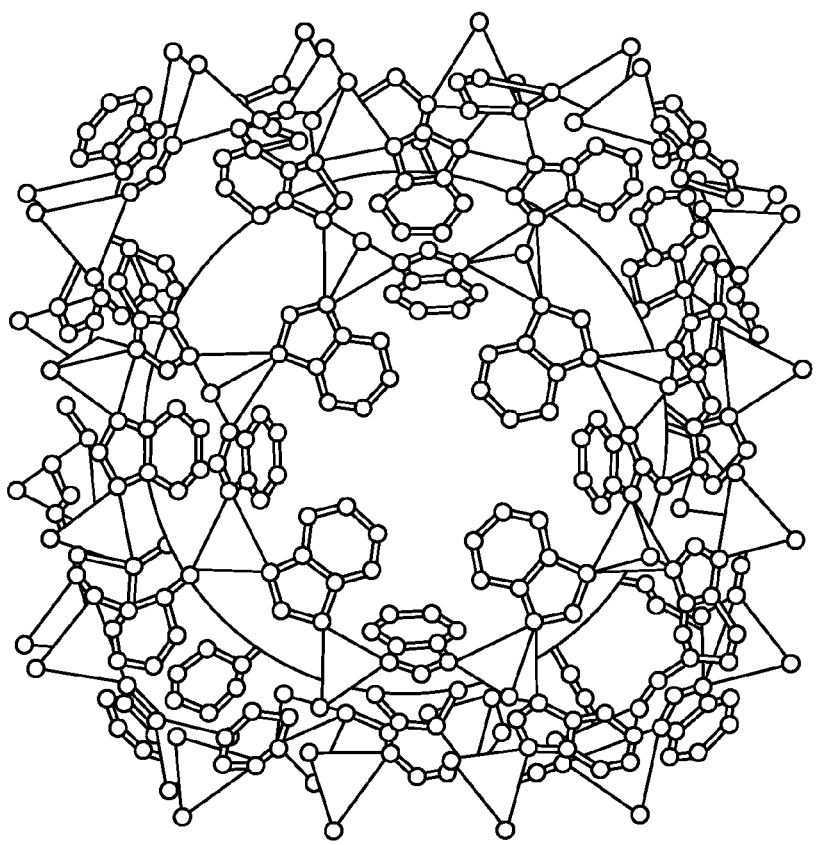
Figure 1C:
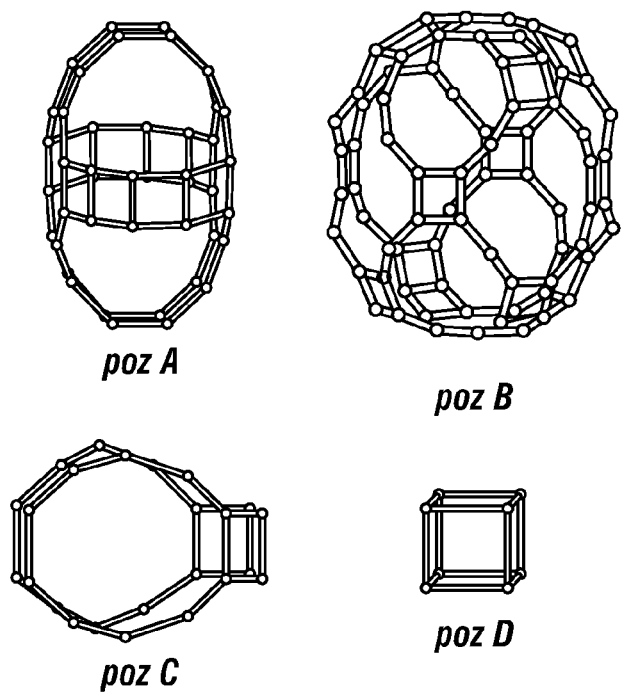
Figure 1C:
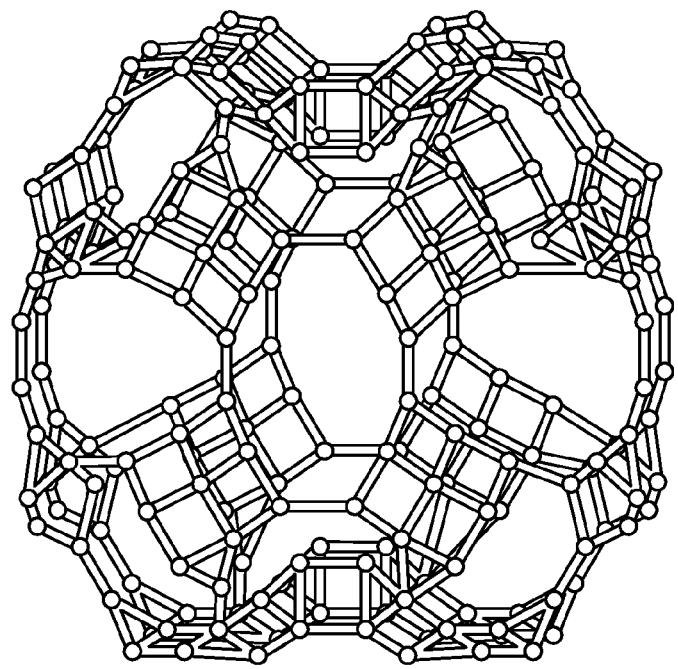
Figure 1C:
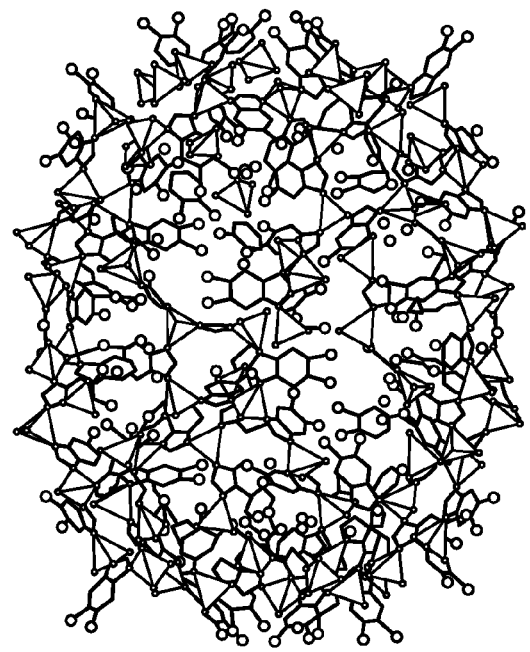
Figure 1C:
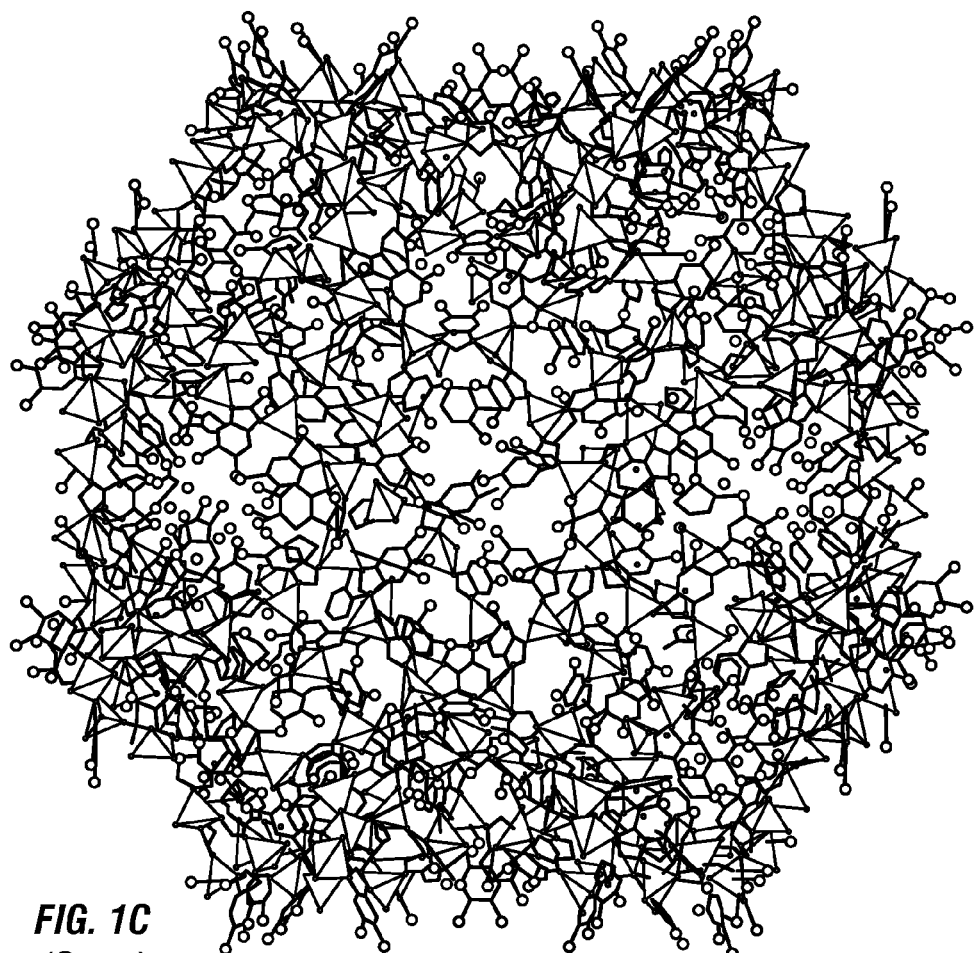
Figure 1C:
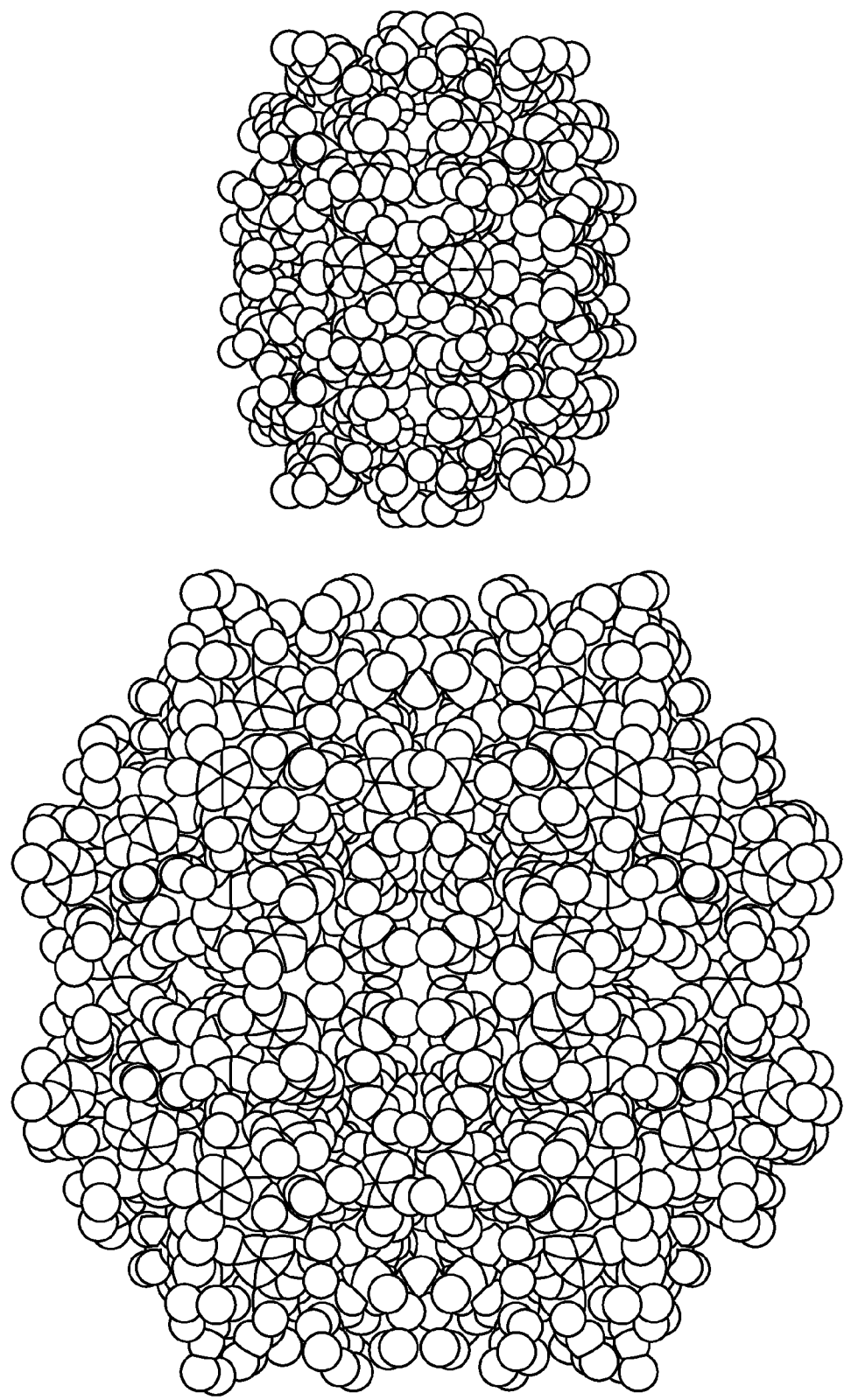

In some of the ZIFs described herein, a Zn or Co atom is connected to four IM or substituted IM linkers to create a corresponding tetrahedron (FIG. 1A-B). The tetrahedra are linked by corner-sharing into different three-dimensional zeolitic frameworks. However, these ZIFs differ in the nature of the functional groups decorating the pores and in the metrics of their pore structure. Across the series, the metrics are systematically varied in increments of less than 1 Å; such tunability is unusual and useful in gas adsorption and separation.

Figure 1D:
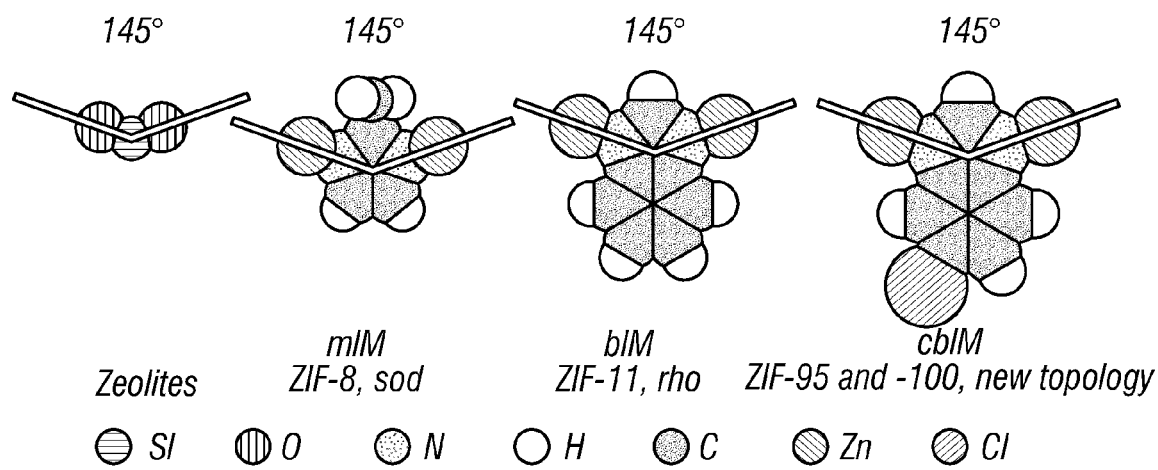

Introduction of greater structural diversity can be obtained by functionalization of IM linkers. In fact, it has been shown that link-link interactions can direct the formation of specific ZIF structures. For example, 2-methylimidazolate (mIM) and benzimidazolate (bIM), which form ZIF-8 and ZIF-11, and modelling studies of sod and rho type structures, indicated that functionalization of the 6-membered ring (6MR) at the 4 or 5 position of bIM overcrowds links and inhibits the formation of rho (FIG. 1D-d). By functionalizing the 6MR with an electron withdrawing group such as a chloro-group (e.g., 5-chlorobenzimidazolate (cbIM)) increases the IM girth (FIG. 1).

Using such methodology ZIF-95 was synthesized and structurally characterized by X-ray diffraction, and was found to be tetragonal. It has a neutral framework with all Zn nodes tetrahedrally coordinated by cbIM. The 4-coordinated net of linked Zn atoms has a topology we name 'poz'. Salient features of the structure are two large cages (FIG. 1C(a-c)): a [$3^{16}4^{28}8^212^4$] poz A cage with 8MR and 12MR faces, and a [$3^{32}4^{36}8^210^812^4$] poz B cage, with 8MR, 10MR and 12MR faces (in the symbols [ ... m$^n$ ... ]

means that there are n faces that are m-rings). There are also smaller [$4^610^4$] poz C cages and [$4^6$] poz D cages located at the interstices between A and B cages (FIGS. 1C(a-c), 1E(a)).

Figure 1E:
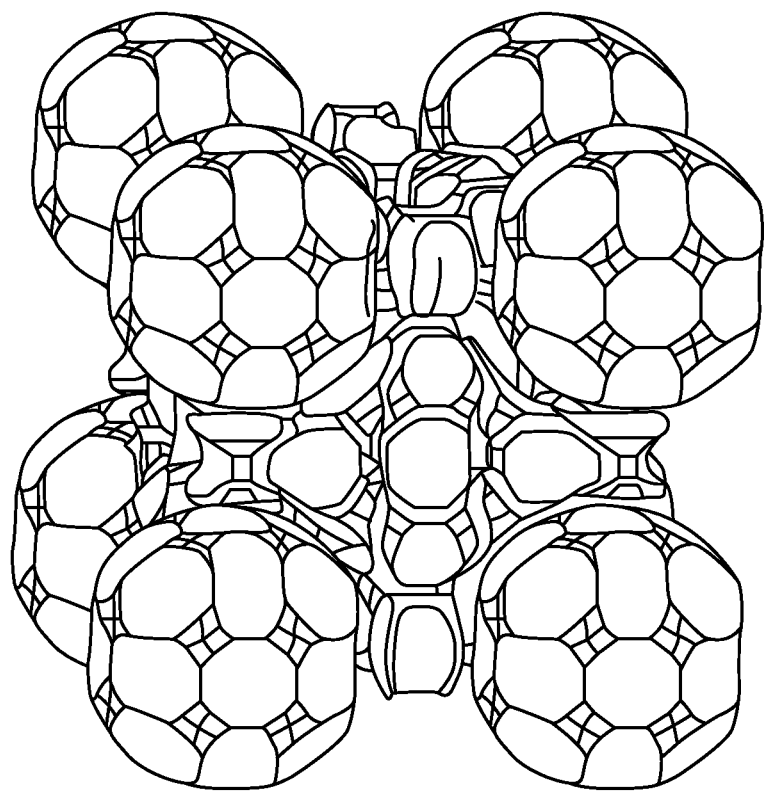
Figure 1E:
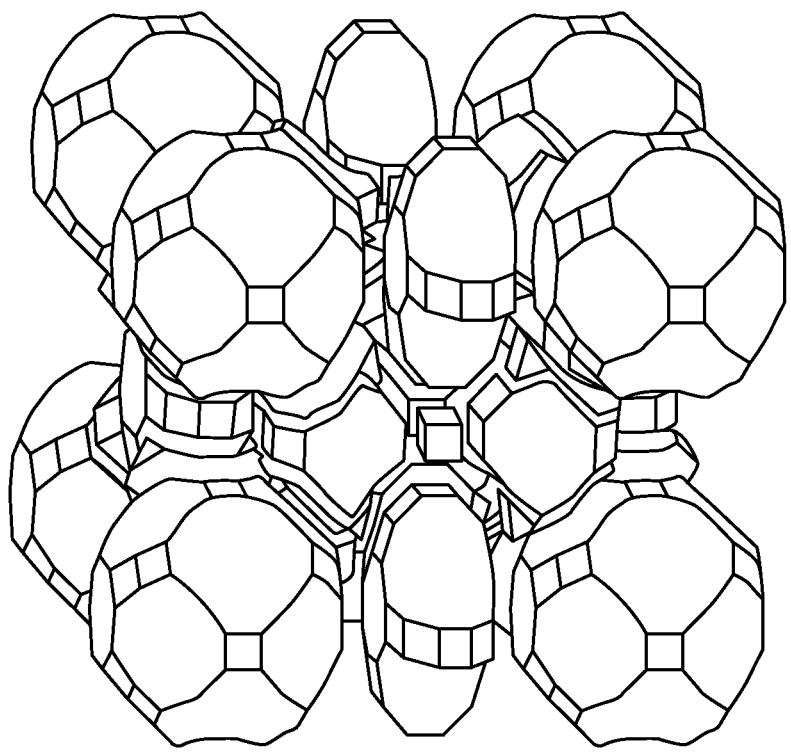

The packing of these cages can be seen from the illustration of them as a tiling in FIG. 1E. In Table C the numbers of faces, edges and vertices in these cages is listed. It may be seen that the A cage has the same size, by this measure, as the faujasite 'super cage', which serves as a benchmark for large cage zeolites; the B cage is significantly larger. The pores of ZIF-95 are of ellipsoidal shape: from the van der Waals surfaces, the A cage measures 25.13 14.3 A° and comprises 1,056 atoms (48 Zn, 504 C, 288 H, 144 N and 72 CO. The B cage measures 30.13 20.0 A° and comprises 1,648 atoms (80 Zn, 784 C, 448 H, 224N and 112 Cl).

TABLE C

| | | Cage size (Å)* | | | | | Metal Atoms |
|---|---|---|---|---|---|---|---|
| Material | Cages | Inner diameter | Outer diameter | Vertices | Faces | Edges | per cage |
| FAU | Super cage | 14.1 | 18.1 | 48 | 26 | 72 | 48 |
| ZIF-95 | poz A | 25.1 × 14.3 | 33.6 × 23.9 | 48 | 26 | 72 | 48 |
| ZIF-95 | poz B | 30.1 × 20.0 | 41.1 × 33.9 | 80 | 34 | 112 | 80 |
| MIL-101[13] | Large cage | 33.8 | 46.7 | 28 | 16 | 42 | 126 |
| Mes.MOF-1[14] | LCage | 47.1 | 59.5 | 28 | 16 | 42 | 84 |
| ZIF-100 | moz | 35.6 | 67.2 | 264 | 182 | 444 | 264 |

Mes, mesoporous. FAU, faujasite.
*Inner diameter of each cage is measured by the diameter of the larges sphere or ellipsoid that fits into the cavity; outer diameter is calculated from the centre-to-centre distance of the outmost atoms of each cage.

The disclosure thus provides a zeolitic framework comprising ZIF having the characteristics of ZIF-95 or ZIF-100. In one embodiment, the ZIF comprises Im3 symmetry, with a unit cell parameter a571.9797(4) Å and unit cell volume of 372,932(4) Å$^3$. Its primitive cell volume of 1.86×10$^5$ Å$^3$ makes ZIF-100 one of the largest inorganic structures ever determined.

Of the ten Zn atoms that form the (3,4)-coordinated net with the topology symbolized as moz, nine are connected to four cbIM linkers and the remaining one (Zn8) is connected to three linkers. One of the features of this ZIF is a giant cage [$3^{48}4^{108}12^{26}$] with 264 vertices. This moz cage (95.6 kDa) is built from 7,524 atoms—264 Zn, 3,604 C, 2,085 H, 26 O, 1,030 N, 515 Cl—and has a 67.2 A° outer sphere diameter and a 35.6 A° inner sphere diameter. The inner sphere diameter is determined by fitting a sphere from the centroid of the cage to the van der Waals surface of its wall. In comparison, the corresponding distances in the faujasite super cage are 18.1 A° and 14.1 A° (Table C)

Restricting the water content of the reaction medium used for ZIF-95 synthesis promotes the crystallization of a new phase, ZIF-100. Less hydrated conditions are achieved by using anhydrous $Zn(O_3SCF_3)_2$ in place of $Zn(NO_3)_2 \cdot 4H_2O$. ZIF-100 was found to have the composition $Zn_{20}(cbIM)_{39}$(OH), where one Zn atom (labelled Zn8) is only tri-coordinated by cbIM.

In one embodiment, the disclosure thus provides a method of making a functionalized ZIF of the disclosure.

Multigram scale synthesis is also provided by the disclosure. Using seven chosen ZIFs of heterolinks (ZIF-60, 61, 68 to 70, 74, and 76), microsynthesis conditions were scalable to 10-g scale and pure ZIF materials obtained.

The zeolitic frameworks of the disclosure are comparable with some of the very porous MOF compounds in surface area and pore volume, and they outperform traditional crystalline microporous materials such as zeolites and ordered mesoporous silicas. Although not required and not wanting to be bound by any theory, this performance may be due in part to the fully exposed edges and faces of the organic links; characteristics that have been proposed as key to creating exceptionally high surface areas.

The disclosure thus provides a frameworks comprising a core, wherein the core comprises a plurality of transition metals linked by linking moiety having a structure selected from I-IX and comprising a functional group at the surface of the framework. The framework comprises a plurality of pores having a surface area greater than about 2000 $m^2/g$ (e.g., about 3,000-18,000 $m^2/g$ or about 3,000-6,000 $m^2/g$). The plurality of pores of a framework of the disclosure comprises a pore volume 0.1 to 0.99 $cm^3/cm^3$ (e.g., about 0.4-0.5 $cm^3/cm^3$). A framework of the disclosure comprises a density of about 0.17 $g/cm^3$. A zeolitic framework of the disclosure can comprise a core comprising the atomic coordinates as set forth in any one of the tables herein.

In another embodiment, a zeolitic framework of the disclosure is characterized by comprising a thermal stability range of at least up to 500° C. and a Langmuir surface area of about 1,240 $m^2/g^{-1}$ and 780 $m^2/g^{-1}$ for ZIF-95 and ZIF-100, respectively, which is more than double those of the most porous zeolites. The BET method yielded surface areas of 1,050 $m^2/g^{-1}$ and 595 $m^2/g^{-1}$, respectively.

In another aspect, the zeolitic framework set forth above may include an interpenetrating framework that increases the surface area of the framework. Although the frameworks of the disclosure may advantageously exclude such interpenetration, there are circumstances when the inclusion of an interpenetrating framework may be used to increase the surface area.

In one embodiment of the disclosure, a gas storage or separation material comprising a zeolitic framework is provided. Advantageously, the zeolitic framework includes one or more sites for storing or separation of gas molecules. Gases that may be stored in the gas storage material of the disclosure include gas molecules comprising available electron density for attachment to the one or more sites on the surface area of a pore or interpenetrating porous network. Such electron density includes molecules having multiple bonds between two atoms contained therein or molecules having a lone pair of electrons. Suitable examples of such gases include, but are not limited to, the gases comprising a component selected from the group consisting of ammonia, argon, carbon dioxide, carbon monoxide, hydrogen, and combinations thereof. In a particularly useful variation the gas storage material is a hydrogen storage material that is used to store hydrogen ($H_2$). In another particularly useful variation, the gas storage material is a carbon dioxide storage material that may be used to separate carbon dioxide from a gaseous mixture.

For example, Carbon dioxide, methane, carbon monoxide and nitrogen adsorption isotherms were measured for both ZIF-95 and -100 (FIG. 2b), which show a disproportionately high affinity and capacity for $CO_2$ (FIG. 2b). ZIF-100 is seen to outperform ZIF-95 and the prototypical adsorbent BPL carbon, which is widely used in industry owing to its ease of desorption and regeneration.

FIG. 2b also illustrates that both ZIFs show complete reversibility of adsorption, indicating that they might serve as selective carbon dioxide reservoirs before the gas is processed further (for example, injected into an underground geologic formation). More detailed analysis of the data in FIG. 2b indicates that one litre of ZIF-100 can hold up to about 28.21 (55.4 g, or 1.7 mmol per g of ZIF-100) of $CO_2$ at 273 K and 15.91 (31.2 g) at 298 K, with a single moz cage capturing as many as 121 $CO_2$ molecules at 273 K and 68 molecules at 298 K and ambient pressure. These adsorption characteristics are in line with data showing 1 L of ZIF-69 storing 82.6 l of $CO_2$ at 273 K. The selectivity of ZIFs for carbon dioxide thus exceeds that of BPL carbon (Table D).

TABLE D

Gas separation of ZIFs and BPL

| Material | Gas pairs | ZIF selectivity*[28] | BPL carbon selectivity[25] | Ratio ZIF/BPL carbon* |
|---|---|---|---|---|
| ZIF-100 | $CO_2/CH_4$ | 5.9 ± 0.4 | 2.5 | 2.4 ± 0.2 |
| ZIF-100 | $CO_2/CO$ | 17.3 ± 1.5 | 7.5 | 2.3 ± 0.2 |
| ZIF-100 | $CO_2/N_2$ | 25.0 ± 2.4 | 11.1 | 2.3 ± 0.2 |
| ZIF-95 | $CO_2/CH_4$ | 4.3 ± 0.4 | 2.5 | 1.7 ± 0.2 |
| ZIF-95 | $CO_2/CO$ | 11.4 ± 1.1 | 7.5 | 1.5 ± 0.1 |
| ZIF-95 | $CO_2/N_2$ | 18.0 ± 1.7 | 11.1 | 1.6 ± 0.2 |

Figure 2C:
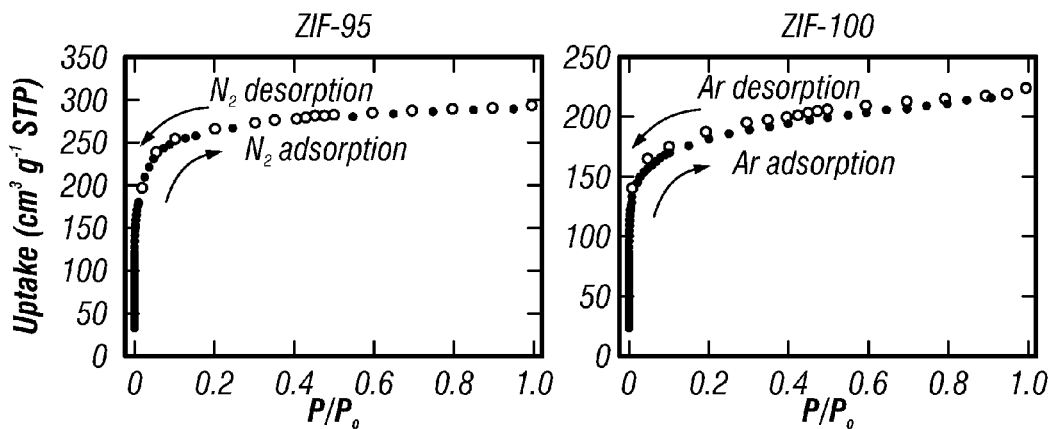
Figure 2C:
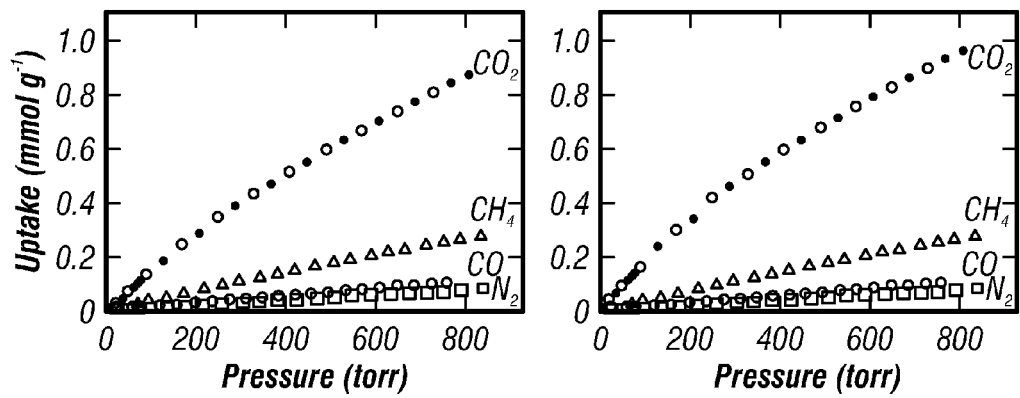
Figure 2C:
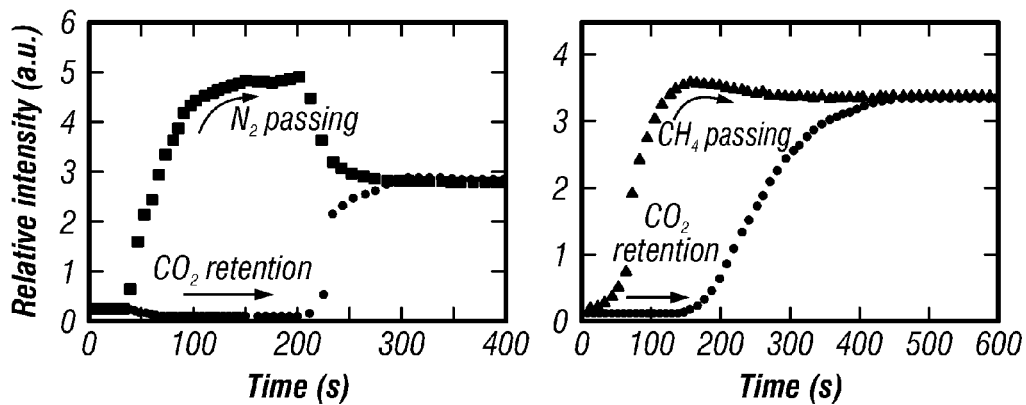

Additional data demonstrate that carbon dioxide can be held in the pores of ZIF-95 and ZIF-100 when exposed to streams containing binary mixtures of $CO_2/CH_4$, $CO_2/CO$ or $CO_2/N_2$ (50:50 v/v). FIG. 2c shows the results for $CO_2/N_2$ passing through 1.2 g of ZIF-95 and $CO_2/CH_4$ passing through 1.1 g of ZIF-100. The data demonstrate that in both cases carbon dioxide is retained in the pores while the other gas passes through without hindrance.

Provided herein are porous Zeolitic Frameworks (ZIFs) having functionalized pores and high surface. The disclosure provides a filtration/separation column comprising a zeolitic imidazolate framework (ZIF) capable of separating $CO_2$ from other gaseous components in a multi-component gas. The retentate can be referred to as being "depleted" of $CO_2$ components. While the effluent stream can represent the desired product.

The disclosure provides an apparatus and method for separating one or more components from a multi-component gas using a separation system having a feed side and an effluent side separated by a zeolitic imidazolate framework (ZIFs) of the disclosure. The ZIFs may comprise a column separation format.

In one embodiment of the disclosure, a gas storage material comprising a zeolitic framework is provided. Gases that may be stored or separated by the methods, compositions and systems of the disclosure includes gas molecules comprising available electron density for attachment to the one or more sites. Such electron density includes molecules having multiple bonds between two atoms contained therein or molecules having a lone pair of electrons. Suitable examples of such gases include, but are not limited to, the gases comprising a component selected from the group consisting of ammonia, argon, carbon dioxide, carbon monoxide, hydrogen, and combinations thereof. In particularly useful variation, the gas binding material is a carbon dioxide binding material that may be used to separate carbon dioxide from a gaseous mixture.

"Natural gas" refers to a multi-component gas obtained from a crude oil well (associated gas) or from a subterranean gas-bearing formation (non-associated gas). The composition and pressure of natural gas can vary significantly. A typical natural gas stream contains methane as a significant component. The natural gas will also typically contain ethane, higher molecular weight hydrocarbons, one or more acid gases (such as carbon dioxide, hydrogen sulfide, carbonyl sulfide, carbon disulfide, and mercaptans), and minor amounts of contaminants such as water, nitrogen, iron sulfide, wax, and crude oil.

The disclosure is particularly suitable for treatment of natural gas streams containing one or more contaminants such as carbon dioxide, hydrogen sulfide, and water vapor. However, the disclosure is not limited to treatment of natural gas. The inventive device and method can be used to separate multi-component gas.

Sorption is a general term that refers to a process resulting in the association of atoms or molecules with a target material. Sorption includes both adsorption and absorption. Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase.

These materials would be used as standard compounds for sorption instruments, and obtained results would be helpful to improve various industrial plants (i.e. separation or recovery of chemical substance).

The advantage of ZIFs over well studied activated carbons is related to the robust porous structures and the ease to functionalize the pore and surface by choosing appropriate organic linkers and/or metal ions.

In a variation of this embodiment, the gaseous storage site comprises a pore in a zeolitic framework functionalized with a group having a desired size or charge. In a refinement, this activation involves removing one or more chemical moieties (guest molecules) from the zeolitic framework. Typically, such guest molecules include species such as water, solvent molecules contained within the zeolitic framework, and other chemical moieties having electron density available for attachment.

The zeolitic frameworks used in the embodiments of the disclosure include a plurality of pores for gas adsorption. In one variation, the plurality of pores has a unimodal size distribution. In another variation, the plurality of pores have a multimodal (e.g., bimodal) size distribution.

The disclosure also provides chemical sensors (e.g. resistometric sensors) capable of sensing the presence of an analyte of interest. There is considerable interest in developing sensors that act as analogs of the mammalian olfactory system. However, may such sensor systems are easily contaminated. The porous structures of the disclosure provide a defined interaction area that limits the ability of contaminate to contact a sensor material the passes through the porous structure of the zeolitic framework of the disclosure. For example, various polymers are used in sensor systems including conductive polymers (e.g., poly(anilines) and polythiophenes), composites of conductive polymers and non-conductive polymers and composites of conductive materials and non-conductive materials. In resistometric systems conductive leads are separated by the conductive material such that a current traverse between the leads and through the sensor material. Upon binding to an analyte, the resistance in the material changes and detectable signal is thus generated. Using the zeolitic framework of the disclosure, the area surrounding the sensor material is limited and serves as a "filter" to limit contaminants from contacting the sensor material, thus increasing sensor specificity.

The disclosure further provides zeolitic catalyst comprising a zeolitic framework of the disclosure. The zeolitic material of the disclosure, as crystalline material or as molding, can be used in the catalytic conversion of organic molecules. Reactions of this type are, for example, oxidations, the epoxidation of olefins, e.g. the preparation of propylene oxide from propylene and $H_2O_2$ the hydroxylation of aromatics, e.g. the preparation of hydroquinone from phenol and $H_2O_2$ or the conversion of toluene into cresol, the conversion of alkanes into alcohols, aldehydes and acids, isomerization, reactions, for example the conversion of epoxides into aldehydes.

The invention is illustrated in the following examples, which are provided by way of illustration and are not intended to be limiting.

EXAMPLES

To illustrate the potential for synthetic diversity of the disclosure, Table 1 demonstrates zeolite topologies DFT, GIS, and MER resulting from the methods of the disclosure. Furthermore, the disclosure demonstrates that the ZIFs of the disclosure are not restricted to purely tetrahedral nets. The first example of an IM based on a mixed-coordination net, $In_2Zn_3(IM)_{12}$ with In(III) in octahedral coordination environment, is also reported. This structure has the topology of the $Al_2Si_3O_{12}$ part of a garnet, such as grossularite $Ca_3Al_2Si_3O_{12}$.

TABLE 1

Composition, structure, and net parameters of ZIF series of compounds

| ZIF-n | Composition | Net* | Zeolite[†] | T/V,[‡] nm$^{-3}$ | d,[§] Å | N[¶] |
|---|---|---|---|---|---|---|
| ZIF-1 | Zn(IM)2 | crb | BCT | 3.64 | 6.94 | 12 |
| ZIF-2 | Zn(IM)2 | crb | BCT | 2.80 | 6.00 | 12 |

TABLE 1-continued

Composition, structure, and net parameters of ZIF series of compounds

| ZIF-n | Composition | Net* | Zeolite† | T/V,‡ nm⁻³ | d,§ Å | N¶ |
|---|---|---|---|---|---|---|
| ZIF-3 | Zn(IM)2 | dft | DFT | 2.66 | 8.02 | 16 |
| ZIF-4 | Zn(IM)2 | cag | — | 3.68 | 2.04 | 20 |
| ZIF-5 | In2Zn3(IM)12 | gar | — | 3.80 | 3.03 | 20 |
| ZIF-6 | Zn(IM)2 | gis | GIS | 2.31 | 8.80 | 20 |
| ZIF-7 | Zn(PhIM)2 | sod | SOD | 2.50 | 4.31 | 24 |
| ZIF-8 | Zn(MeIM)2 | sod | SOD | 2.47 | 11.60 | 24 |
| ZIF-9 | Co(PhIM)2 | sod | SOD | 2.51 | 4.31 | 24 |
| ZIF-10 | Zn(IM)2 | mer | MER | 2.25 | 12.12 | 24 |
| ZIF-11 | Zn(PhIM)2 | rho | RHO | 2.01 | 14.64 | 48 |
| ZIF-12 | Co(PhIM)2 | rho | RHO | 2.01 | 14.64 | 48 |

*For definitions of three-letter abbreviations, see Reticular Chemistry Structure Resource (http:~~okeeffe-ws1.la.asu.edu/RCSR/home.htm).
‡T/V is the density of metal atoms per unit volume.
§d is the diameter of the largest sphere that will fit into the framework.
¶N is the number of vertices of the largest cage.

Table 1 summarizes topology, density, and pore size data for some of the ZIFs of the disclosure. The nets of the structures are denoted by a three-letter symbol that is often the same as that of the corresponding zeolite net. The density of ZIFs are denoted by using the traditional zeolite measure of number of tetrahedral vertices per unit volume (T/V). In an IM framework containing, for example, Zn(II), the Zn . . . Zn distance is ~6.0 Å, whereas the corresponding Si . . . Si distance in a silicate is ~3.0 Å; accordingly, the density (T/V) of an IM analog (i.e., ZIF) of a silicate zeolite is eight times less. For the structures reported here, T/V is in the range 2.0-3.7 nm⁻³ (Table 1). For comparison, the density for oxide zeolites is 12-20 nm⁻³, and for the lowest-density known oxide framework it is 7.1 nm⁻³. Also provided are examples of the size of the sphere that will fit into the cavities without contacting the van der Waals internal surface of the framework. The atom nearest to the center of the cavity is H, a van der Waals radius of 1.2 Å was used for H in determining the fitting sphere size. Note that this value is an approximate indicator of the cage volume because in some cases the cages are elliptical. The table also gives the number of vertices of the largest cage in each structure; this value ranges from 12 (crb) to 48 (rho).

Porosity and Stability of ZIFs.

Certain ZiFs were prepared at the gram scale to allow detailed investigation of their properties. A structural feature of these ZIFs is that they possess large pores (11.6 and 14.6 Å in diameter for ZIF-8 and -11, respectively) connected through small apertures (3.4 and 3.0 Å across for ZIF-8 and -11, respectively). The pore sizes are approximately twice as large as those of their zeolite counterparts by virtue of the longer IM linking units; however, the existence of side chain or ring on the link renders the aperture sizes to the lower limit for molecular sieves (Table 2).

TABLE 2

Structural characteristics of ZIF-8 and -11 calculated from single crystal x-ray analysis

| | Pore aperture, Å | | | Pore diameter, Å | Surface area m²/g | Pore volume cm³/g |
|---|---|---|---|---|---|---|
| Zif-n | 8-ring | 6-ring | 4-ring | | | |
| ZIF-8 | — | 3.4 | * | 11.6 | 1,947 | 0.663 |
| ZIF-11 | 3.0 | 3.0 | * | 14.6 | 1,676 | 0.582 |

All calculations were based on the Free Volume routine of CERIUS2 software (Version 4.2; AttSci; Accelrys, Inc., San Diego; probe radius 1.4 Å, medium grid) and on the single crystal x-ray structures of ZIF-8 and -11 with guests removed and disorder effects averaged.
* The aperature sizes of the 4-rings in both ZIF-8 and -11 are negligible.

Thermal gravimetric analysis (TGA) performed on as-synthesized ZIF-8 and -11 revealed these compounds' thermal stability. The TGA trace for ZIF-8 showed a gradual weight-loss step of 28.3% (25-450° C.), corresponding to partial loss of guest species [1 N,N-dimethylformamide (DMF) and 3 $H_2O$; calcd. 35.9%], followed by a plateau (450-550° C.). More impressively, the TGA trace for ZIF-11 revealed a sharp weight-loss step of 22.8% (25-250° C.), corresponding to the escape of all N,Ndiethylformamide (DEF) solvent molecules trapped in the pores (0.9 DEF; calcd. 23.3%), despite the fact that DEF is actually much larger than the aperture of ZIF-11 in size. The TGA trace of ZIF-11 also showed a long plateau in the temperature range 250-550° C., indicating its high thermal stability in the absence of guest molecules. The guests in ZIF-8 and -11 were released without damaging the frameworks, as evidenced by the coincidence of the powder x-ray diffraction (PXRD) patterns of a ZIF-8 sample and a ZIF-11 sample heated to and held at 500 and 300° C., respectively, in $N_2$ atmosphere with the PXRD patterns simulated from single crystal structures. Such high thermal stability of ZIFs (up to 550° C. in $N_2$) is well beyond that of the permanently porous cubic structure of MOF-5 (decomposes at 450° C. in $N_2$), only matched by very few MOFs having relatively dense structures.

The amide guests included in as-synthesized ZIF-8 and -11 could be more readily removed by solvent-exchange. The thermogravimetric behavior of ZIF-8 and -11 were significantly simplified after they were immersed in organic solvents, such as methanol. To remove the guest species from the frameworks and prepare the evacuated forms of ZIF-8 and -11 for gas-sorption analysis, the as-synthesized ZIF samples were immersed in methanol at ambient temperature for 48 h, and evacuated at ambient temperature for 5 h, then at an elevated temperature (300° C. for ZIF-8; 180° C. for ZIF-11) for 2 h. ZIF samples thus obtained were optimally evacuated, as evidenced by their well maintained PXRD patterns and the long plateau (25-550° C.) in their TGA traces.

The architectural rigidity and consequently the permanent porosity of evacuated ZIF-8 and -11 were unequivocally proven by gas-sorption analysis. Type I nitrogen sorption isotherm behavior was observed for ZIF-8, which reveals its microporous nature. Apparent surface areas of 1,810 m²/g (Langmuir model) and 1,630 m²/g [Brunauer-Emmett-Teller (BET) model] for ZIF-8 were obtained by using the data points on the adsorption branch in the range of $P/P_0$=0.01-0.10, and a micropore volume of 0.636 cm³/g for ZIF-8 was obtained based on a single data point at $P/P_0$=0.10. The experimental surface area and micropore volume values of ZIF-8 fit well with the predictions based on its single crystal structure (Table 2). These surface areas surpass the highest values reported for zeolites and ordered mesoporous silica-type materials. Conversely, ZIF-11 was nonporous to nitrogen because its aperture size (3.0 Å) was smaller than the kinetic diameter of nitrogen (3.6 Å); however, it was able to take up hydrogen. Both ZIF-8 and -11 showed reversible hydrogen sorption behavior. Interestingly, the initial hydrogen uptake of ZIF-11 was much higher than that of ZIF-8, because of its unique cage interior, which is composed of protruding benzene side rings of the PhIM links around which favorable hydrogen sorption sites may be generated. However, ZIF-8 was similar to ZIF-11 in hydrogen uptake when the adsorbate pressure approached 1 atm [145 cm$^3$/g at standard temperature and pressure (STP)] or 12.9 mg/g for ZIF-8; 154 cm$^3$/g STP or 13.7 mg/g for ZIF-11). This result is expected because ZIF-8 has higher surface area and pore volume (Table 2). The ultimate hydrogen capacity of ZIF-8 was uncovered in a high-pressure (up to 80 bar) hydrogen sorption measurement at 77 K on a large batch of evacuated ZIF-8 (0.724 g), which showed 350 cm$^3$/g STP (31 mg/g) at 55 bar. The hydrogen uptake of ZIF-8 and its Langmuir surface area (1,810 m$^2$/g) fit well in a linear relationship proposed recently based on the high-pressure hydrogen sorption measurements on a series of MOFs with high surface areas.

The chemical stability of ZIFs was examined by suspending samples of ZIF-8 and -11 in boiling benzene, methanol, water, and aqueous sodium hydroxide, conditions that reflect extreme operational parameters of typical industrial chemical processes. ZIF samples were immersed in the desired solvent for 1-7 days at ambient temperature, 50° C., and at the boiling point of each medium. During this process, samples were periodically observed under an optical microscope and found to be insoluble under each of these conditions. PXRD patterns collected for each sample at designated intervals showed that the solid samples of ZIF-8 and -11 maintained their full crystallinity and were impervious to the boiling organic solvents for 7 days. Both ZIFs sustained their structures in water at 50° C. for 7 days. ZIF-8 thus was further probed and shown to be unchanged for up to 24 h in 0.1 and 8 M aqueous sodium hydroxide at 100° C. The hydrothermal stability of ZIF-8 is superior to those of original MCM and SBA types of ordered mesoporous silica, even rivaling the ultrastable derivatives of these materials.

Typical ZIF Synthesis.

Benzimidazole, 2-methylimidazole, Indium nitrate pentahydrate and cobalt nitrate hexahydrate were purchased from the Aldrich Chemical Co. and imidazole, N,N-dimethylformamaide (DMF), N-methylpyrrolidinone (NMP) were purchased from the Fisher Scientific International Inc. N,N-diethylformamide (DEF) was obtained from BASF Corporation. Zinc nitrate tetrahydrate was purchased from the EM Science. All starting materials were used without further purifications. All experimental operations were performed in air. (ZIF syntheses are exemplified here by the synthesis of ZIF-8) A solid mixture of zinc nitrate tetrahydrate Zn(NO$_3$)$_2$.4H$_2$O (0.210 g, 8.03×10$^{-4}$ mol) and 2-methylimidazole (H-MeIM) (0.060 g, 7.31×10$^{-4}$ mol) was dissolved in 18 ml of DMF in a 20-ml vial. The vial was capped and heated at a rate of 5° C./min to 140° C. in a programmable oven and held at this temperature for 24 h, then cooled at a rate of 0.4° C./min to room temperature. After removal of mother liquor from the mixture, chloroform (20 ml) was added to the vial. Colorless polyhedral crystals were collected from the upper layer, washed with DMF (10 ml×3), and dried in air for 10 min (yield: 0.032 g, 25% based on H-MeIM). The product was formulated by using elemental microanalysis as Zn(MeIM)$_2$.(DMF).(H$_2$O)$_3$ (C$_{11}$H$_{23}$N$_5$O$_4$Zn; Calcd. C, 37.25; H, 6.54; N, 19.74. Found. C, 37.69; H, 5.22; N, 19.58). The purity of ZIF-8 product has also been confirmed by PXRD analysis.

Single Crystal X-Ray Diffraction Studies.

All of the intensity data were collected on a SMART APEX CCD diffractometer (Bruker-AXS, Madison, Wis.) with graphite monochromated MoKα (λ=0.71073 Å) radiation. Structures were solved by direct methods, and successive difference Fourier syntheses were made with the SHELXTL software package (Bruker-AXS).

PXRD Studies.

Powder x-ray data were collected by using a D8-Advance θ-2θ diffractometer (Bruker) in reflectance Bragg-Brentano geometry employing Ni-filtered CuKα line focused radiation at 1,600 W (40 kV, 40 mA) power and equipped with a Na(Tl) scintillation detector fitted with a 0.2-mm radiation entrance slit. Samples were mounted on zero background sample holders by dropping powders from a wide-blade spatula and then leveling the sample surface with a razor blade. All samples were ground before PXRD experiment.

TGA.

All samples were run on a Q-500 series thermal gravimetric analyzer (TA Instruments, New Castle, Del.) with samples held in platinum pans in a continuous-flow nitrogen atmosphere. Samples were heated at a constant rate of 5° C./min during all TGA experiments.

Gas-Sorption Measurements.

All low-pressure gas-sorption experiments (up to 1 atm) were performed on a Autosorb-1C automatic volumetric instrument (Quantachrome, Boynton Beach, Fla.). High-pressure hydrogen sorption experiments (up to 80 bar) were performed on a HPA-100 volumetric instrument (VTI, Hialeah, Fla.) equipped with a home-made liquid nitrogen cooling system to sustain a constant coolant bath level. The compressibility factors of high-pressure gases were determined by using the REFPROP program [Version 7.0; National Institute of Standards and Technology (NIST), Gaithersburg, Md.] and the NIST Standard Reference Data Base 23. Before gas-sorption analysis, ZIF-8 and -11 samples were immersed in methanol at ambient temperature for 48 h and evacuated at ambient temperature for 5 h, then at an elevated temperature (300° C. for ZIF-8, 180° C. for ZIF-11) for 2 h.

(ZIF-1 crb): Zn(IM)2.(Me2NH).

A solid mixture of zinc nitrate tetrahydrate Zn(NO3)2.4H2O (0.09 g, 3.44×10$^{-4}$ mol) and imidazole (H-IM) (0.15 g, 2.20×10$^{-3}$ mol) was dissolved in 18 mL DMF in a 20-mL vial. The vial was capped and heated for 24 h in a 85° C. isothermal oven. The vial was then removed from the oven and allowed to cool to room temperature naturally. Colorless cubic crystals of ZIF-1 thus produced were washed with DMF (3 mL×3) and dried in air (10 min) (yield: 0.014 g, 17% based on zinc nitrate tetrahydrate). Elemental analysis C8H13N5Zn=Zn(IM)2.(Me2NH): Calcd. C, 39.28; H, 5.36; N, 28.65. Found C, 39.47; H, 4.39; N, 27.13. FT-IR: (KBr 4000-400 cm$^{-1}$): 3445 (br), 3103 (w), 2935 (w), 2385 (w), 2355 (w), 1647 (s), 1499 (m), 1418 (w), 1403 (w), 1321 (w), 1291 (w), 1245 (w), 1184 (w), 1087 (s), 1026 (w), 985 (w), 960 (m), 837 (w), 761 (m), 680 (m), 603 (w).

(ZIF-2 crb): Zn(IM)2.

0.265 mL imidazole stock solution (0.150 M, 3.98×10$^{-4}$ mol) and 0.035 mL Zn(NO3)2.4H2O stock solution (0.075 M, 2.63×10$^{-6}$ mol). The product was in the form of small rod-shaped single crystals.

(ZIF-3 dft): Zn(IM)2.

A solid mixture of zinc nitrate tetrahydrate Zn(NO3)2.4H2O (0.010 g, 3.82×10$^{-5}$ mol) and imidazole (H-IM) (0.030 g, 4.41×10$^{-4}$ mol) was added in a 4-mL vial and dissolved in a mixed solvent of DMF (2 mL) and NMP (1 mL). The vial was capped and heated for 4 d in a 85° C.

isothermal oven. The vial was then removed from the oven and allowed to cool to room temperature naturally. Several prism-shaped crystals formed at the bottom of the vial along with some white powder-like precipitate. The crystals of ZIF-3 were collected manually for single crystal X-ray structure determination.

(ZIF-4 cag): Zn(IM)2.(DMF)(H2O)

A solid mixture of zinc nitrate tetrahydrate Zn(NO3) 2.4H2O (0.040 g, $1.53 \times 10^{-4}$ mol) and imidazole (H-IM) (0.030 g, $4.41 \times 10^{-4}$ mol) was dissolved in 3 mL DMF in a 4-mL vial. The vial was capped and heated at a rate 5° C./min to 130° C. in a programmable oven, held at this temperature for 48 h, then cooled at a rate of 0.4° C./min to room temperature. Colorless rhombohedral crystals of ZIF-4 thus produced were washed with DMF (3 mL×3) and dried in the air (10 min) (yield: 0.021 g, 47% based on zinc nitrate tetrahydrate). Elemental analysis: C9H15N5O2Zn=Zn(IM)2.(DMF)(H2O): Calcd. C, 37.19; H, 5.20; N, 24.10. Found C, 38.02; H, 4.14; N, 26.74. FT-IR: (KBr 4000-400 cm$^{-1}$): 3427 (br), 3111 (w), 2926 (w), 2856 (w), 1688 (m), 1612 (br), 1502 (m), 1392 (w), 1282 (w), 1247 (w), 1176 (w), 1091 (s), 986 (w), 961 (m), 846 (w), 770 (m), 680 (m), 490 (br).

(ZIF-5 gar): In2Zn3(IM)12

Indium nitrate pentahydrate, In(NO3)3.5H2O (0.156 g, $4.0 \times 10^{-4}$ mol), zinc nitrate tetrahydrate Zn(NO3)2.4H2O (0.026 g, $1.0 \times 10^{-4}$ mmol) and imidazole (H-IM) (0.136 g, $2 \times 10^{-3}$ mol) were dissolved in a mixed solvent of DEF/nb-utanol (4 mL/2 mL). After the addition of small amount of tetraethylammonium hydroxide (35% aqueous solution), the mixture was transferred into a Teflon-lined Parr stainless steel vessel (23 mL) and heated at 150° C. for 72 hours under autogenous pressure. Pale-yellow crystals thus produced were washed with ethanol and dried in air (yield: 70%, based on zinc nitrate tetrahydrate). Elemental analysis: C36H36N24Zn3In2=In2Zn3(IM)12: Calcd. C, 35.14; H, 2.95; N, 27.32. Found C, 33.97; H, 2.82; N, 26.22. Zn/In molar ratio: Calcd, 1.50, Found, 1.52. FT-IR (KBr 4000-400 cm$^{-1}$): 3433 (br), 3132 (m), 3112 (m), 2601 (w), 2524 (w), 1697 (m), 1605 (m).

(ZIF-6 gis): Zn(IM)2.

Figure 4E:
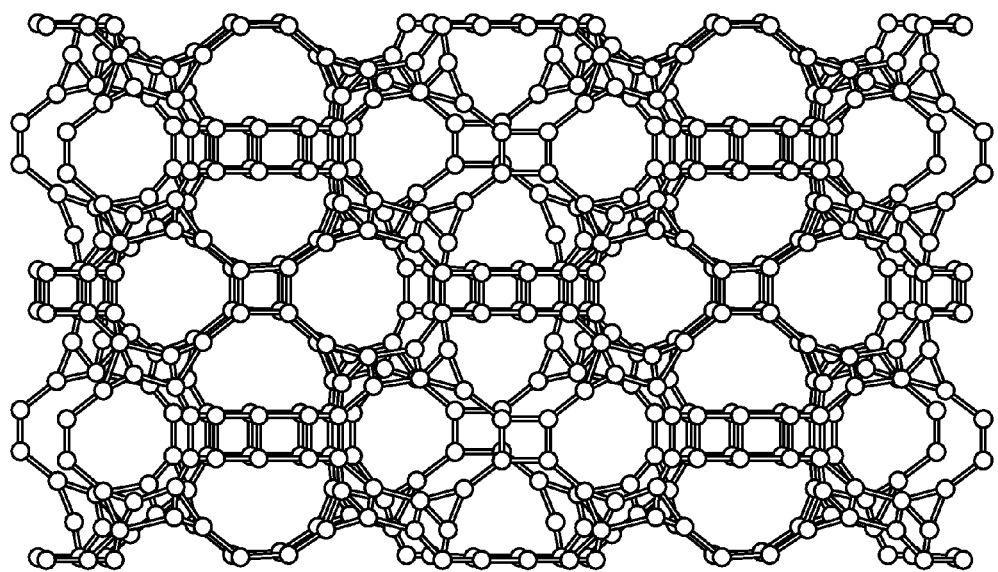
FIG. 4A-E shows structures associated with ZIF 105. Panel A shows ZIF 105 Building Unit, $ZnN_4$ cluster. Panel B shows SBU, 3MR. Panel C shows 4MR. Panel D shows D4MRs; E: ZIF 105 Framework 4 u.c.
Figure 4A:
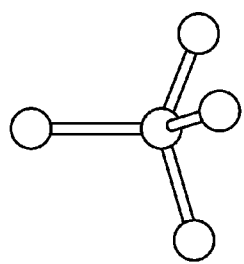
Figure 4C:
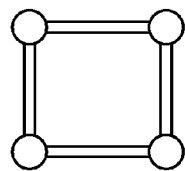
Figure 4B:
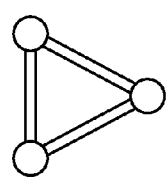
Figure 4D:
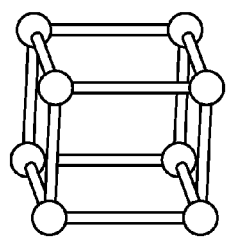

0.257 mL imidazole stock solution (0.150 M, $3.86 \times 10^{-5}$ mol) and 0.043 mL Zn(NO3)2.4H2O stock solution (0.075 M, $3.23 \times 10^{-6}$ mol). The product was in the form of large inter-grown blocks, which could be cut into small single crystals under an optical microscope. The FT-IR spectrum of imidazole shows many characteristics of nitrogen-containing heterocycle. For pyrazoles, imidazoles, triazoles and tetrazoles, the C—H stretch absorbs near 3125 cm$^{-1}$. The double bonds on the ring absorb with several bands between 1665-1430 cm$^{-1}$ when the ring system is not substituted so as to allow the formation of tautomers. The NH group absorbs strongly between 3335-2500 cm$^{-1}$, and in many cases is very similar in shape to the OH stretch of the carboxylic acid dimmer. In the imidazoles, this band is accompanied by a weak band near 1820 cm$^{-1}$. As shown in FIG. 4(b), the complete disappearance of the strong and broad NH band between 3350-2500 cm$^{-1}$ and the associated weak band near 1820 cm$^{-1}$ indicates that the imidazole links in ZIF-5 In2Zn3(IM)12 has been fully deprotonated.

(ZIF-7 sod): Zn(PhIM)2.(H2O)3.

A solid mixture of zinc nitrate tetrahydrate Zn(NO3) 2.4H2O (0.030 g, $1.15 \times 10^{-4}$ mol) and benzimidazole (H-PhIM) (0.010 g, $8.46 \times 10^{-5}$ mol) was dissolved in 3 mL DMF in a 4-mL vial. The vial was capped and heated at a rate of 5° C./min to 130° C. in a programmable oven, held at this temperature for 48 h, then cooled at a rate of 0.4° C./min to room temperature. After removal of mother liquor from the mixture, chloroform (3 mL) was added to the vial. Colorless cubic crystals of ZIF-7 were collected from the upper layer, washed with DMF (3 mL×3) and dried in air (10 min) (yield: 0.015 g, 37% based on H-PhIM). Elemental analysis C14H16N4O3Zn=Zn(IM)2.(H2O)3: Calcd. C, 47.54; H, 4.56; N, 15.84. Found. C, 46.95; H, 3.57; N, 16.40. FT-IR: (KBr 4000-400 cm$^{-1}$): 3450 (br), 3063 (w), 2930 (w), 1678 (s), 1622 (w), 1479 (s), 1387 (m), 1306 (m), 1286 (m), 1245 (s), 1209 (w), 1189 (m), 1123 (m), 1097 (m), 1011 (m), 914 (m), 781 (m), 746 (s), 654 (m), 476 (m), 435 (m).

(ZIF-8 sod): Zn(MeIM)2.(DMF).(H2O)3.

A solid mixture of zinc nitrate tetrahydrate Zn(NO3) 2.4H2O (0.210 g, $8.03 \times 10^{-4}$ mol) and 2-methylimidazole (H-MeIM) (0.060 g, $7.31 \times 10^{-4}$ mol) was dissolved in 18 mL DMF in a 20-mL vial. The vial was capped and heated at a rate of 5° C./min to 140° C. in a programmable oven, held at this temperature for 24 h, then cooled at a rate of 0.4° C./min to room temperature. After removal of mother liquid from the mixture, chloroform (20 mL) was added to the vial. Colorless polyhedral crystals of the product were collected from the upper layer, washed with DMF (10 mL×3) and dried in air (10 min) (yield: 0.032 g, 25% based on H-MeIM). Elemental analysis. C11H23N5O4Zn=Zn(MeIM)2.(DMF).(H2O)3 Calcd. C, 37.25; H, 6.54; N, 19.74. Found. C, 37.69; H, 5.22; N, 19.58 FT-IR: (KBr 4000-400 cm$^{-1}$): 3460 (w), 3134 (w), 2930 (m), 2854 (w), 2767 (w), 2487 (w), 2457 (w), 1693 (s), 1591 (w), 1459 (s), 1428 (s), 1392 (m), 1311 (s), 1265 (w), 1189 (m), 1148 (s), 1091 (m), 1000 (m), 960 (w), 766 (s), 695 (m), 664 (m), 425 (s).

(ZIF-9 sod): Co(PhIM)2.(DMF)(H2O).

A solid mixture of cobalt nitrate hexahydrate Co(NO3) 2.6H2O (0.210 g, $7.21 \times 10^{-4}$ mol) and benzimidazole (H-PhIM) (0.060 g, $5.08 \times 10^{-4}$ mol) was dissolved in 18 mL DMF in a 20-mL vial. The vial was capped and heated at a rate of 5° C./min to 130° C. in a programmable oven, held at this temperature for 48 h, then cooled at a rate of 0.4° C./min to room temperature. Purple cubic crystals thus produced were washed with DMF (3 mL×3) and dried in air (10 min) (yield: 0.030 g, 30% based on H-PhIM). Elemental analysis C17H19N5O2Co=Co(PhIM)2.(DMF)(H2O) Calcd. C, 53.13; H, 4.98; N, 18.22. Found. C, 52.82; H, 4.25; N, 18.23. FT-IR: (KBr 4000-400 cm$^{-1}$): 3442 (br), 3071 (w), 2926 (w), 1678 (s), 1612 (w), 1467 (s), 1387 (w), 1302 (w), 1287 (m), 1242 (s), 1206 (w), 1186 (w), 1126 (w), 1096 (w), 1011 (w), 916 (w), 780 (w), 750 (s), 660 (w), 600 (br), 560 (w), 475 (w).

(ZIF-10 mer): Zn(IM)2.

A solid mixture of zinc nitrate tetrahydrate Zn(NO3) 2.4H2O (0.010 g, $3.82 \times 10^{-5}$ mol) and imidazole (H-IM) (0.030 g, $4.41 \times 10^{-4}$ mol) was dissolved in 3 mL DMF in a 4-mL vial. The vial was capped and heated for 4 d in an isothermal oven at 85° C. The reaction mixture was then allowed to cool to room temperature naturally. Several block-shape crystals of ZIF-10 formed on the wall and bottom, and were separated by hand and collected for single crystal X-ray structure determination.

(ZIF-11 rho) Zn(PhIM)2.(DEF)0.9.

A solid mixture of zinc nitrate tetrahydrate Zn(NO3) 2.4H2O (0.60 g, $2.3 \times 10^{-3}$ mol) and benzimidazole (H-PhIM) (4.2 g, $3.5 \times 10^{-2}$ mol) was dissolved in 360 mL DEF in a 500-mL wide-mouth glass jar. The capped jar was heated for 4 d in an isothermal oven at 100° C. The jar was then removed from the oven, and allowed to cool to room temperature naturally. Cubic colorless crystals formed on the walls of the jar along with a crystalline powder at the bottom. Although the powder and crystals were proven to be the same phase by powder X-ray diffraction, only the crystals on the wall were used for bulk characterizations. The powder and mother liquor was removed by repeating the cycle of decanting, washing with DMF and sonicating several times. Colorless crystals of ZIF-11 were collected by filtration, washed with DMF (200 mL×2) and dried in the air (30 min) (yield: 0.21 g, 23% based on Zn(NO3)2.4H2O). Elemental analysis C18H21N5O1Zn1=Zn(PhIM)2.(DEF)0.9 Calcd. C, 56.94; H, 5.10; N, 17.59. Found: C, 55.69; H, 4.64; N, 17.58. FT-IR (KBr, 4000–400 cm$^{-1}$): 3452 (br), 3091 (w), 3056 (w), 2981 (w), 2941 (w), 2876 (w), 2781 (w), 2525 (w), 1939 (w), 1903 (w), 1783 (w), 1668 (s), 1618 (m), 1467 (s), 1397 (w), 1367 (w), 1307 (m), 1282 (m), 1247 (m), 1212 (w), 1187 (m), 1121 (m), 1001 (m), 911 (m), 826 (w), 771 (m), 751 (s), 645 (m), 553 (m), 520 (w), 475 (m).

(ZIF-12 rho): Co(PhIM)2.

A solid mixture of cobalt nitrate hexahydrate Co(NO3) 2.6H2O (0.010 g, 3.44×10$^{-5}$ mol) and benzimidazole (H-PhIM) (0.030 g, 2.54×10$^{-5}$ mol) was dissolved in 3 mL DEF in a 4-mL vial. The capped vial was heated for 2 d in an isothermal oven at 130° C. The reaction mixture was then allowed to cool to room temperature naturally. Several cubic crystals of ZIF-12 formed at the bottom and on the wall of the vial, and they were collected for single crystal X-ray structure determination.

ZIF-20: $Zn(Pur)_2.(DMF)_{0.75}(H_2O)_{1.5}$.

A solid mixture of zinc nitrate tetrahydrate $Zn(NO_3)_2.4H_2O$ (65 mg, 0.25 mmol, EM Science) and purine (150 mg, 1.25 mmol, Fluka or Sigma) was dissolved in 5 mL DMF (Fisher) in a 20-mL vial to obtain a slightly suspended solution. The vial was tightly capped and heated in a 65° C. isothermal oven for 3 days to yield pale yellow octahedral crystals along with small amount of powder. After cooling the vial to room temperature naturally, the powder product was removed by decanting with mother liquor and DMF (5 mL×3). The crystals were dried in air for 30 min [yield: 48 mg, 50% based on $Zn(NO_3)_2.4H_2O$]. Elemental analysis: Calcd for $Zn(Pur)_2.(DMF)_{0.75}(H_2O)_{1.5}$: C, 38.17; H, 3.73; N, 31.80. Found C, 37.93; H, 3.52; N, 31.85%. FT-IR (KBr, 4000-400 cm$^{-1}$): 3433 (br), 3098 (w), 3065 (w), 3036 (w), 2930 (w), 2856 (w), 1670 (s), 1589 (s), 1568 (m), 1477 (s), 1398 (s), 1310 (s), 1221 (s), 1192 (m), 1094 (m), 1020 (w), 924 (m), 804 (m), 791 (m), 683 (w), 644 (m), 621 (w), 575 (w), 498 (w), 403 (w).

ZIF-21: $Co(Pur)_2.(DMF)(H_2O)$.

A solid mixture of cobalt(II) nitrate hexahydrate $Co(NO_3)_2.6H_2O$ (146 mg, 0.502 mmol, Aldrich) and purine (300 mg, 2.50 mmol) were dissolved in DMF (5 mL) in a 20-mL vial. To the solution, 2.0 M dimethylamine solution in MeOH (1.25 mL, 2.50 mmol, Aldrich) was added. The vial was tightly capped and heated in a 85° C. isothermal oven for 24 h to yield purple octrahedral crystals. After cooling the vial to room temperature naturally, the crystals were rinsed with DMF (5 mL×3) and dried in air for 1 h [yield: 92 mg, 47% based on $Co(NO_3)_2.6H_2O$]. Elemental analysis: Calcd for $Co(Pur)_2.(DMF)(H_2O)$: C, 40.22; H, 3.89; N, 32.47. Found C, 40.36; H, 3.93; N, 32.16%. FT-IR (KBr, 4000-400 cm$^{-1}$): 3418 (br), 3086 (w), 2924 (w), 2855 (w), 1665 (s), 1589 (s), 1560 (m), 1468 (s), 1443 (w), 1396 (s), 1308 (m), 1234 (s), 1207 (s), 1188 (s), 1109 (m), 916 (m), 804 (m), 791 (w), 677 (w), 648 (m), 623 (w), 573 (w), 500 (w).

ZIF-22: $Zn(5-Azabenzimidazolato)_2.(DMF)_{0.75}(H_2O)_2$.

A solid mixture of zinc nitrate tetrahydrate $Zn(NO_3)_2.4H_2O$ (52 mg, 0.20 mmol) and 5-azabenzimidazole (238 mg, 2.00 mmol, Aldrich) was dissolved in 2 mL DMF in a 4-mL vial to obtain a white precipitate. The vial was tightly capped and heated in a 150° C. isothermal oven for 3 days to yield pale yellow octahedral crystals along with small amount of powder. After cooling the vial to room temperature naturally, the powder product was removed by decanting with mother liquor and DMF (4 mL×3). The crystals were dried in air for 30 min [yield: 68 mg, 87% based on $Zn(NO_3)_2.4H_2O$]. Elemental analysis: Calcd for $Zn(5-Azabenzimidazolato)_2$.$(DMF)_{0.75}(H_2O)_2$: C, 43.61; H, 4.43; N, 24.09. Found C, 43.74; H, 4.33; N, 24.24%. FT-IR (KBr, 4000-400 cm$^{-1}$): 3422 (br), 3067 (br), 2930 (w), 2858 (w), 1672 (s), 1601 (s), 1572 (w), 1468 (s), 1439 (m), 1408 (w), 1385 (s), 1342 (w), 1313 (s), 1285 (m), 1234 (s), 1205 (w), 1186 (m), 1173 (w), 1096 (m), 1063 (w), 1038 (w), 1016 (m), 991 (w). 918 (s), 816 (m), 793 (m), 660 (m), 644 (m), 613 (m), 565 (w), 467 (w), 420 (w).

ZIF-23: $Zn(4-Azabenzimidazolato)_2.(H_2O)_{0.25}$.

A solid mixture of zinc nitrate tetrahydrate $Zn(NO_3)_2.4H_2O$ (52 mg, 0.20 mmol) and 4-azabenzimidazole (119 mg, 1.00 mmol, Aldrich) was dissolved in 1 mL DMF in a 4-mL vial. The vial was tightly capped and heated in a 100° C. isothermal oven for 1 day to yield pale yellow prism crystals. After cooling the vial to room temperature naturally, the crystals were rinsed with DMF (5 mL×3) and dried in air for 30 min [yield: 55 mg, 90% based on $Zn(NO_3)_2.4H_2O$]. The same product was obtained in the reaction at different temperature (65 and 150° C.), at which ZIF-20 and -22 were synthesized, respectively. Reaction with a different ligand/metal ratio (1:10, instead of 1:5 as used in a synthesis of ZIF-21 also gave the same compound. Elemental analysis: Calcd for $Zn(4-Azabenzimidazolato)_2.(H_2O)_{0.25}$: C, 47.08; H, 2.80; N, 27.45. Found C, 47.00; H, 2.82; N, 27.84%. FT-IR (KBr, 4000-400 cm$^{-1}$): 3439 (br), 3080 (m), 3053 (m), 2937 (w), 1919 (w), 1879 (w), 1850 (w), 1665 (m), 1597 (s), 1574 (w), 1474 (s), 1406 (s), 1395 (w), 1313 (m), 1290 (s), 1263 (w), 1225 (m), 1186 (m), 1117 (w), 1042 (w), 1013 (w), 959 (w), 918 (m), 802 (m), 771 (s), 667 (m), 652 (s), 594 (w), 569 (w), 503 (m), 490 (w).

ZIF-35:

A solid mixture of zinc nitrate tetrahydrate $Zn(NO_3)_2.4H_2O$ (78 mg, 0.30 mmol) and 4-cyanoimidazole (284 mg/3.05 mmol) was dissolved in 1 mL N-methylpyrrolidonone (NMP) in a 4-mL vial. The vial was tightly capped and heated in a 100 C isothermal oven for 3 days to yield pale yellow rectangular crystals (yield: 73 mg). Activation of ZIF-35 for gas adsorption measurement and gas separation experiments: the as-synthesized sample of ZIF-35 was immersed in anhydrous methanol in a glove box for 3 days; during the exchange the methanol was refreshed six times. The resulting methanol-exchanged sample of ZIF-35 in methanol was transferred to a glass tube in a glove box and the solvent was roughly decanted by pipette. The sample was then evacuated at ambient temperature for 12 hours to yield an activated sample.

(ZIF-60 mer): $Zn(IM)_{1.5}(mIM)_{0.5}$.

0.18 mL imidazole stock solution (0.15 M, 2.7×10$^{-5}$ mol) and 0.060 mL 2-methylimidazole stock solution (0.15 M, 0.90×10$^{-5}$ mol) was mixed together. To this solution was added 0.060 mL Zn(NO3)2.4H2O stock solution (0.15 M, 0.90×10$^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 85° C. and allowed to react solvothermally for 72 h. The product was in the form of prism-shaped single crystals. Elemental analysis $C_{13}H_9N_8Zn_2$=$Zn(IM)_{1.5}(MeIM)_{0.5}.(Me_2NH)(H_2O)_3$: Calcd. C, 33.17; H, 6.55; N, 22.76. Found C, 33.28; H, 6.19; N, 22.13. Elemental analysis (activated) $C_{13}H_9N_8Zn_2$=$Zn(IM)_{1.5}(MeIM)_{0.5}$: Calcd. C, 37.44; H, 3.38; N, 26.87; Zn, 31.36. Found C, 36.97; H, 3.19; N, 27.13; Zn, 32.06. FT-IR: (KBr 4000-400 cm$^{-1}$): 3445 (br), 3134 (w), 2599 (w), 2528 (w), 2503 (w), 1683 (s), 1602 (m), 1505 (w), 1250 (w), 1163 (w), 955 (w), 756 (w), 675 (w).

(ZIF-61 zni): Zn(IM)(mIM).

0.12 mL imidazole stock solution (0.15 M, 1.8×10$^{-5}$ mol) and 0.12 mL 2-methylimidazole stock solution (0.15 M, 1.8×10$^{-5}$ mol) was mixed together. To this solution was added 0.060 mL Zn(NO$_3$)$_2$.4H$_2$O stock solution (0.15 M, 0.90×10$^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 11 100° C. and allowed to react solvothermally for 96 h. The product was in the form of rodshaped single crystals. Elemental analysis C$_7$H$_9$N$_4$Zn=Zn(IM)(MeIM): Calcd. C, 38.99; H, 3.74; N, 25.99; Zn, 30.34. Found C, 39.17; H, 3.39; N, 26.13; Zn, 29.98. FT-IR: (KBr 4000-400 cm-1): 3445 (br), 3139 (w), 3108 (w), 2930 (w), 2513 (w), 1637 (s), 1499 (m), 1474 (w), 1316 (w), 1174 (w), 1008 (w), 837 (w), 675 (w), 420 (s).

(ZIF-62 cag): Zn(IM)$_{1.75}$(bIM)$_{0.25}$.

0.15 mL imidazole stock solution (0.20 M, 3.0×10$^{-5}$ mol) and 0.075 mL benzimidazole stock solution (0.20 M, 1.5×10$^{-5}$ mol) was mixed together. To this solution was added 0.075 mL Zn(NO3)2.4H2O stock solution (0.20 M, 1.5×10$^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 100° C. and allowed to react solvothermally for 96 h. The product was in the form of prism-shaped single crystals.

(ZIF-64 dft): Zn(IM)$_2$.

To a 0.27 mL imidazole stock solution (0.20 M, 5.4×10$^{-5}$ mol) 0.030 mL Zn(NO$_3$)$_2$.4H$_2$O stock solution (0.20 M, 0.060×10$^{-5}$ mol) was added. After the glass plate was loaded with mixtures of stock solutions dispensed by a programmed liquid handler (Gilson, model 215), it was covered with a PTFE sheet, sealed by fastening the sheet with a metal clamp, then heated in an oven at 100° C. and allowed to react solvothermally for 72 h. The product was in the form of rod-shaped single crystals.

(ZIF-65 sod): Co(nIM)$_2$.

To a 0.25 mL 2-nitroimidazole stock solution (0.20 M, 5.0×10$^{-5}$ mol), 0.050 mL Co(NO$_3$)$_2$.6H$_2$O stock solution (0.20 M, 1.0×10$^{-5}$ mol) was added. After the glass plate was loaded with mixtures of stock solutions dispensed by a programmed liquid handler (Gilson, model 215), it was covered with a PTFE sheet, sealed by fastening the sheet with a metal clamp, then heated in an oven at 100° C. and allowed to react solvothermally for 72 h. The product was in the form of cube-shaped single crystals.

(ZIF-67 sod): Co(mIM)$_2$.

To a 0.225 mL 2-nitroimidazole stock solution (0.20 M, 4.5×10$^{-5}$ mol), 0.075 mL Co(NO$_3$)$_2$.6H$_2$O stock solution (0.20 M, 1.5×10$^{-5}$ mol) was added. After the glass plate was loaded with mixtures of stock solutions dispensed by a programmed liquid handler (Gilson, model 215), it was covered with a PTFE sheet, sealed by fastening the sheet with a metal clamp, then heated in an oven at 100° C. and allowed to react solvothermally for 72 h. The product was in the form of prism-shaped single crystals.

(ZIF-68 gme): Zn(nIM)(bIM).

0.180 mL 2-nitroimidazole stock solution (0.20 M, 3.6×10$^{-5}$ mol) and 0.060 mL benzimidazole stock solution (0.20 M, 1.2×10$^{-5}$ mol) was mixed together. To this solution was added 0.060 mL Zn(NO3)2.4H2O stock solution (0.20 M, 1.2×10$^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 100° C. and allowed to react solvothermally for 72 h. The product was in the form of yellow colored prism-shaped single crystals. Elemental analysis C$_{10}$H$_9$N$_5$O$_2$Zn=Zn(NO$_2$IM)(PhIM).(DMF)(H$_2$O)2: Calcd. C, 36.10; H, 3.33; N, 21.05. Found C, 35.47; H, 2.89; N, 21.83. Elemental analysis (activated) C$_{10}$H$_9$N$_5$O$_2$Zn=Zn(NO$_2$IM)(PhIM): Calcd. C, 40.49; H, 2.38; N, 23.62; 0, 10.79; Zn, 22.05. Found C, 40.09; H, 2.12; N, 23.60; 0, 11.44; Zn, 21.95.

(ZIF-69 gme): Zn(nIM)(5cbIM).

0.12 mL 2-nitroimidazole stock solution (0.20 M, 2.4×10$^{-5}$ mol) and 0.12 mL 5-chlorobenzimidazole stock solution (0.20 M, 2.4×10$^{-5}$ mol) was mixed together. To this solution was added 0.060 mL Zn(NO$_3$)$_2$.4H$_2$O stock solution 15 (0.15 M, 1.2×10$^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 100° C. and allowed to react solvothermally for 72 h. The product was in the form of yellow colored prism-shaped single crystals. Elemental analysis C$_{10}$H$_8$N$_4$O$_2$ClZn=Zn(NO$_2$IM)(5ClPhIM).(H$_2$O)$_4$: Calcd. C, 32.78; H, 4.44; N, 17.65. Found C, 31.89; H, 4.39; N, 17.13. Elemental analysis (activated) C$_{10}$H$_8$N$_4$O$_2$ClZn=Zn(NO$_2$IM)(5ClPhIM): Calcd. C, 36.28; H, 1.83; N, 21.16; 0, 9.67; Cl, 10.74; Zn, 19.75. Found C, 35.90; H, 1.81; N, 20.76; 0, 9.82; Zn, 19.51. FT-IR: (KBr 4000-400 cm-1): 3445 (br), 3439 (w), 3119 (w), 3088 (w), 3027 (w), 2859 (s), 2660 (m), 2523 (w), 2319 (w), 1667 (w), 1470 (w), 1364 (w), 1291 (w), 1240 (s), 1174 (w), 807 (w), 659 (m), 603 (w).

(ZIF-70 gme): Zn(IM)1.13(nIM)0.87.

0.12 mL 2-nitroimidazole stock solution (0.20 M, 2.4×10$^{-5}$ mol) and 0.12 mL imidazole stock solution (0.20 M, 2.4×10$^{-5}$ mol) was mixed together. To this solution was added 0.060 mL Zn(NO$_3$)$_2$.4H$_2$O stock solution (0.15 M, 1.2×10$^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 100° C. and allowed to react solvothermally for 72 h. The product was in the form of prism-shaped single crystals. Elemental analysis C$_6$H$_{5.13}$N$_{4.87}$O$_{1.74}$Zn=Zn(IM)$_{1.10}$(NO$_2$IM)$_{0.90}$(DMF)(H$_2$O)$_4$: Calcd. C, 35.30; H, 4.44; N, 20.59. Found C, 35.17; H, 4.39; N, 20.13. Elemental analysis (activated) C$_6$H$_{5.13}$N$_{4.87}$O$_{1.74}$Zn=Zn(IM)$_{1.10}$(NO$_2$IM)$_{0.90}$: Calcd. C, 29.93; H, 2.14; N, 28.34; 0, 11.57; Zn, 27.16. Found C, 29.77; H, 2.12; N, 28.36; 0, 11.90; Zn, 27.01. FT-IR: (KBr 4000-400 cm-1): 3445 (br), 3419 (w), 3114 (w), 2920 (w), 2869 (w), 2655 (s), 2518 (m), 2329 (w), 1678 (w), 1510 (w), 1372 (w), 1168 (w), 1102 (w), 669 (s).

(ZIF-71 rho): Zn(dcIM)$_2$.

To a 0.24 mL 4,5-dichloroimidazole stock solution (0.075 M, 1.8×10$^{-5}$ mol) 0.060 mL Zn(NO$_3$)$_2$.4H$_2$O stock solution (0.075 M, 0.45×10$^{-5}$ mol) was added. After the glass plate was loaded with mixtures of stock solutions dispensed by a programmed liquid handler (Gilson, model 215), it was covered with a PTFE sheet, sealed by fastening the sheet with a metal clamp, then heated in an oven at 85° C. and allowed to react solvothermally for 96 h. The product was in the form of block-shaped single crystals.

(ZIF-72 lcs): Zn(dcIM)$_2$.

To a 0.24 mL 4,5-dichloroimidazole stock solution (0.20 M, 4.8×10$^{-5}$ mol) 0.060 mL Zn(NO$_3$)$_2$.4H$_2$O stock solution (0.20 M, 1.2×10$^{-5}$ mol) in DEF was added. After the glass plate was loaded with mixtures of stock solutions dispensed by a programmed liquid handler (Gilson, model 215), it was covered with a PTFE sheet, sealed by fastening the sheet with a metal clamp, then heated in an oven at 65° C. and allowed to react solvothermally for almost 6 days. The product was in the form of prism shaped single crystals.

(ZIF-73 frl): $Zn(nIM)_{1.74}(dmbIM)_{0.26}$.

0.12 mL 2-nitroimidazole stock solution (0.20 M, 2.4×$10^{-5}$ mol) and 0.12 mL 5,6-dimethylbenzimidazole stock solution (0.20 M, 0.90×$10^{-5}$ mol) was mixed together. To this solution was added 0.060 mL $Zn(NO_3)_2.4H_2O$ stock solution (0.15 M, 0.90×$10^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 85° C. and allowed to react solvothermally for 72 h. The product was in the form of prism-shaped single crystals.

(ZIF-74 gis): $Zn(nIM)(dmbIM)$.

0.18 mL 2-nitroimidazole stock solution (0.20 M, 3.6×$10^{-5}$ mol) and 0.060 mL 5,6-dimethylbenzimidazole stock solution (0.20 M, 1.2×$10^{-5}$ mol) was mixed together. To this solution was added 0.060 mL $Zn(NO_3)_2.4H_2O$ stock solution (0.15 M, 0.90×$10^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 85° C. and allowed to react solvothermally for 5 days. The product was in the form of rod-shaped single crystals. Elemental analysis $C_{12}H_{13}N_5O_2Zn=Zn(NO_2IM)(5,6Me_2PhIM)$: Calcd. C, 39.28; H, 5.36; N, 28.65. Found C, 39.47; H, 4.39; N, 27.13. FT-IR: (KBr 4000-400 cm-1): 3445 (br), 3429 (w), 3108 (w), 2762 (w), 1958 (w), 1611 (s), 1469 (m), 1342 (w), 1286 (w), 1092 (w), 939 (w), 802 (w), 669 (w), 603 (s).

(ZIF-75 gis): $Co(nIM)(dmbIM)$.

0.12 mL imidazole stock solution (0.15 M, 1.8×$10^{-5}$ mol) and 0.12 mL 5,6-dimethylbenzimidazole stock solution (0.15 M, 0.90×$10^{-5}$ mol) was mixed together. To this solution was added 0.060 mL $Co(NO3)2.6H2O$ stock solution (0.15 M, 0.90×$10^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 85° C. and allowed to react solvothermally for 5 days. The product was in the form of pink colored rod-shaped single crystals.

(ZIF-76 lta): $Zn(IM)(cbIM)$.

0.15 mL imidazole stock solution (0.15 M, 2.25×$10^{-5}$ mol) and 0.075 mL 5-chlorobenzimidazole stock solution (0.15 M, 1.13×$10^{-5}$ mol) was mixed together. To this solution was added 0.075 mL $Zn(NO_3)_2.4H_2O$ stock solution (0.15 M, 1.12×$10^{-5}$ mol). After the glass plate was loaded with mixtures of stock solutions dispensed by a programmed liquid handler (Gilson, model 215), it was covered with a PTFE sheet, sealed by fastening the sheet with a metal clamp, then heated in an oven at 65° C. and allowed to react solvothermally for 5 days. The product was in the form of hexagon-shaped single crystals. Elemental analysis $C_8H_{13}N_5Zn=Zn(IM)_{1.5}(5ClPhIM)_{0.5}.(H_2O)_4$: Calcd. C, 33.96; H, 5.57; N, 18.05. Found C, 33.27; H, 5.39; N, 18.13. Elemental analysis (activated) $C_8H_{13}N_5Zn=Zn(IM)_{1.5}(5ClPhIM)_{0.5}$: Calcd. C, 39.28; H, 5.36; N, 28.65. Found C, 39.47; H, 4.39; N, 27.13. FT-IR: (KBr 4000-400 cm-1): 3445 (br), 3429 (w), 3108 (w), 2762 (w), 1958 (w), 1611 (s), 1469 (m), 1342 (w), 1286 (w), 1092 (w), 939 (w), 802 (w), 669 (w), 603 (s).

(ZIF-77 frl): $Zn(nIM)_2$.

To a 0.26 mL 2-nitroimidazole stock solution (0.20 M, 5.2×$10^{-5}$ mol) 0.060 mL $Zn(NO_3)_2.4H_2O$ stock solution (0.20 M, 1.2×$10^{-5}$ mol) was added. After the glass plate was loaded with mixtures of stock solutions dispensed by a programmed liquid handler (Gilson, model 215), it was covered with a PTFE sheet, sealed by fastening the sheet with a metal clamp, then heated in an oven at 100° C. and allowed to react solvothermally for 72 h. The product was in the form of prism-shaped single crystals.

ZIF-95 and ZIF-100 General Synthesis.

5-chlorobenzimidazole (cbIM), zinc(II) trifluoromethanesulphonate, $Zn(O_3SCF_3)_2$, anhydrous N,N-dimethylformamide (DMF), acetone and methanol were purchased from Aldrich Chemical Co.; imidazole and DMF were purchased from Fisher Scientific International, Inc. Zinc(II) nitrate tetrahydrate, $Zn(NO_3)_2.4H_2O$, was purchased from EM Science. All starting materials were used without further purifications. Weighing and transferring zinc(II) trifluoromethanesulphonate was performed in a glove box. All the other experimental operations, unless otherwise noted, were performed in air.

Single-crystal X-ray diffraction data were collected using a Bruker SMART APEX-II three-circle diffractometer equipped with a CCD (charge-coupled device) area detector operated at 1,200 W (40 kV, 30 mA) to generate Cu Kα radiation (151.5417 Å). Powder X-ray diffraction data were collected using a Bruker D8 Discover h-2 h diffractometer in reflectance Bragg-Brentano geometry at 40 kV, 40mA (1,600 W) for Cu Kα1 radiation (151.5406 Å).

Fourier transform infrared spectra (FT-IR) of samples prepared as KBr pellets were measured using a Nicolet FT-IR Impact 400 system.

Thermal gravimetric analysis was carried out using a TA Q500 thermal analysis system.

Synthesis of ZIF-95.

A solid mixture of zinc(II) nitrate tetrahydrate $(Zn(NO_3)_2.4H_2O$, 1.044 g, 4.0 mmol) and cbIM $(C_7H_5N_2Cl$, 6.106 g, 40.0 mmol) was dissolved in 295 ml DMF and 5 ml $H_2O$ in a 500 ml container. The container was capped and heated at 120° C. for 72 h to give light yellow plate crystals. The reaction mixture was allowed to cool gradually to room temperature and crystals were washed with DMF and dried in air (yield: 1.103 g, 75% based on $Zn(NO_3)_2.4H_2O$). Elemental microanalysis for $Zn(cbIM)_2$; $C_{14}H_8N_4Cl_2Zn_1$, calculated based on framework only (%): C, 45.63; H, 2.19; N, 15.20; Cl, 19.24; Zn, 17.74. Found (%): C, 46.06; H, 2.40; N, 14.38; Cl, 19.13; Zn, 18.17. FT-IR (KBr, 4,000-400 $cm^{-1}$): 3,426 (br), 3,080 (w), 2,935 (w), 2,860 (w), 1,671 (vs), 1,612 (m), 1,566 (w), 1,475 (vs), 1,393 (m), 1,347 (s), 1,291 (s), 1,261 (m), 1,240 (m), 1,194 (m), 1,130 (w), 1,104 (m), 1,067 (m), 1,011 (w), 930 (m), 853 (m), 807 (s), 726 (m), 655 (m), 599 (m), 488 (m), 431 (m).

Synthesis of ZIF-100.

Under a dry nitrogen atmosphere a solid mixture of zinc(II) trifluoromethanesulphonate $(Zn(O_3SCF_3)_2$, 1.453 g, 4.0 mmol) and cbIM (6.103 g, 40.0 mmol) was dissolved in anhydrous DMF (270 ml) in a 500 ml container. Subsequently, $H_2O$ (5.8 ml) was added, the container capped and heated in an isothermal oven at 120° C. for 48 h to give dark yellow cubic crystals. The reaction mixture was allowed to cool naturally to room temperature and the crystals were washed with DMF and dried in air. Yield: 1.012 g, 70.5% based on $Zn(O_3SCF_3)_2$. Elemental microanalysis for $Zn_{20}(cbIM)_{39}(OH)$; $C_{273}H_{157}N_{78}O_1Cl_{39}Zn_{20}$, calculated on framework only (%): C, 45.31; H, 2.19; N, 15.10; Cl, 19.11; Zn, 18.07. Found (%): C, 45.11; H, 2.18; N, 14.79; Cl, 19.19; Zn, 18.93. FT-IR (KBr, 4,000-400 $cm^{-1}$): 3,430 (br), 3,080 (m), 2,931 (m), 2,860 (w), 1,668 (vs), 1,612 (s), 1,576

(m), 1,573 (w), 1,475 (vs), 1,437 (m), 1,415 (w), 1,342 (s), 1,286 (s), 1,256 (m), 1,240 (s), 1,195 (s), 1,134 (m), 1,098 (m), 1,072 (s), 1,014 (w), 925 (s), 859 (m), 803 (s), 762 (w), 726 (s), 659 (m), 604 (s), 487 (m), 431 (m). Under these reaction conditions (metal, ligand, solvents, temperature, time, and so on), use of different counter anions (such as zinc(II) trifluoromethanesulphonate, nitrate, tetrafluoroborate, chloride) yield similar quantities of ZIF-100. However, tuning the water content of the reaction ultimately controls the yield of ZIF-100. Therefore anions are not SDAs.

Synthesis of ZIF-105:

A solid mixture of zinc(II) nitrate tetrahydrate [$Zn(NO_3)_2 \cdot 4H_2O$, 0.3132 g, 1.2 mmol] and cbIM (1.832 g, 12.0 mmol) was dissolved in 88.5 mL DMF and 1.5 mL H2O in 120 mL jar [molar ratio: $Zn(NO_3)_2$: 1.0, cbIM: 10.0, DMF: 952.5, $H_2O$: 141.4]. The jar was capped and heated in an isothermal oven at 120° C. for 72 h yielding light yellow plate crystals. The reaction was allowed to naturally cool to room temperature and crystals were washed with DMF and dried in air. Yield: 0.11 g, 25% based on $Zn(NO_3)_2.4H_2O$). Elemental microanalysis for $Zn(cbIM)_2$ ($C_{14}H_8N_4Cl_2Zn_1$) based on framework only. Calcld. (%): C, 45.63; H, 2.19; N, 15.20; Cl, 19.24; Zn, 17.74. Found (%, as synthesized): C, 44.83; H, 4.63; N, 15.79; Cl, 15.91; Zn, 15.11 formulates $Zn(ClBIm)_2$ (dimethylamine)($H_2O$), Calcd. (%): C, 44.53; H, 3.97; N, 16.22; Cl, 16.42; Zn, 15.15. Found (%, following activation and evacuation of pores): C, 46.06; H, 2.40; N, 14.38; Cl, 19.13; Zn, 18.17.

FT-IR (KBr, 4000-400 cm-1): 3426 (br), 3080 (w), 2935 (w), 2860 (w), 1671 (vs), 1612 (m), 1566 (w), 1475 (vs), 1393 (m), 1347 (s), 1291 (s), 1261 (m), 1240 (m), 1194 (m), 1130 (w), 1104 (m), 1067 (m), 1011 (w), 930 (m), 853 (m), 807 (s), 726 (m), 655 (m), 599 (m), 488 (m), 431 (m).

Activation of ZIF-100 and -105: The sample for the gas adsorption measurement was prepared as follows. The as-synthesized sample of ZIF-100 was immersed in anhydrous acetonitrile in glove box for 3 days; during the exchange the acetonitrile was refreshed three times. The resulting acetonitrile-exchanged sample of ZIF-100 in acetonitrile was transferred to a quartz cell in glove box and the solvent was roughly decanted using a pipette. The wet sample then was evacuated at 50° for 10 h and then 100° for 12 h to yield an activated sample, which could then be used for gas adsorption measurements and separation tests.

Similarly ZIF-105 was immersed in anhydrous acetone in glove box for 3 days and was refreshed three times. After transferring to a quartz cell in glove box, solvent was roughly decanted using a pipette. The wet sample was then then was evacuated at 50° for 6 h and then 100° for 12 h to yield an activated sample, which could then be used for gas adsorption measurements and separation tests.

Powder X-ray diffraction (PXRD) data were collected using a Bruker D8-Advance θ-2θ diffractometer in reflectance Bragg-Brentano geometry employing Ni filtered Cu Kα line focused radiation at 1600 W (40 kV, 40 mA) power and equipped with a Na(Tl) scintillation detector fitted a 0.2 mm radiation entrance slit. All samples were ground to ensure mono-dispersity in the bulk, then mounted onto a zero-background sample holder by dropping powders from a wide-blade spatula and then leveling the sample surface with a razor blade. The best counting statistics were achieved by using a 0.02° 2θ step scan from 1.5-60° with an exposure time of 10 s per step.

Comparison of positions and indices of diffraction lines in the experimental and simulated PXRD patterns of ZIF-1(crb). Deviations from perfect correspondence primarily arise from difference in data collection temperatures (cryogenic for single crystal data and room temperature for bulk powder):

| Observed PXRD | | Simulated PXRD | | Indices |
|---|---|---|---|---|
| 2-Theta | d | 2-Theta | d | hkl |
| 10.16 | 8.698 | 10.18 | 8.684 | −101 |
| 11.19 | 7.899 | 11.71 | 7.548 | −1-11 |
| 11.93 | 7.384 | 11.98 | 7.384 | 002 |
| 12.96 | 6.825 | 13.05 | 6.781 | 021 |
| 13.26 | 6.674 | 13.31 | 6.647 | 012 |
| 15.02 | 5.893 | 15.12 | 5.852 | −112 |
| 15.39 | 5.753 | 15.44 | 5.733 | −1-21 |
| 16.42 | 5.394 | 16.48 | 5.373 | 121 |
| 16.64 | 5.323 | 16.69 | 5.307 | 022 |
| 17.23 | 5.142 | 17.19 | 5.155 | 112 |
| 18.34 | 4.835 | 18.41 | 4.815 | 200 |
| 25.04 | 3.554 | 25.08 | 3.548 | 140 |

Activation of ZIF-95 and ZIF-100.

As-synthesized samples of ZIF-95 were immersed in anhydrous acetone in a glove box for 3 days; during the exchange the acetone was refreshed three times. The resulting acetone-exchanged sample of ZIF-95 was transferred as a suspension to a quartz cell in a glove box and the solvent was decanted. The wet sample was then evacuated (1023 torr) at 50° C. for 10 h then at 100° C. for 12 h. ZIF-100 was identically activated, except that anhydrous methanol was used as the exchange solvent.

Crystallographic analysis of ZIF-95 and -100. Crystallographic formulation of ZIF-100 reflects the fact some cbIM ligands are positionally disordered requiring modeling of two C1 sites at the price of modeling H-sites. Modeling these disorders as freely varying entities, and thereby leading to a chemically accurate formulation, imposed the need to apply numerous restraints to sustain a stable refinement. The unrestrained refined structure (which is a true reflection of the data) rather than a highly restrained one is provided, with the understanding as to the origin of the incongruent formulation.

For ZIF-95 some cbIM ligands spanning mirror plans could not be fully resolved due to the lower resolution of the dataset and disorder present in the structure. However, an average orientation of these ligands could extracted from F-maps, therefore atoms were assigned to these difference peaks and their positions restrained for 30 refinement cycles, and ultimately their thermal parameters and coordinates were locked upon settling into an orientation for cbIM. The degree of disorder here precluded reliable identification of all C1 atoms; in particular, for those bonded to C4 and C60. Unfortunately stable refinements with a C1 atom in these positions were precluded in absence of a large number of restraints, and thus this atom was not included in the structure reported for ZIF-95. As was opted for ZIF-100, the unrestrained structure rather than a highly restrained one is reported, with the understanding as to the origin of the incongruent formulation. Bond distance restraints were employed for other non-disordered components of the framework that bridge mirror planes. In particular we note that the positions of C58, C59, and C60 are refined in positions revealed by difference F-maps, which represent a single orientation of a disorder which evolve in space group symmetry to form inaccurate bonding interactions.

Exhaustive examination of successive F-maps did not reveal improved positions for this cbIM ligand. Listed here are the idealized positions (in factional coordinates; x, y, z) for this ligand: C57: 0.5000 0.0834 0.0529; C58: 0.4837 0.1261 0.0452; C59: 0.4638 0.1537 0.0403; C60: 0.4842 0.1861 0.0357; C1: 0.5349 0.2309 0.9714.

TABLE S1

Crystal data and structure refinement for ZIF-100, for atomic coordinates, equivalent isotropic displacement parameters, bond length, angles and anisotropic displacement parameters please check the CIF (CCDC code 668215).

| | |
|---|---|
| Empirical formula | C133 H67.48 Cl19 N38 O32.25 Zn10 |
| Formula weight | 4040.98 |
| Temperature | 153(2) K |
| Wavelength | 1.54178 Å |
| Crystal system | Cubic |
| Space group | I m-3 |
| Unit cell dimensions | a = 71.9797(4) Å α = 90° |
| | b = 71.9797(4) Å β = 90° |
| | c = 71.9797(4) Å γ = 90° |
| Volume | 372932(4) Å$^3$ |
| Z | 48 |
| Density (calculated) | 0.864 Mg/m$^3$ |
| Absorption coefficient | 2.701 mm$^{-1}$ |
| F(000) | 96599 |
| Crystal size | 0.075 × 0.075 × 0.75 mm$^3$ |
| Theta range for data collection | 0.87 to 45.23° |
| Index ranges | −66 <= h <= 66, −64 <= k <= 63, −66 <= l <= 65 |
| Reflections collected | 783540 |
| Independent reflections | 25973 [R(int) = 0.2642] |
| Completeness to theta = 45.23 | 98.6% |
| Absorption correction | None |
| Refinement method | Full-matrix least-squares on F$^2$ |
| Data/restraints/parameters | 25973/0/786 |
| Goodness-of-fit on F$^2$ | 1.579 |
| Final R indices [I > 2sigma(I)] | R1 = 0.1798, wR2 = 0.4315 |
| R indices (all data) | R1 = 0.3080, wR2 = 0.5019 |
| Largest diff. peak and hole | 1.052 and −0.786 e. Å$^{-3}$ |

TABLE S2

Crystal data and structure refinement for ZIF-95, for atomic coordinates, equivalent isotropic displacement parameters, bond length and angles please check the CIF (CCDC code 668214).

| | |
|---|---|
| Empirical formula | C56 Cl7.50 N16 O8.50 Zn4 |
| Formula weight | 1560.1355 |
| Temperature | 153 K |
| Wavelength | 1.54178 Å |
| Crystal system | Tetragonal |
| Space group | I 4/m m m |
| Unit cell dimensions | a = 38.7657(4) Å α = 90° |
| | b = 38.7657(4) Å β = 90° |
| | c = 56.4541(14) Å γ = 90° |
| Volume | 84838(2) Å$^3$ |
| Z | 32 |
| Density (calculated) | 0.977 Mg/m$^3$ |
| Absorption coefficient | 0.421 mm$^{-1}$ |
| F(000) | 24432 |
| Crystal size | 0.300 × 0.150 × 0.050 mm$^3$ |
| Theta range for data collection | 1.38 to 30.91° |
| Index ranges | −25 <= h <= 25, −25 <= k <= 25, −37 <= l <= 37 |
| Reflections collected | 77043 |
| Independent reflections | 3666 [R(int) = 0.1660] |
| Completeness to theta = 30.29 | 100.00% |
| Absorption correction | None |
| Refinement method | Full-matrix least-squares on F2 |
| Data/restraints/parameters | 3583/3/296 |
| Goodness-of-fit on F$^2$ | 1.815 |
| Final R indices [I > 2sigma(I)] | R1 = 0.1699, wR2 = 0.2750 |
| R indices (all data) | R1 = 0.1699, wR2 = 0.2766 |
| Absolute structure parameter | 0 |

Gas Adsorption and Separation Measurements.

Low-pressure gas adsorption experiments (up to 850 torr) were carried out on a Quantachrome AUTOSORB-1 automatic volumetric instrument. Ultrahigh-purity-grade gases were used in all adsorption measurements. The $N_2$ (for ZIF-95, 77 K) and Ar (for ZIF-100, 87 K) isotherms were measured using a liquid nitrogen and an argon bath, respectively. $CO_2$, $CH_4$, CO and $N_2$ isotherms were also tested for both ZIF-95 and ZIF-100 at 273 and 298 K, respectively.

ZIF-95.

An apparent surface area of 1,240 m$^2$ g$^{-1}$ (Langmuir, the linearity of fitting, R50.9999) was obtained by using the data points on the adsorption branch of the $N_2$ isotherm in the range P/P050.1-0.35. A BET surface area of 1,050 m$^2$ g$^{-1}$ was obtained by using P/P050.03-0.08. A micropore volume of 0.43 cm$^3$ g$^{-1}$ was obtained by applying non-local density functional theory (NLDFT) with a N2-zeolites and silica model on the adsorption branch (the fitting error was 0.155%).

ZIF-100.

An apparent surface area of 780 m$^2$ g$^{-1}$ (R50.9998) was obtained by using the data points on the adsorption branch of the Ar isotherm in the range P/P050.1-0.3. A BET surface area of 595 m$^2$ g$^{-1}$ was obtained by using P/P050.03-0.09. A micropore volume of 0.37 cm$^3$ g$^{-1}$ was obtained by applying NLDFT with an Ar-zeolites and silica model on the adsorption branch (the fitting error was 0.095%).

The gas-separation properties of ZIF-95 and ZIF-100 were tested by breakthrough experiments using a $CO_2/CH_4$, $CO_2/N_2$ or $CO_2/CO$ (about 50:50 v/v) gas mixture. 1.2 g of activated ZIF-95 and 1.1 g of activated ZIF-100 were packed into a stainless-steel column (0.46 cm inner diameter and 8 cm length) in a glove box. The columns were then attached to gas-separation apparatus. Helium gas was used to initially purge the sample columns. All the experiments were carried out at room temperature. The gases (20 p.s.i.) were dosed into the column at a flow rate of 20 ml min 21. The relative amounts of the gases passing through the column were monitored on a Hiden Analytical HPR20 gas analysis system detecting ion peaks atm/z1544 ($CO_2$), 16 ($CH_4$), 28 ($N_2$), 12 (CO).

Figure 3B:
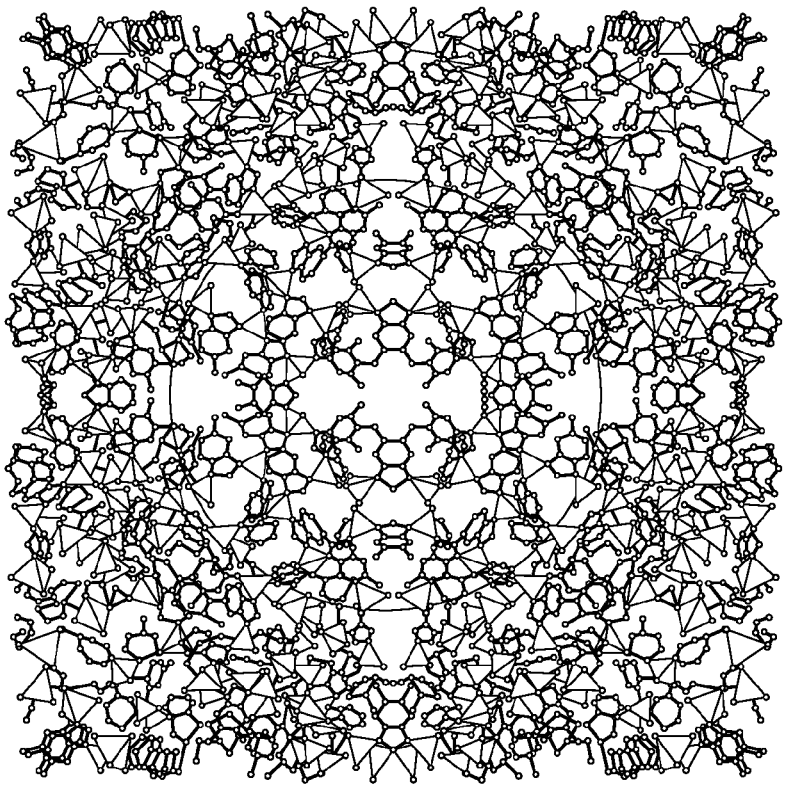
FIG. 3A-B shows a diagram of ZIF-100. Panel A shows a stick-ball diagram for ZIF 100, Blue: 4-N-coordinated Zn; Yellow: 3-N-coordinated Zn. Panel B shows the largest cage in ZIF 100, Blue tetrahedra: $ZnN_4$; Red tetrhedra: $ZnN_3OH$; Spheres, black: carbon; Orange: nitrogen; Green: chlorine; Light red: oxygen, hydrogens are omitted for clarity.
Figure 3A:
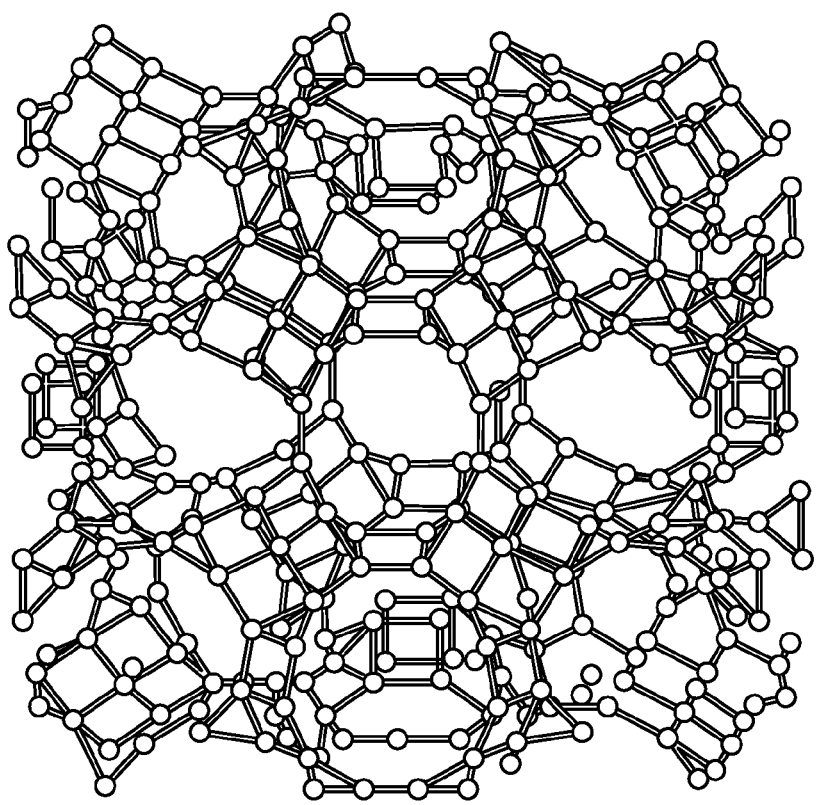

ZIF-100 and -105 were solvothermally synthesized by combining cbIM with $Zn(CF_3SO_3)_2$ or $Zn(NO_3)_2 \cdot 4H_2O$, respectively, in N,N-dimethylformamide (DMF) and heating at 120° C. in 100 mL glass jars for 48-72 h. Gram quantities of each material were isolated as phase pure crystals having compositions of $Zn_{20}(cbIM)_{39}(OH)$ (ZIF-100) or $Zn(cbIM)_2$ (ZIF-105) formulated on the basis of X-ray crystallography, and elemental microanalysis, MAS-NMR following evacuation of their pores. As will be described below the structures ZIF-100 (FIG. 3) and ZIF-105 (FIG. 4) are striking and beyond those of known zeolites.

The structures of both ZIF-100 and -105 were determined by X-ray diffraction studies using single crystals selected from phase-pure products of synthesis described above. Initial X-ray (CuK, =1.5417 Å) photographs of the crystals clearly revealed dense diffraction patterns indicating very large units cells. Assessing the metric symmetry of the patterns revealed cubic (Im-3, a=71.9797(4) Å) and tetragonal (I4/m, a=b=38.7657(4), c=56.454(1) Å) unit cells for ZIF-100 and -105 respectively. Remarkably, the unit cell volume of ZIF-100 is 372,932(4) Å$^3$, and its size is well beyond (>50%) that already encountered in small-molecule inorganic, organic, and metal-organic framework (MOF) crystallography and is, to the best of our research, the largest chemical crystal structure known.

Figure 5:
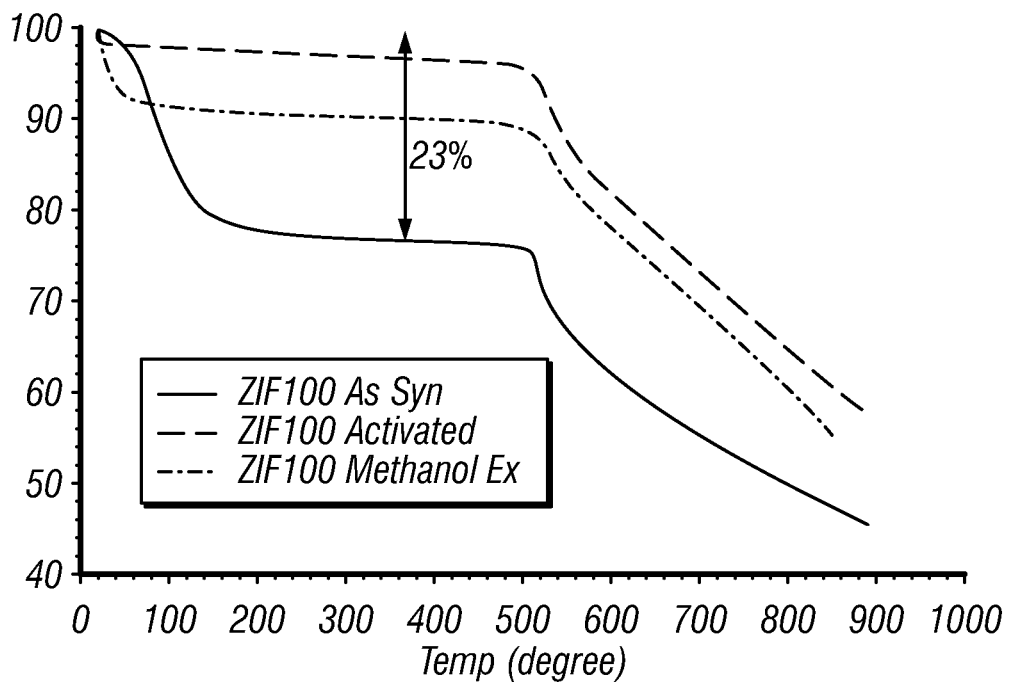
FIG. 5 shows a TGA of ZIF-100.
Figure 6:
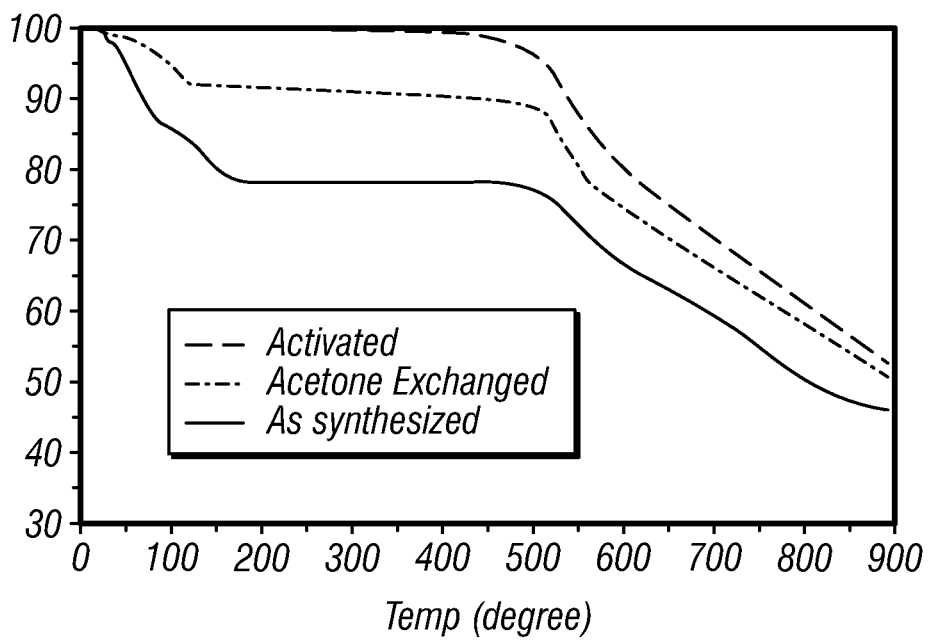
FIG. 6 shows a TGA of ZIF-105.
Figure 7:
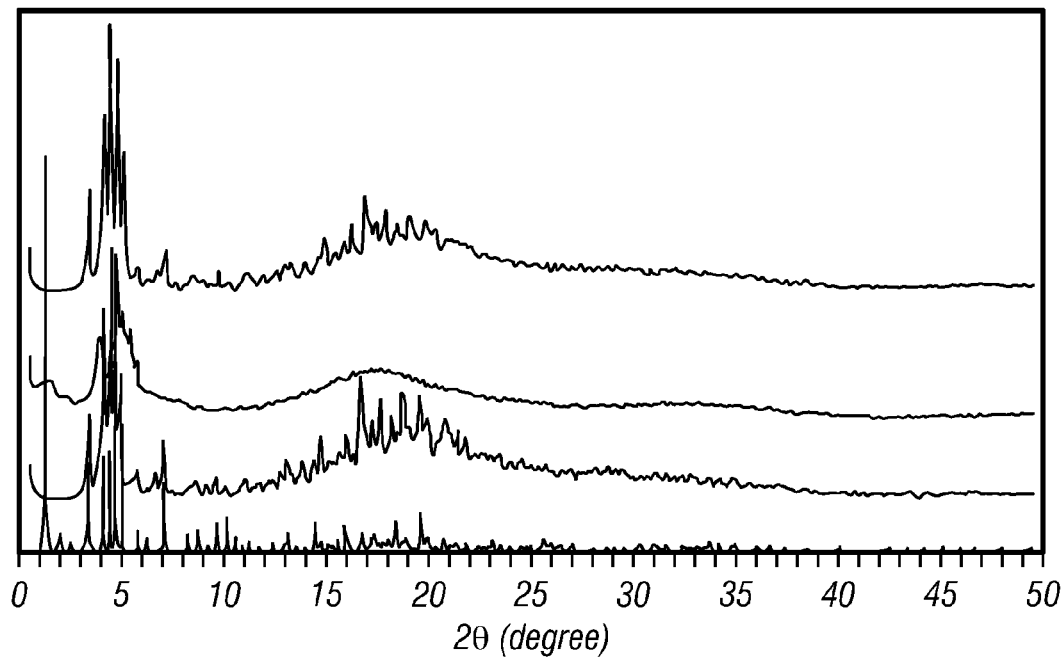
FIG. 7 shows a powder x-ray diffraction pattern for ZIF 100. Black: Simulated pattern from single X-ray diffraction data; Red: As synthesized material; Green: Activated sample; Blue: Samples soaked back to fresh DMF.
Figure 8:
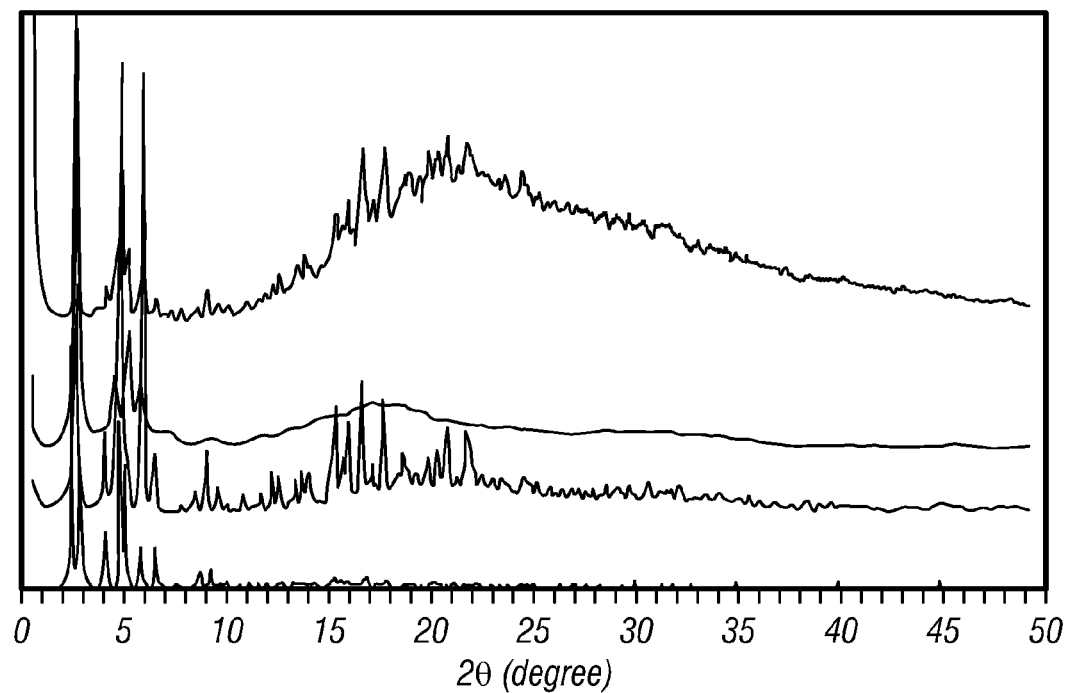
FIG. 8 shows a powder x-ray diffraction pattern for ZIF 105. Black: Simulated pattern from single X-ray diffraction data; Red: As synthesized material; Green: Activated sample; Blue: Samples soaked back to fresh DMF.
Figures 9, 10:
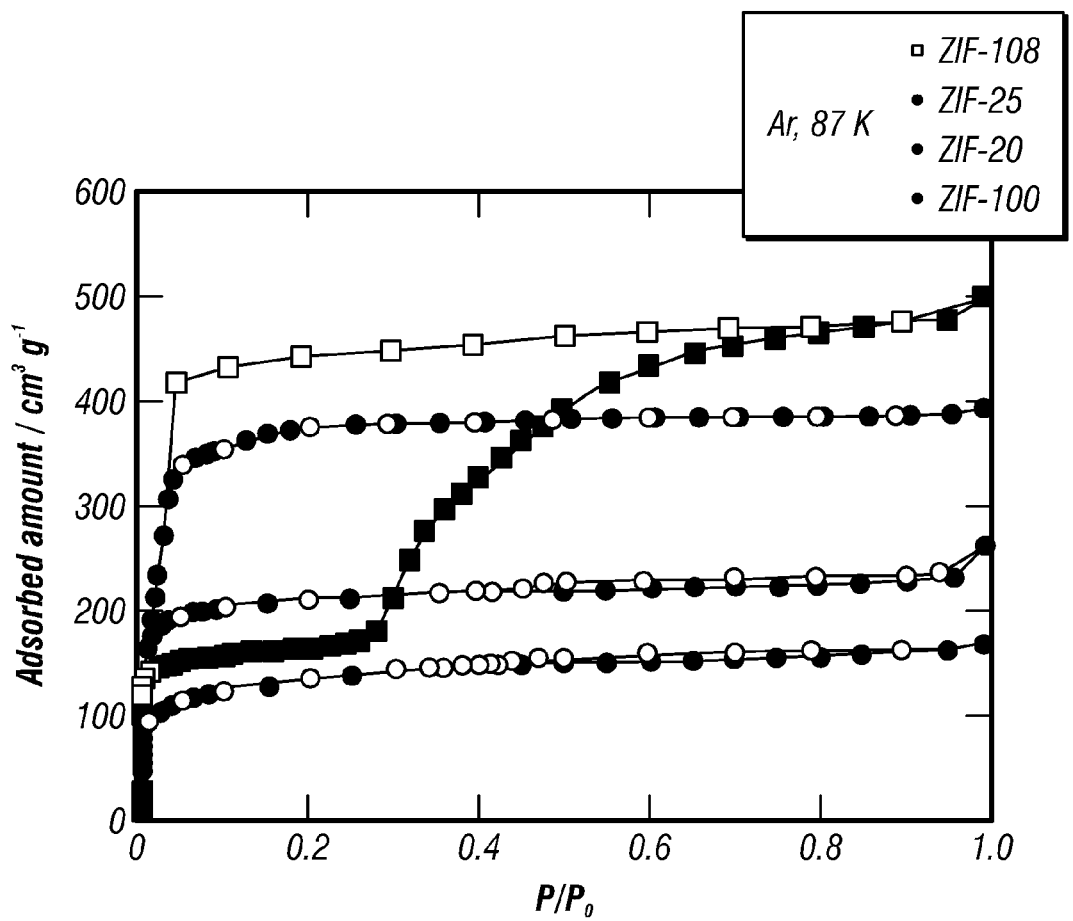
FIG. 9 shows low pressure Ar isotherms for ZIFs.
FIG. 10 shows Ar uptake data for ZIFs.
Figure 11:
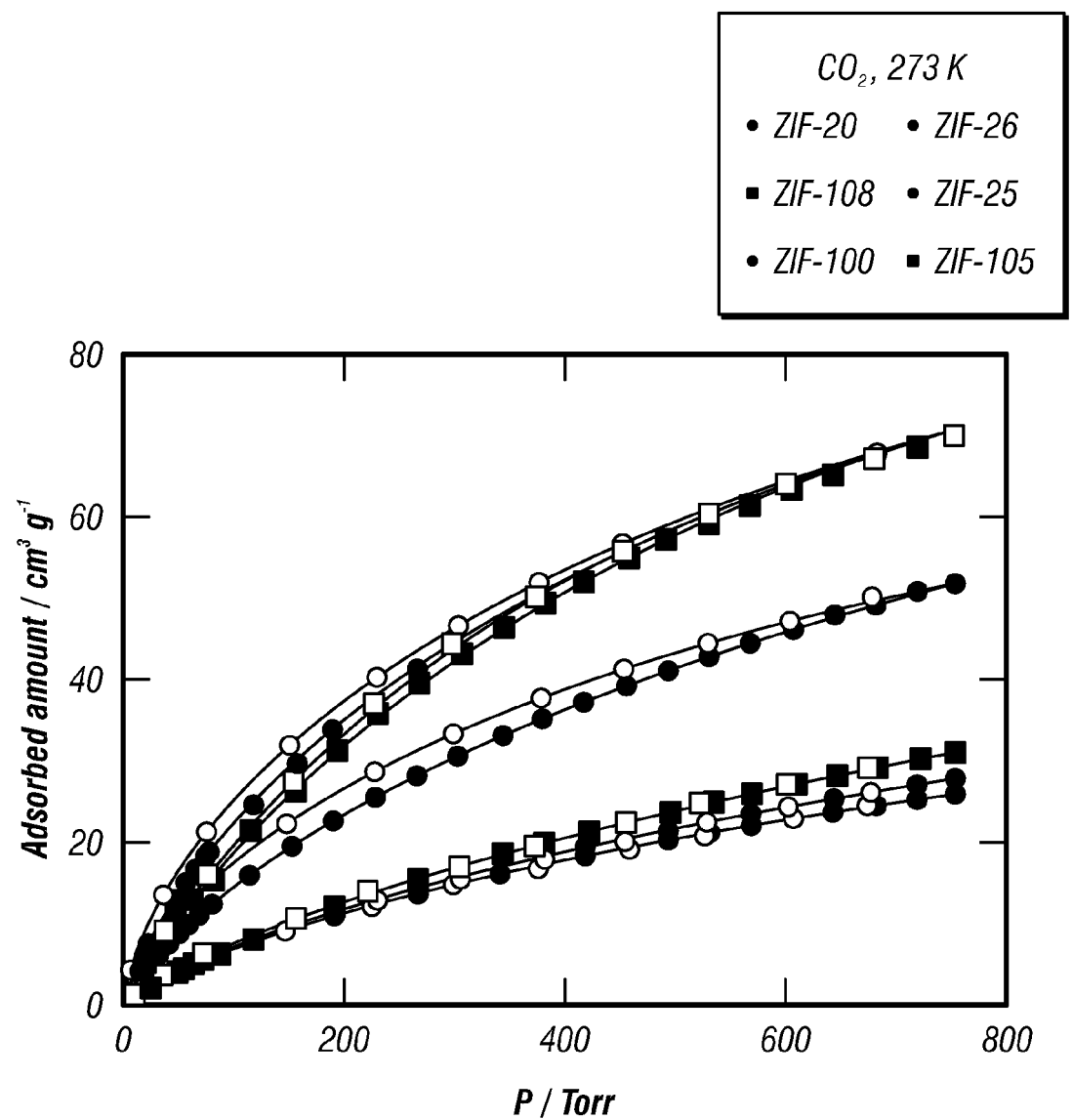
FIG. 11 shows low pressure $CO_2$ isotherms for ZIFs
Figure 13:
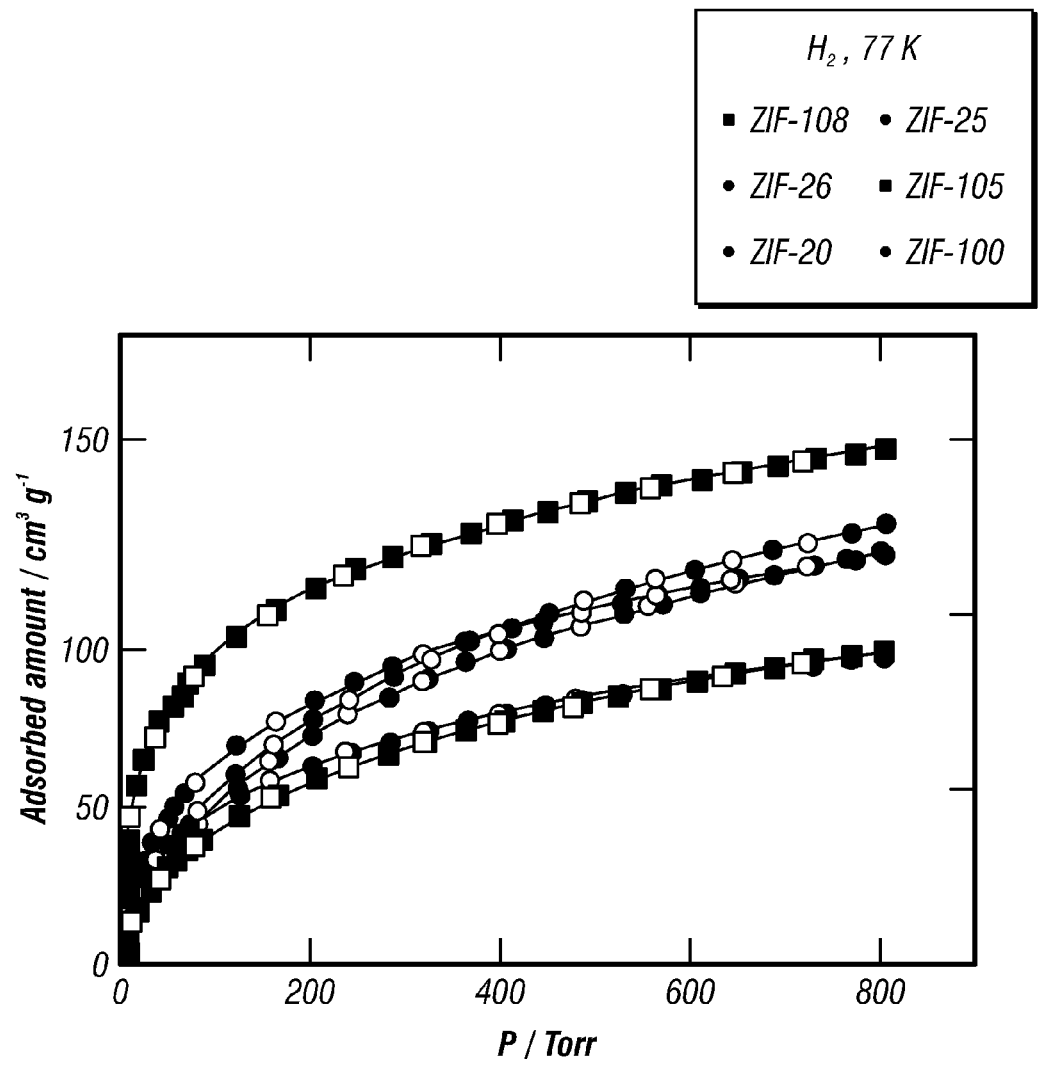
FIG. 13 shows low pressure $H_2$ isotherms for ZIFs.
Figure 15:
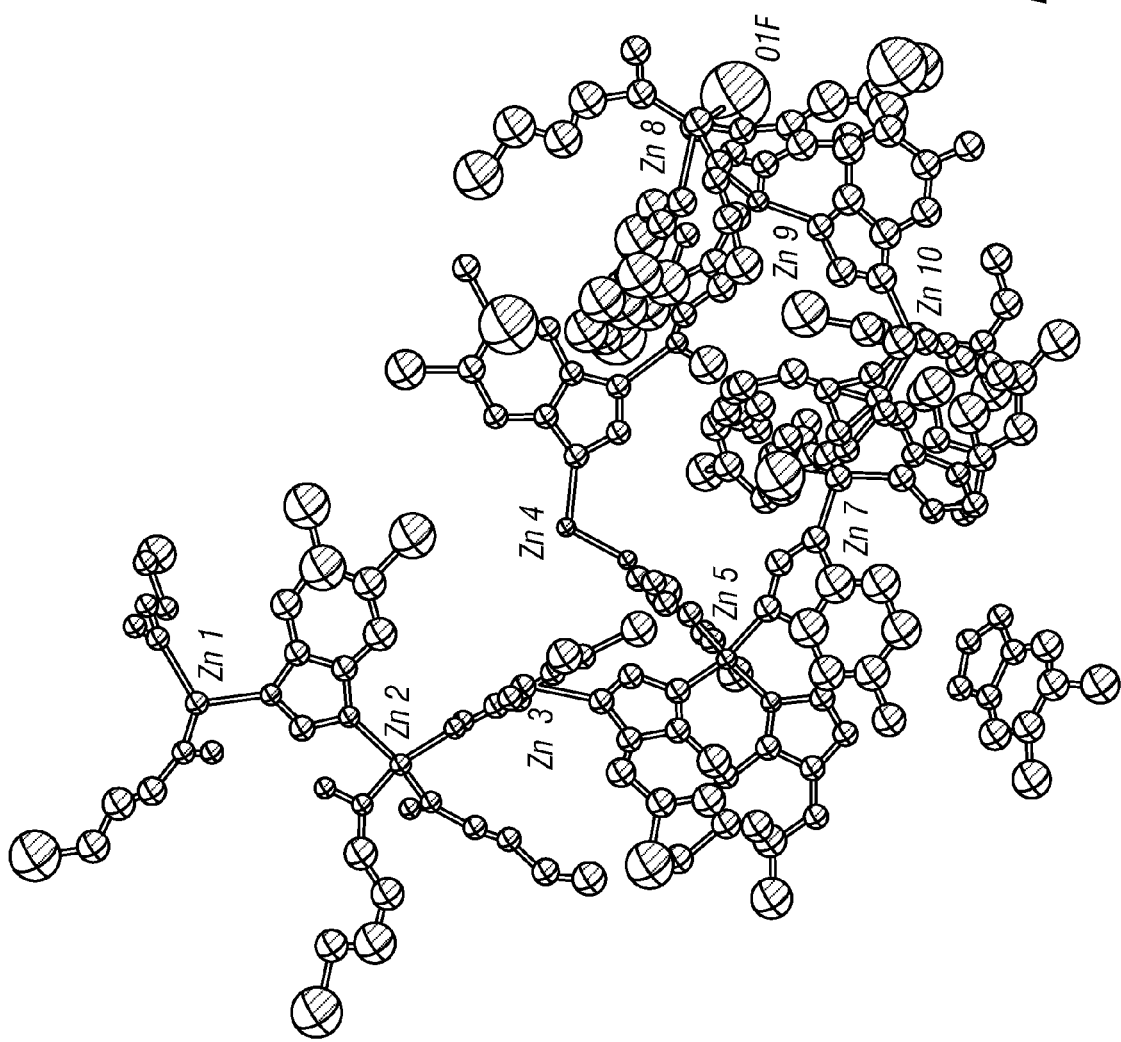
FIG. 15 shows an ORTEP for asymmetric unit of ZIF-100, with Zn atoms and framework oxygen (O1F) labeled from two different orientations. For clarity H atoms, solvent O atoms, and remaining labels are omitted. We refer readers to the CIF for full labeling scheme. Ellipsoids are displayed at the 20% probability level.
Figure 15:
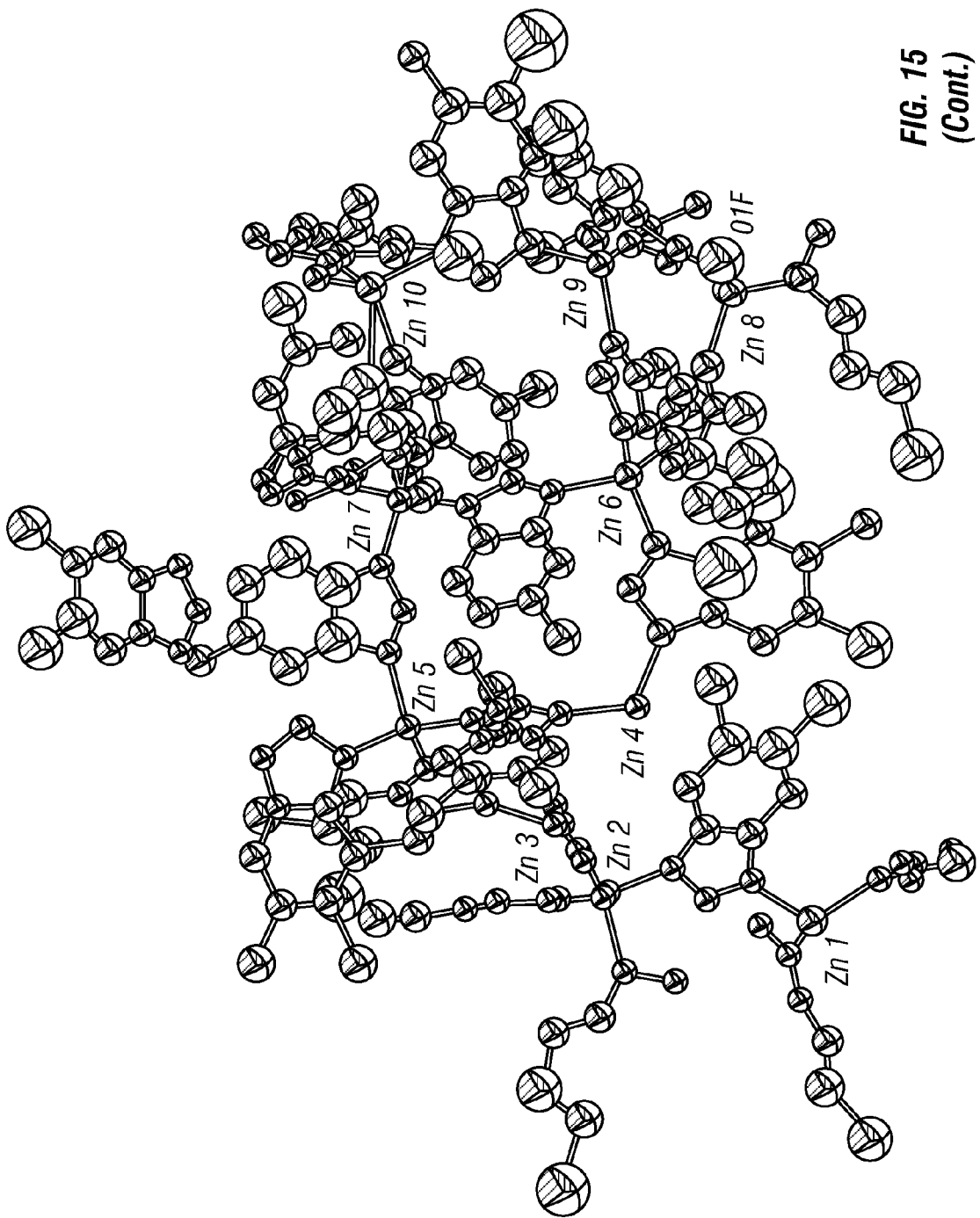
Figure 16:
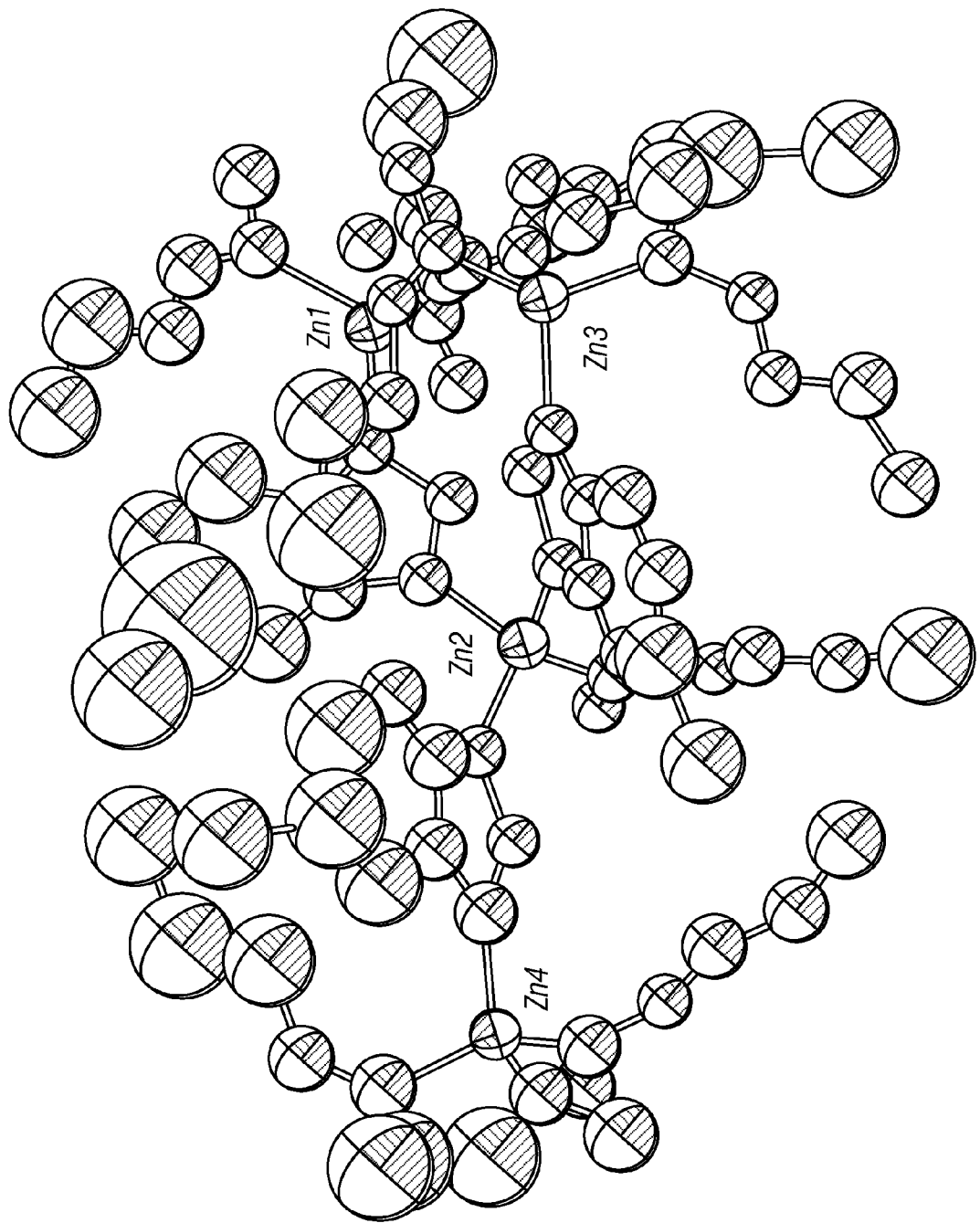
FIG. 16 shows an ORTEP for asymmetric unit of ZIF-95, with Zn atoms labeled. For clarity H atoms, solvent O atoms, and remaining labels are omitted. We refer readers to the CIF for full labeling scheme. Ellipsoids are displayed at the 20% probability level.
Figure 17:
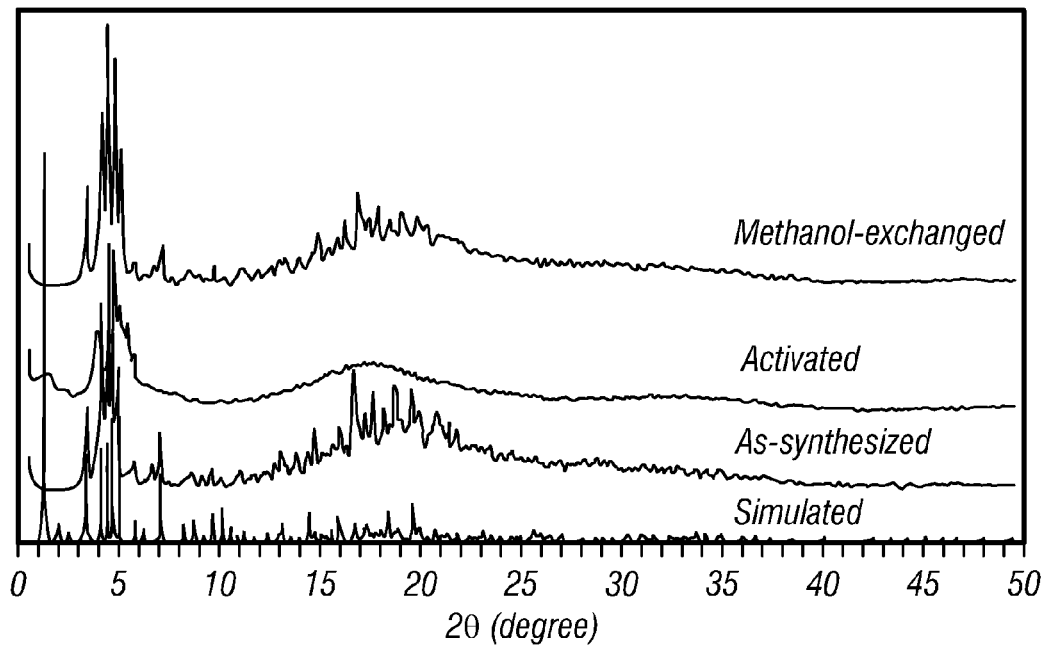
FIG. 17 shows a comparison of the experimental PXRD patterns of as-synthesized, methanol-exchanged and activated ZIF-100 along with the simulated pattern from single-crystal X-ray data.
Figure 18:
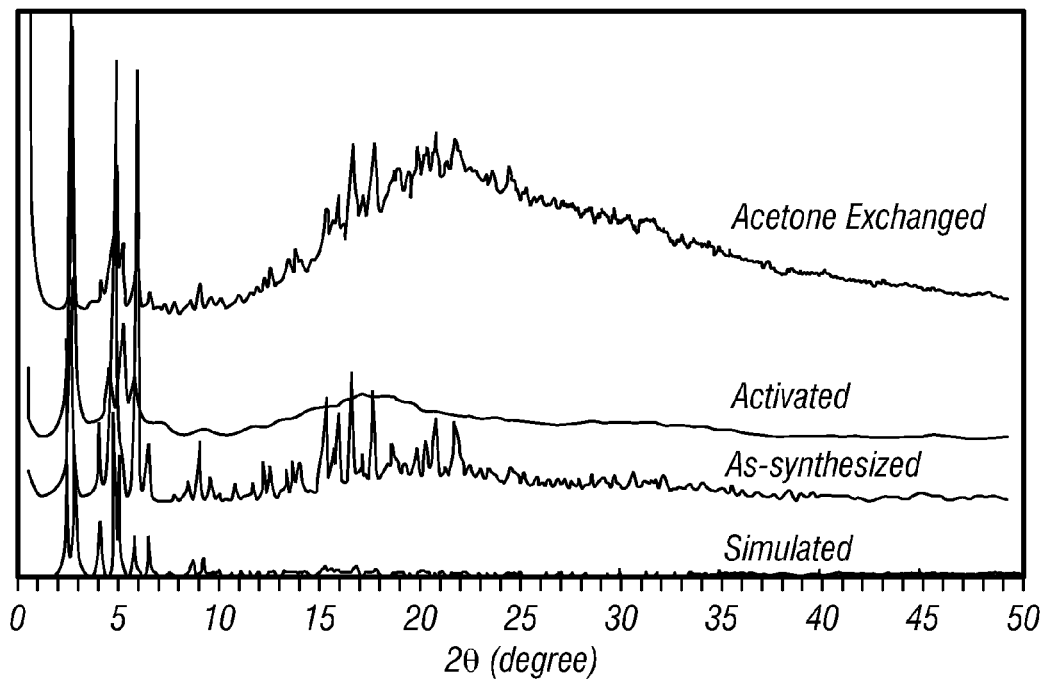
FIG. 18 Comparison of the experimental PXRD patterns of as-synthesized, methanol-exchanged and activated ZIF-95 along with the simulated pattern from single-crystal X-ray data.
Figure 19:
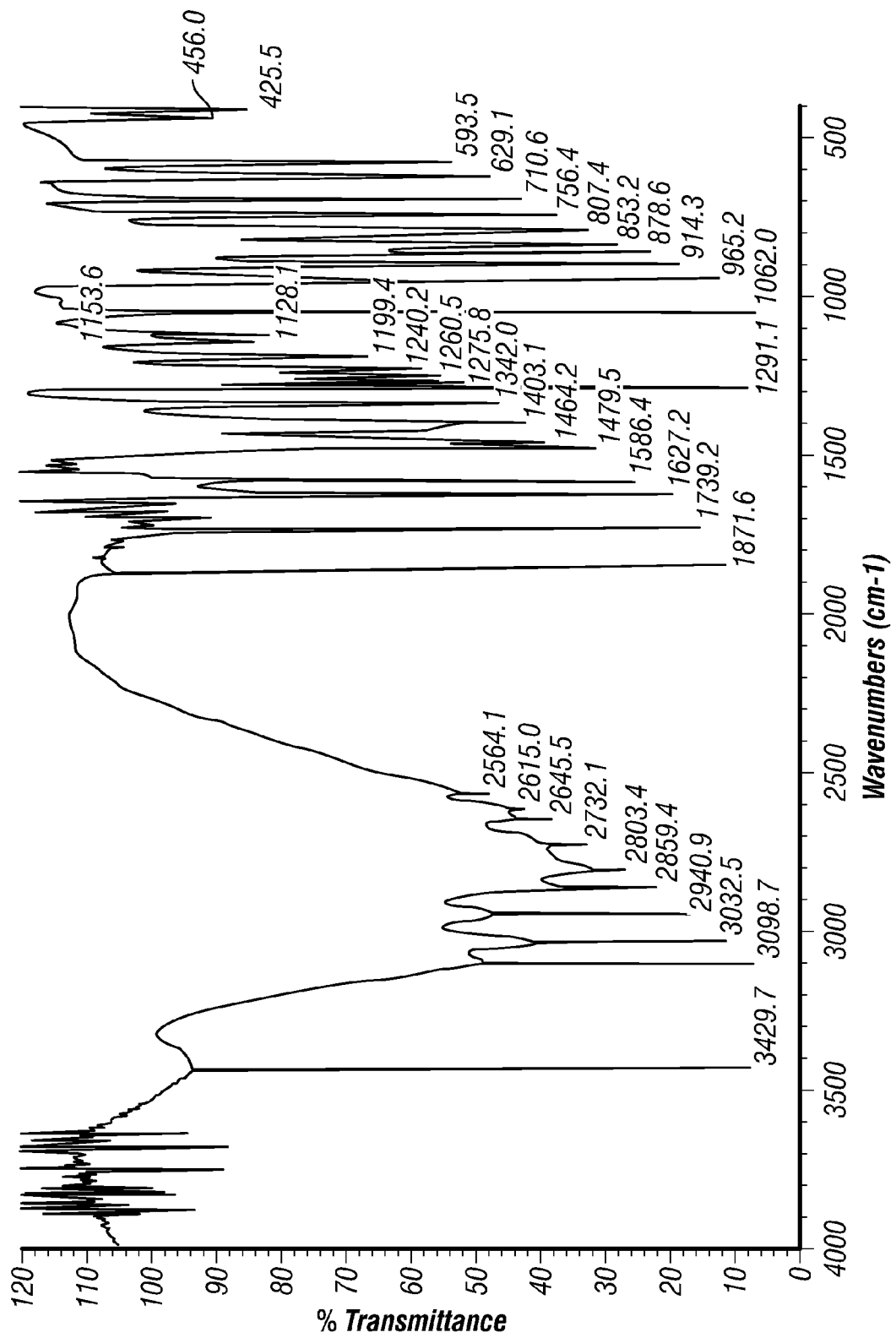
FIG. 19 shows FT-IR spectrum of 5-chlorobenzimidazole.
Figure 20:
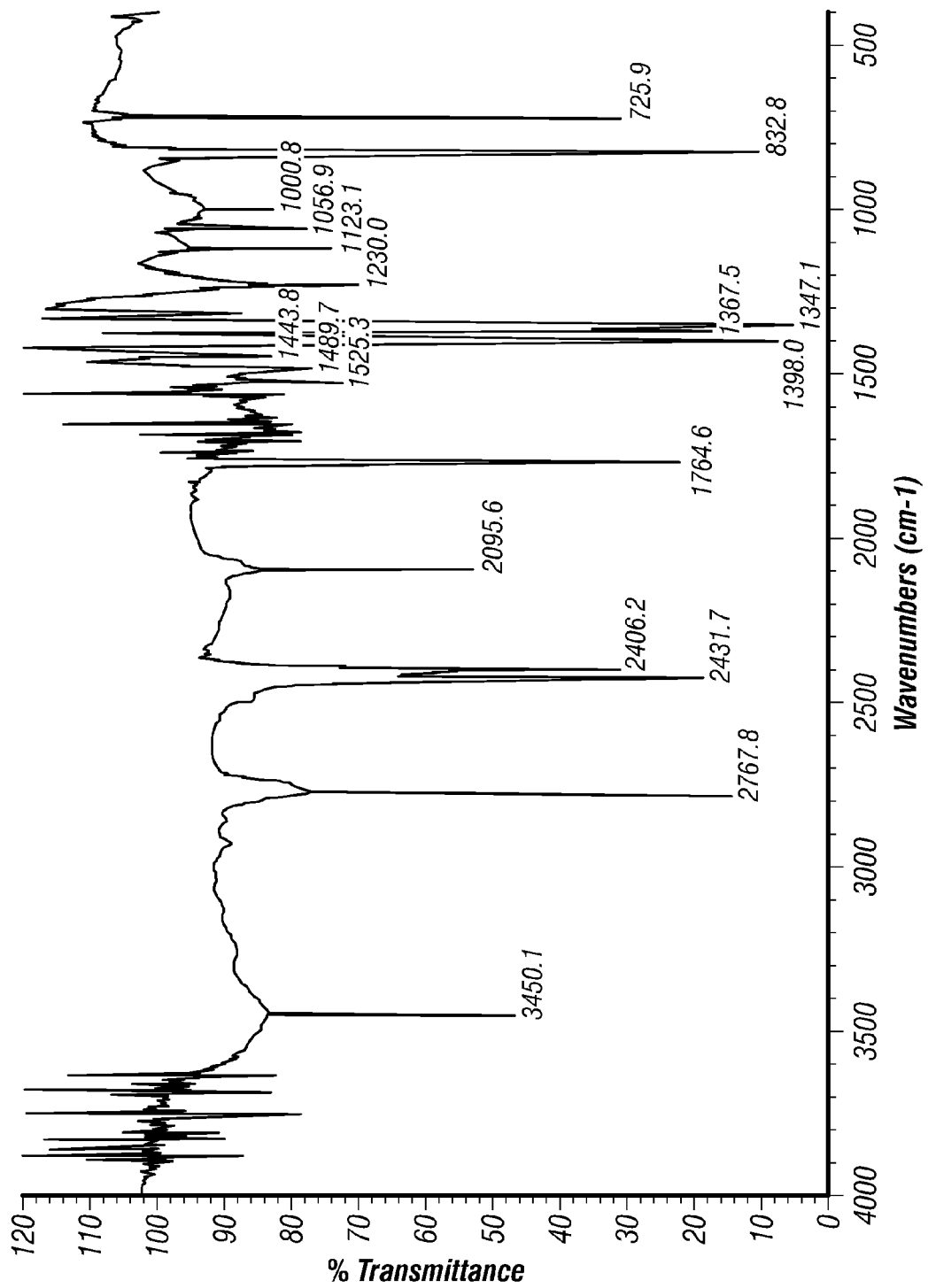
FIG. 20 shows FT-IR spectrum of zinc nitrate tetrahydrate.
Figure 21:
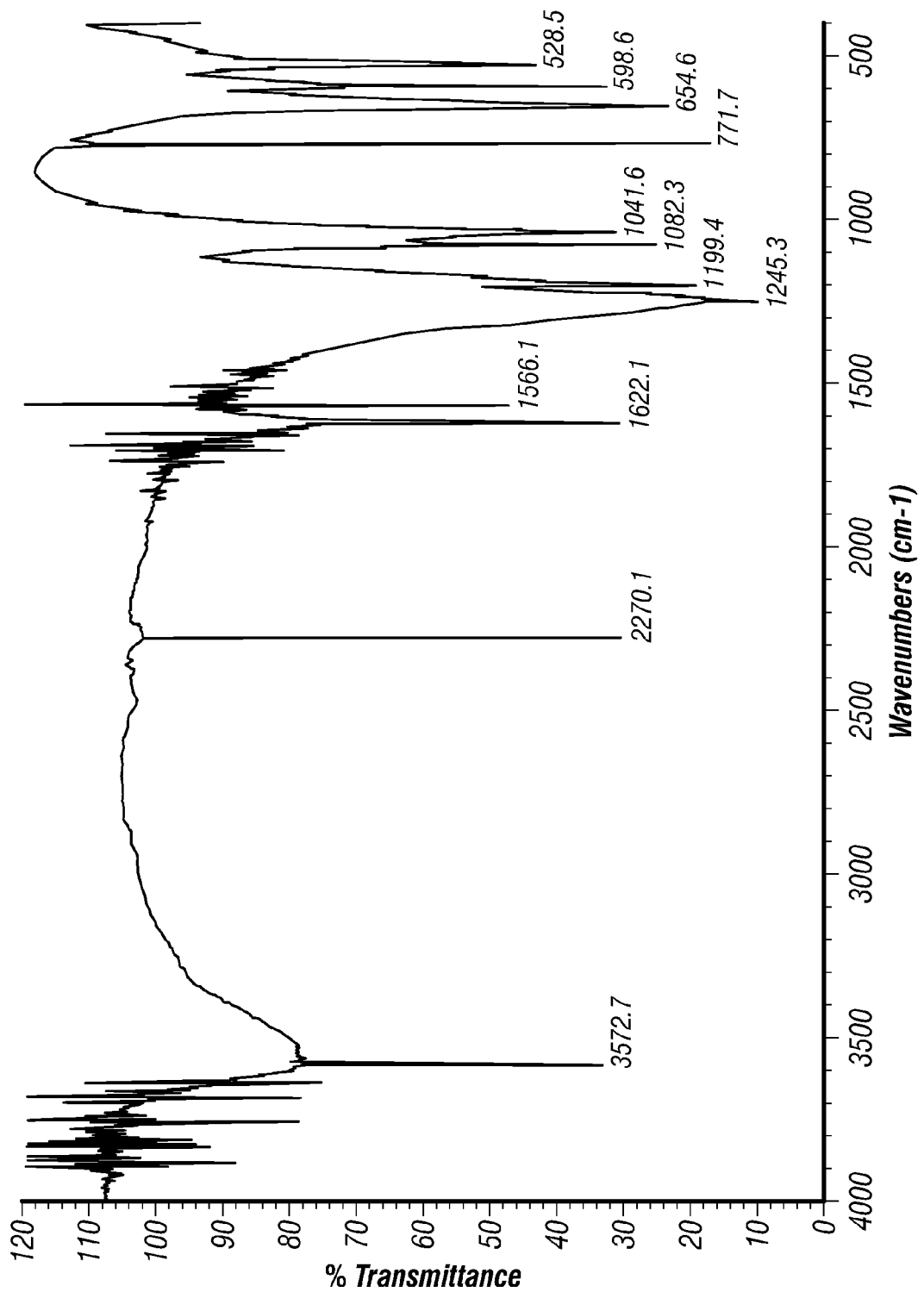
FIG. 21 shows FT-IR spectrum of zinc trifluoromethanesulfonate.
Figure 22:
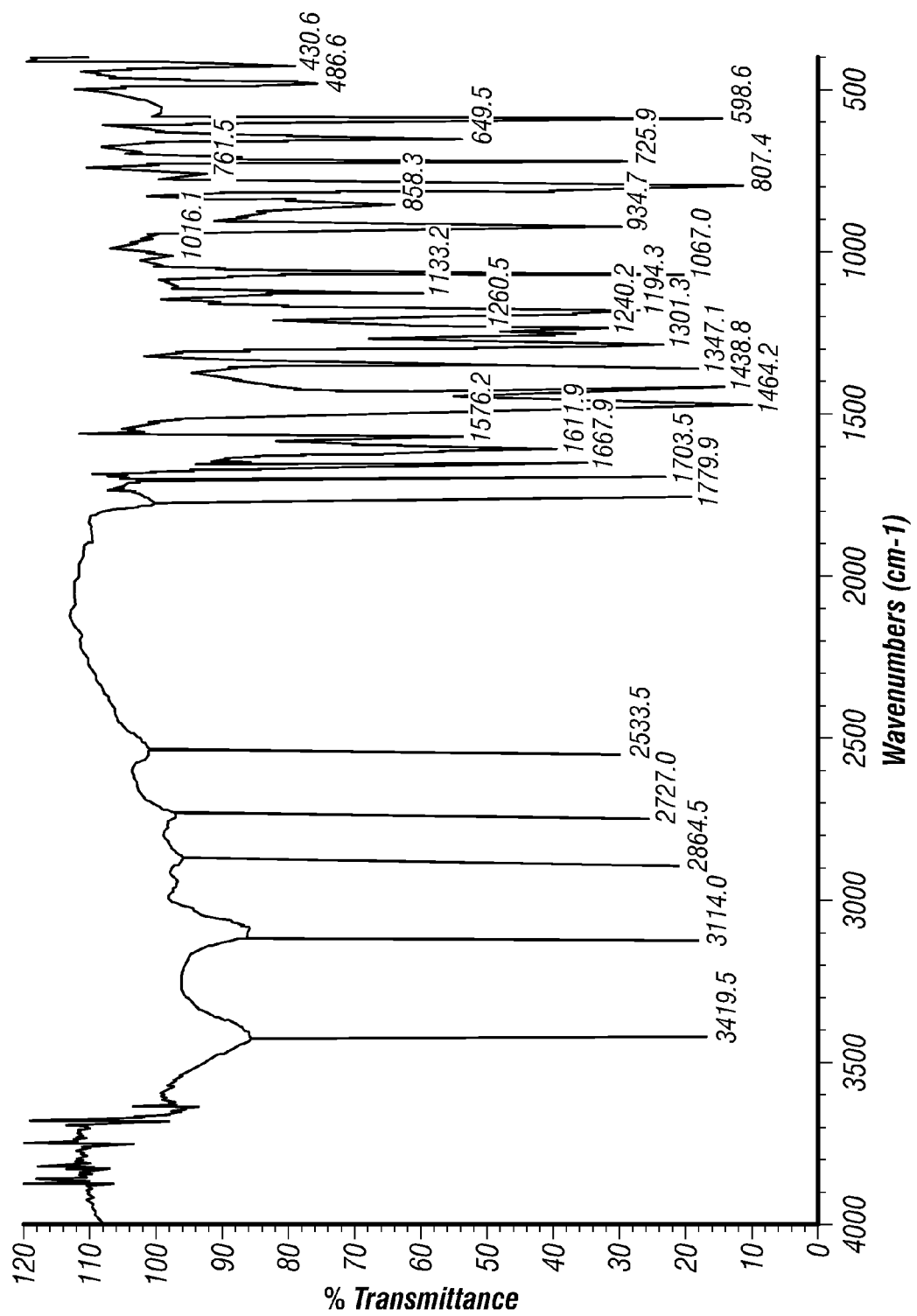
FIG. 22 shows FT-IR spectrum of as-synthesized ZIF-100.
Figure 23:
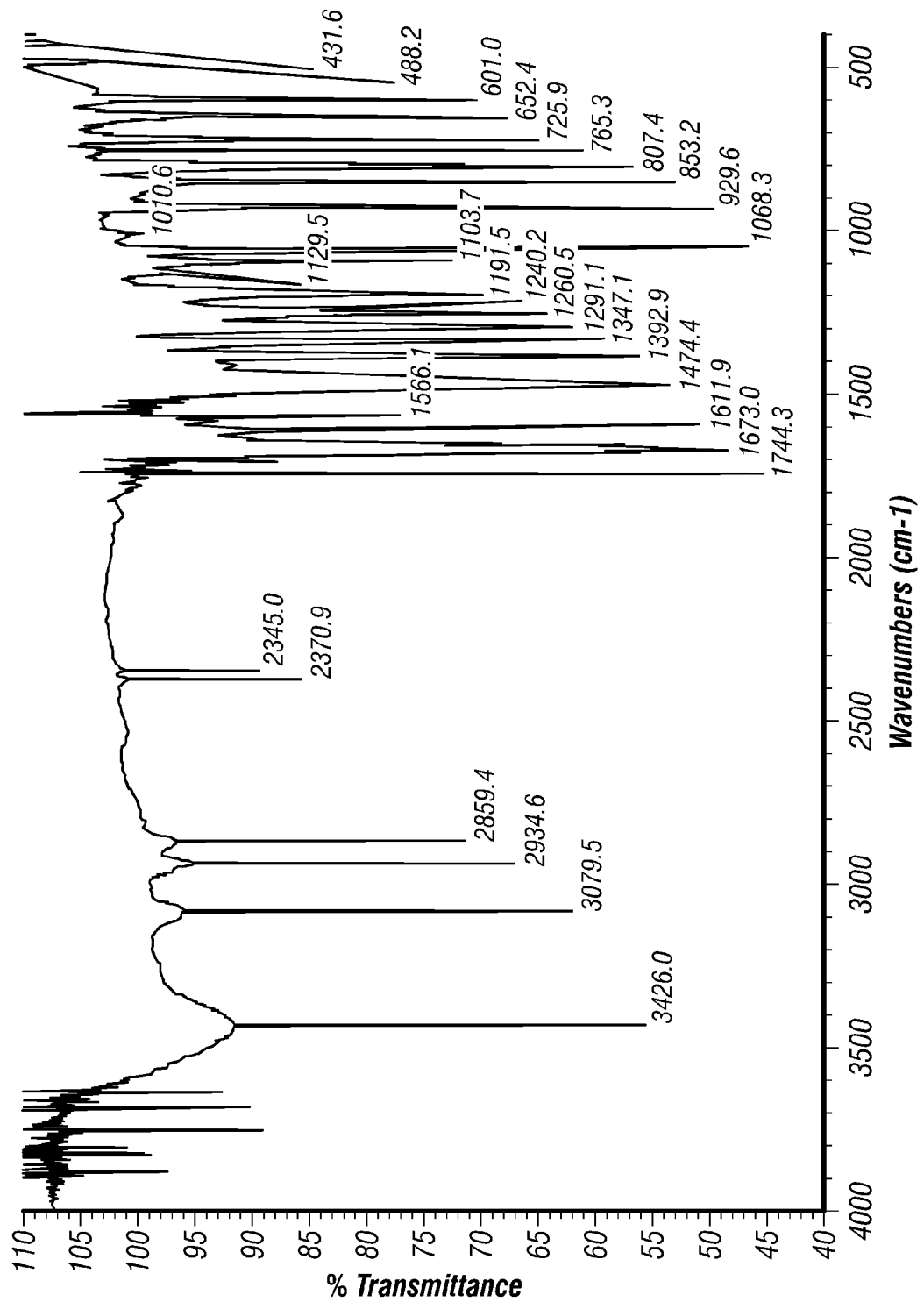
FIG. 23 shows FT-IR spectrum of as-synthesized ZIF-95.
Figure 24:
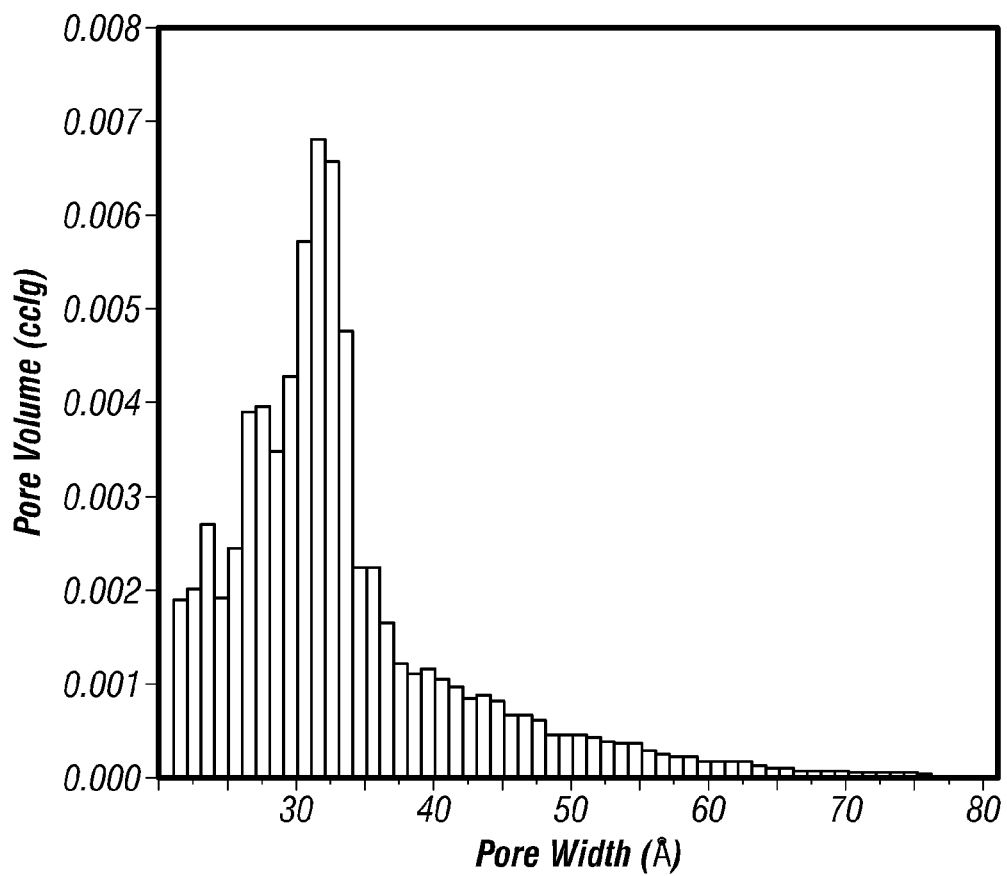
FIG. 24 shows Pore size distribution histogram of ZIF-100 using NLDFT Arzeolites/silica model on the adsorption branch (the fitting error was 0.105%).

The thermal gravimetric analysis (TGA) (FIG. 5) and powder X-ray (FIG. 6) diffraction (PXRD) proved the thermal stability of both ZIF-100 and -105 up to 500° C. Full activation of the materials was achieved by soaking crystals in methanol for 72 h and heating at 100° C. under reduced pressure ($10^{-3}$ Torr) for 50° C. for 12 h and then at 100° C. for 12 h; their permanent porosity subsequently proven using a combination of Ar and $CO_2$ adsorption measurements. The Langmuir surface areas were 800 $m^2/g$ and 1260 $m^2/g$ for ZIF-100 and -105, respectively, which more than double those of the most porous zeolites. During adsorption analysis very slow diffusion of gas was evident for both ZIFs, which can be ascribed to the size of the pore apertures which are close the kinetic diameters of many gasses and therefore restrictive toward migration of gasses into the pores. We appropriated this unique structural feature of ZIF-100 and -105 for gas separation. We successfully separated $CO_2$ from $CH_4$ and $CO_2$ from $N_2$ using ZIF 100 and ZIF 105 as the absorbent material in the separation columns.

The table below provides a list of ZIFs tested for carbon dioxide sorption:

| Mat. Codes | Struc. | Linker | Composition |
|---|---|---|---|
| ZIF-20 | LTA | Purinate | $ZnC_{10}H_6N_8$ |
| ZIF-25 | RHO | 4,5-Dimethylimidazolate | $CoC_{10}H_{14}N_4$ |
| ZIF-26 | RHO | 4,5-Dimethylimidazolate | $ZnC_{10}H_{14}N_4$ |
| ZIF-100 | — | 5-Chlorobenzimidazolate | $ZnC_{14}H_8N_4C_{l2}$ |
| ZIF-105 | — | 5-Chlorobenzimidazolate | $ZnC_{14}H_8N_4C_{l2}$ |
| ZIF-108 | SOD | 2-Nitroimidazolate | $ZnC_6H_4N_6O_4$ |

Material: ZIF-20. The as-synthesized sample of ZIF-20 was immersed in anhydrous methanol in a glove box for 3 days, during the exchange methanol was refreshed six times. The resulting methanol-exchanged sample was transferred to quartz cell in a glove box and the solvent was roughly decanted by pipette. The wet sample then was evacuated at ambient temperature for 12 h to yield an activated sample for gas adsorption measurements. The sample cell with a filler rod was attached to a valve in a grove box, which was kept closing until the start of the measurement, and then attached to the instrument without exposing the sample to air.

Material: ZIF-25. The as-synthesized sample of ZIF-25 was immersed in acetone in a glove box for 3 days, during the exchange solvent was refreshed six times. The resulting acetone-exchanged sample was evacuated at ambient temperature for 12 hours to yield an activated sample.

Material: ZIF-26. The as-synthesized sample of ZIF-26 was immersed in acetonitrile in a glove box for 3 days, during the exchange solvent was refreshed six times. The resulting acetonitrile-exchanged sample was evacuated at ambient temperature for 12 hours to yield an activated sample.

Material: ZIF-100. The as-synthesized sample of ZIF-100 was immersed in anhydrous methanol in a glove box for 3 days, during the exchange methanol was refreshed three times. The resulting methanol-exchanged sample was transferred to quartz cell in a glove box and the solvent was roughly decanted by pipette. The wet sample then was evacuated at 100° C. for 12 hours to yield an activated sample for gas adsorption measurements.

Material: ZIF-105. The as-synthesized sample of ZIF-105 was immersed in acetone for 3 days, during the exchange methanol was refreshed three times. The resulting acetone-exchanged sample was transferred to quartz cell and the solvent was roughly decanted by pipette. The wet sample then was evacuated at 50° C. for 12 hours to yield an activated sample for gas adsorption measurements.

Material: ZIF-108. The as-synthesized crystals of ZIF-108 was immersed in methanol in a capped vial for 3 days, during the exchange, methanol was refreshed three times. The resulting methanol-exchanged sample was transferred to quartz cell and the solvent was roughly decanted by pipette. The wet sample then was evacuated at ambient temperature for 24 hours to yield an activated sample for gas adsorption measurements.

Hydrogen adsorption by ZIFs: Provided herein are porous Zeolitic Frameworks (COFs) having functionalized pore, high surface area, and high chemical and thermal stability as adsorbents for reversible hydrogen storage. These materials could be widely applicable to store significant amounts of H2 in a safe and practical way.

Several crystalline porous materials of ZIFs have been reported recently by our group. From their crystal structures, though it is expected that a series of crystalline materials captures large amount of hydrogen, uptake behavior of H2 has not been studied systematically yet. Also since there are only few crystalline materials whose possess different pore sizes and functionalities but similar chemical compositions, optimization of pore systems in porous solid for H2 storage by experimentally (not computer simulation) was not performed.

In this discovery six ZIFs have been examined as candidates for H2 storage materials. Since these compounds possess various pore diameters and functionalities, systematic studies on H2 sorption behavior should be possible. Gas sorption isotherms were taken under low pressure region (up to 800 Torr) at 77° K. and high-pressure region (up to 85 bar) at 77 and 298° K. Examined compounds are stable under high pressure atmosphere (up to 85 bar) and did not show significant drop of gas storage capacity with adsorption-desorption cycles.

In another embodiment, the materials may be used in an H2 tank for hydrogen-powered fuel cells. The advantage of ZIFs over well studied activated carbons is related to the robust porous structures and the ease to functionalize the pore and surface by choosing appropriate organic linkers and/or metal ions. Improvements in this invention are that i) optimized pore size for H2 sorption has been discovered and ii) functionalized compounds show good sorption capacities. These discoveries will lead ZIFs to become more selective and more efficient H2 storage materials.

The ability of gas sorption has been examined by measuring H2 isotherms under wide range pressure. Some compound showed high capacity rather than zeolite 13X and activated carbon which are widely used as adsorbents or separation agents. Several materials are already synthesized in gram scale order successfully, leading that these materials can be tested as a practical phase.

These materials should be desired by car companies who wish to have new porous materials for $H_2$-powered fuel cells.

The table below provides a list of ZIFs tested for hydrogen sorption:

| Matl. Codes | Struc. | Linker | Composition |
|---|---|---|---|
| ZIF-20 | LTA | Purinate | $ZnC_{10}H_6N_8$ |
| ZIF-25 | RHO | 4,5-Dimethylimidazolate | $CoC_{10}H_{14}N_4$ |
| ZIF-26 | RHO | 4,5-Dimethylimidazolate | $ZnC_{10}H_{14}N_4$ |

-continued

| Matl. Codes | Struc. | Linker | Composition |
|---|---|---|---|
| ZIF-100 | — | 5-Chlorobenzimidazolate | $ZnC_{14}H_8N_4C_{l2}$ |
| ZIF-105 | — | 5-Chlorobenzimidazolate | $ZnC_{14}H_8N_4C_{l2}$ |
| ZIF-108 | SOD | 2-Nitroimidazolate | $ZnC_6H_4N_6O_4$ |

General procedures: Low pressure $H_2$ adsorption isotherms at 273° K. were measured volumetrically on an Autosorb-1 analyzer (Quantachrome Instruments). High-pressure $H_2$ sorption isotherms were measured by the gravimetric method at 77 and 298° K. using a customized GHP-S-R instrument from the VTI Corporation. A Rubotherm magnetic suspension balance was used to measure the change in mass of samples. For buoyancy correction, the volume of the crystals was determined by the high-pressure helium isotherm.

Material: ZIF-100. The as-synthesized sample of ZIF-100 was immersed in anhydrous methanol in a glove box for 3 days, during the exchange methanol was refreshed three times. The resulting methanol-exchanged sample was transferred to quartz cell in a glove box and the solvent was roughly decanted by pipette. The wet sample then was evacuated at 100° C. for 12 hours to yield an activated sample for gas adsorption measurements.

Material: ZIF-105. The as-synthesized sample of ZIF-105 was immersed in acetone for 3 days, during the exchange methanol was refreshed three times. The resulting acetone-exchanged sample was transferred to quartz cell and the solvent was roughly decanted by pipette. The wet sample then was evacuated at 50° C. for 12 hours to yield an activated sample for gas adsorption measurements.

Material: ZIF-108. The as-synthesized crystals of ZIF-108 was immersed in methanol in a capped vial for 3 days, during the exchange, methanol was refreshed three times. The resulting methanol-exchanged sample was transferred to quartz cell and the solvent was roughly decanted by pipette. The wet sample then was evacuated at ambient temperature for 24 hours to yield an activated sample for gas adsorption measurements.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A zeolitic framework ("ZIF") comprising a plurality of the structure M-L-M, wherein M comprises a transition metal and L is a linking moiety, and wherein the framework has either POZ or MOZ topology, a thermostability range of at least up to 500° C. and a Langmuir surface area of about 1,240 $m^2/g^{-1}$ or 780 $m^2/g^{-1}$ or a BET method surface area of about 1,050 $m^2/g^{-1}$ or 595 $m^2/g^{-1}$.

2. The zeolitic framework of claim 1, wherein the zeolitic framework comprises a plurality of pores, each of the plurality of pores comprises a sufficient number of accessible sites for atomic or molecular adsorption.

3. The zeolitic framework of claim 1, further comprising a guest species.

4. The zeolitic framework of claim 3, wherein the guest species increase the surface area of the zeolitic framework.

5. The zeolitic framework of claim 3, wherein the guest species is selected from the group consisting of organic molecules with a molecular weight less than 100 g/mol, organic molecules with a molecular weight less than 300 g/mol, organic molecules with a molecular weight less than 600 g/mol, organic molecules with a molecular weight greater than 600 g/mol, organic molecules containing at least one aromatic ring, polycyclic aromatic hydrocarbons, and metal complexes having formula $M_mX_n$ where M is metal ion, X is selected from the group consisting of a Group 14 through Group 17 anion, m is an integer from 1 to 10, and n is a number selected to charge balance the metal cluster so that the metal cluster has a predetermined electric charge; and combinations thereof.

6. The zeolitic framework of claim 1, further comprising an interpenetrating zeolitic framework that increases the surface area of the zeolitic framework.

7. The zeolitic framework of claim 1, wherein the framework comprises a plurality M-L-M structures of structure II:

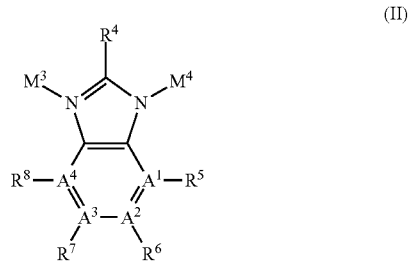

(II)

wherein,
$M^3$ and $M^4$ are each individually selected transition metals;
$A^1, A^2, A^3$ and $A^4$ are each individually C or N, and if $A^1$ is N then $R^5$ is absent, and/or if $A^4$ is N then $R^8$ is absent;
$R^4$ is a non-sterically hindering group that does not interfere with $M^3$ or $M^4$;
$R^5$ and $R^8$ are each individually an alkyl, hydrogen, halo, cyano, or nitro; and
$R^6$ and $R^7$ are each individually selected electron withdrawing groups.

8. The zeolitic framework of claim 7, wherein the framework further comprises one or more M-L-M structures of structure I and/or structure III:

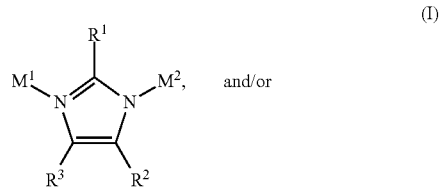

(I) and/or

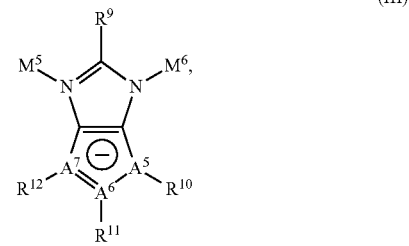

(III)

wherein,
$M^1$, $M^2$ $M^5$, and $M^6$ are each individually selected transition metals;
$A^5$, $A^6$ and $A^7$ are each individually C or N, and if $A^6$ is N then $R^{11}$ is absent, and/or if $A^7$ is N then $R^{12}$ is absent;

R$^1$ and R$^9$ are each individually selected non-sterically hindering groups which do not interfere with M$^1$, M$^2$, M$^5$, or M$^6$; and R$^2$, R$^3$, R$^{10}$, R$^{11}$, and R$^{12}$ are each individually an alkyl, hydrogen, halo, cyano, or nitro.

9. The zeolitic framework of claim 7, further comprising an adsorbed chemical species.

10. The zeolitic framework of claim 9, wherein the adsorbed chemical species is selected from the group consisting of ammonia, carbon dioxide, carbon monoxide, hydrogen, amines, methane, oxygen, argon, nitrogen, argon, organic dyes, polycyclic organic molecules, and combinations thereof.

11. The zeolitic framework of claim 8, wherein R$^1$, R$^4$ and R$^9$ are individually electron donor groups.

12. The zeolitic framework of claim 8, wherein R$^1$, R$^4$ and R$^9$ are each individually selected from the group consisting of H, methyl, halo, cyano, and ethyl.

13. The zeolitic framework of claim 7, wherein the electron withdrawing group is selected from the group consisting of a halogen, a nitrile, and a carbonyl.

14. The zeolitic framework on claim 13, wherein the electron withdrawing group is a halogen.

15. The zeolitic framework of claim 14, wherein the halogen is Cl.

16. The zeolitic framework of claim 8, wherein R$^{10}$, R$^{11}$ and R$^{12}$ are each individually selected from the group consisting of a nitro-, cyano-, fluoro- and chloro-group.

17. The zeolitic framework of claim 1, wherein the framework comprises imidazolate and/or imidazolate derivative linking moieties.

18. The zeolitic framework of claim 7, wherein the framework comprises one or more structures selected from the group consisting of:

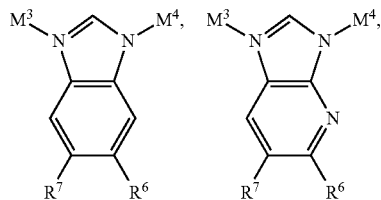

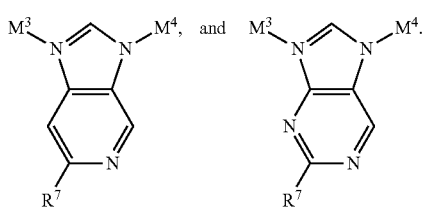

19. The zeolitic framework of claim 1, wherein the zeolitic framework comprises a plurality of different transition metals.

20. The zeolitic framework of claim 1, wherein the zeolitic framework comprises a plurality of different M-L-M structures, wherein at least one of the M-L-M structures comprise structure II:

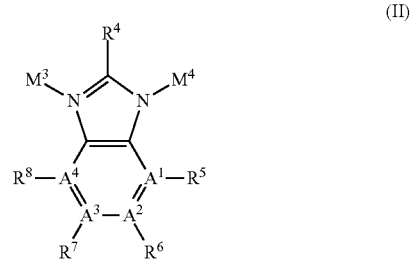

wherein,
M$^3$ and M$^4$ are each individually selected transition metals;
A$^1$, A$^2$, A$^3$ and A$^4$ are each individually C or N, and if A$^1$ is N then R$^5$ is absent, and/or if A$^4$ is N then R$^8$ is absent;
R$^4$ is a non-sterically hindering group that does not interfere with M$^3$ or M$^4$;
R$^5$ and R$^8$ are each individually an alkyl, hydrogen, halo, cyano, or nitro; and
R$^6$ and R$^7$ are each individually selected electron withdrawing groups.

21. The zeolitic framework of claim 7, wherein the transition metal is selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub.

22. The zeolitic framework of claim 17, wherein the imidazolate or imidazolate derivative is selected from the group consisting of a substituted imidazolate; a benzimidazolate comprising a methyl-, nitro-, cyano-, or chloro-group; an azabenzimidazolate; and an azabenzimidazolate wherein one or two carbon atoms on the benzimidazolate are replaced by nitrogen.

23. A gas storage device comprising a zeolitic framework of claim 7.

24. A catalyst substrate comprising a zeolitic framework of claim 7.

25. A device for the sorptive uptake of a chemical species, the device comprising a sorbent comprising a zeolitic framework (ZIF) of claim 7 for the uptake of the chemical species.

26. The device of claim 25, wherein the uptake is reversible.

27. The device of claim 25, wherein the sorbent is comprised of discrete sorptive particles.

28. The device of claim 27, wherein the sorptive particles are embedded into or fixed to a solid liquid- and/or gas-permeable three-dimensional support.

29. The device of claim 27, wherein the sorptive particles have pores for the reversible uptake or storage of liquids or gases and wherein the sorptive particles can reversibly adsorb or absorb the liquid or gas.

30. The device of claim 25, wherein the chemical species is in the form of a gas.

31. The device of claim 25, wherein the chemical species is in the form of a liquid.

32. The device of claim 25, wherein the device is a storage unit.

33. The device of claim 25, wherein the adsorbed chemical species is selected from the group consisting of ammonia, carbon dioxide, carbon monoxide, hydrogen, amines, methane, oxygen, argon, nitrogen, argon, organic dyes, polycyclic organic molecules, and combinations thereof.

34. A method for the sorptive uptake of a chemical species, the method comprising contacting the chemical species with a sorbent comprising a zeolitic framework (ZIF) of claim 7.

35. The method of claim 34, wherein the uptake is reversible.

36. The method of claim 34, wherein the adsorbed chemical species is selected from the group consisting of ammonia, carbon dioxide, carbon monoxide, hydrogen, amines, methane, oxygen, argon, nitrogen, argon, organic dyes, polycyclic organic molecules, and combinations thereof.

37. The method of claim 34, wherein the uptake of a chemical species comprises storage of the chemical species.

38. The method of claim 37, wherein the chemical species is stored under conditions suitable for use as an energy source.

39. A method for the sorptive uptake of a chemical species, the method comprising contacting the chemical species with a device of claim 25.

* * * * *